(12) United States Patent
Frankish et al.

(10) Patent No.: US 9,260,376 B2
(45) Date of Patent: Feb. 16, 2016

(54) COMPOUNDS FOR USE IN THE TREATMENT OF IMMUNE RELATED INFLAMMATORY DISEASE

(75) Inventors: Neil Frankish, Dublin (IE); Helen Sheridan, Dublin (IE)

(73) Assignee: VENANTIUS LIMITED, Dublin (IE)

( * ) Notice: Subject to any disclaimer, the term of this patent is extended or adjusted under 35 U.S.C. 154(b) by 0 days.

(21) Appl. No.: 14/124,956

(22) PCT Filed: Jul. 20, 2012

(86) PCT No.: PCT/IE2012/000038
§ 371 (c)(1),
(2), (4) Date: Dec. 9, 2013

(87) PCT Pub. No.: WO2013/014660
PCT Pub. Date: Jan. 31, 2013

(65) Prior Publication Data
US 2014/0107194 A1    Apr. 17, 2014

Related U.S. Application Data

(60) Provisional application No. 61/510,675, filed on Jul. 22, 2011, provisional application No. 61/651,156, filed on May 24, 2012.

(51) Int. Cl.
| | |
|---|---|
| *C07C 69/78* | (2006.01) |
| *C07C 65/17* | (2006.01) |
| *C07C 215/12* | (2006.01) |
| *C07C 235/42* | (2006.01) |
| *C07C 229/38* | (2006.01) |
| *C07C 65/19* | (2006.01) |
| *C07C 69/76* | (2006.01) |
| *C07C 215/10* | (2006.01) |
| *C07C 229/08* | (2006.01) |

(52) U.S. Cl.
CPC ............... *C07C 69/78* (2013.01); *C07C 65/17* (2013.01); *C07C 65/19* (2013.01); *C07C 69/76* (2013.01); *C07C 215/10* (2013.01); *C07C 215/12* (2013.01); *C07C 229/08* (2013.01); *C07C 229/38* (2013.01); *C07C 235/42* (2013.01); *C07B 2200/07* (2013.01); *C07C 2102/08* (2013.01)

(58) Field of Classification Search
None
See application file for complete search history.

(56) References Cited

FOREIGN PATENT DOCUMENTS

WO    97/20802 A1    6/1997

OTHER PUBLICATIONS

Bernstein et al., (American Journal of Epidemiology vol. 149, No. 10 (1999)).*
Jordan, V. C. (Nature Reviews: Drug Discovery, 2, 2003, 205-213).*
Neil Frankish et al, "6-(Methylamino)hexane-1,2,3,4,5-pentanol 4-(((1S,2S)-1-Hydroxy-2,3-dihydro-1H,1'H-[2,2-biinden]-2-yl)methyl)benzoate (PH46A): A Novel Small Molecule With Efficacy in Murine Models of Colitis", Journal of Medicinal Chemistry, American Chemical Society, Jun. 4, 2012.
Benjiamin Sadlack et al, "Ulcerative Colitis-like Disease in Mice with a Disrupted Interleukin-2 Gene", Cell Press, vol. 75, pp. 253-261, Oct. 22, 1993.
Shoshana D. Katzman et al, "Opposing functions of IL-2 and IL-7 in the regulation of immune responses", Cytokine, Author manuscript, available in PMC, Oct. 1, 2012.

* cited by examiner

*Primary Examiner* — Jeffrey S Lundgren
*Assistant Examiner* — William Lee
(74) *Attorney, Agent, or Firm* — Bookoff McAndrews, PLLC

(57) ABSTRACT

Compounds particularly for use in an autoimmune inflammatory disease and especially the treatment of inflammatory bowel disease have the formula: wherein R is selected from one or more of the same or different of hydrogen, hydroxyl, optionally substituted alkyl, optionally substituted aryl, alkoxy, aryloxy, thiol, and optionally substituted amino, and wherein R1 is selected from one or more of the same or different of hydrogen, acetyl, optionally substituted alkyl, optionally substituted aryl, and an amino acid selected from leucine, valine, isoleucine, and glycine.

4 Claims, 20 Drawing Sheets

COMPOUNDS FOR USE IN THE TREATMENT OF IMMUNE RELATED INFLAMMATORY DISEASE

This is a national stage of PCT/IE12/000038 filed Jul. 20, 2012 and published in English, which has a U.S. priority of no. 61/510,675 filed Jul. 22, 2011, and U.S. priority of No. 61/651,155 filed May 21, 2012, hereby incorporated by reference.

This invention relates to compounds particularly for use in the autoimmune inflammatory disease and specifically the treatment of inflammatory bowel disease.

INTRODUCTION

Cytokines can be produced by various cell populations and have been shown to augment or limit immune responses to pathogens and influence the autoimmune response. One family of cytokines, which uses the common receptor gamma chain (cc), a component of receptors for interleukin (IL)-2, IL-4, IL-7, IL-9, IL-15 and IL-21, has been classically defined as growth and survival factors.

IL-2 production can induce an immune response by promoting the proliferation and generation of CD4+ Th1, CD4+ Th2 and CD8+ CTL effector cells. Many of the immunosuppressive drugs used in the treatment of autoimmune diseases and organ transplant rejection, such as corticosteroids and immune suppressive drugs (ciclosporin, tacrolimus) work by inhibiting the production of IL-2 by antigen-activated T cells. Others (sirolimus) block IL-2R signalling, thereby preventing the clonal expansion and function of antigen-selected T cells [ref: Opposing functions of IL-2 and IL-7 in the regulation of immune responses Shoshana D. Katzman, Katrina K. Hoyer, Hans Dooms, Iris K. Gratz, Michael D. Rosenblum, Jonathan S. Paw, Sara H. Isakson, Abul K. Abbas. Cytokine 56 (2011) 116-121]

In contrast IL-2 can inhibit the immune response by promoting the survival and functionality of natural (thymic) regulatory T-cells (Tregs), promoting the generation of induced (peripheral) Tregs and inhibiting the generation of CD4+ Th17 effector cells [ref: IL-2 and autoimmune disease. Anneliese Schimpl, A., Berberich, I, Kneitz, B., Krämer, S., Santner-Nanan, B., Wagner, S., Wolf, M., Hünig, T. Cytokine & Growth Factor Reviews 13 (2002) 369-378]. Interleukin-2/IL-2R deficiency with time leads to multiorgan inflammation and the formation of autoantibodies of various specificities. Depending on the genetic background, death occurs within a few weeks to a few months, mostly from autoimmune hemolytic anemia or inflammatory bowel disease (IBD) [ref. Sadlack B, Merz H, Schorle H, Schimpi A, Feller A C, Horak I. Ulcerative colitis-like disease in mice with a disrupted interleukin-2 gene. Cell 1993; 75:253-61].

IL-2 signalling has been shown to be important in both the initiation and regulation of immune responses. In these dual and opposing roles, IL-2 acts to balance immune response, both driving immune cell activation and subsequent reduction. The potential clinical applicability of either augmenting or inhibiting signals mediated by IL-2 is significant and includes cancer, autoimmune inflammatory diseases, organ transplantation and HIV.

Inflammatory bowel disease (IBD) is an autoimmune inflammatory disease that consists of two idiopathic inflammatory diseases, ulcerative colitis (UC) and Crohn's disease (CD). The greatest distinction between UC and CD is the range of inflamed bowel tissue. Inflammation in CD is discontinuously segmented, known as regional enteritis, while UC is superficial inflammation extending proximally and continuously from the rectum. At present, the exact cause of IBD is unknown. The disease seems to be related to an exaggerated mucosal immune response to infection of the intestinal epithelium because of an imbalance of pro-inflammatory and immune-regulatory molecules. The inheritance patterns of IBD suggest a complex genetic component of pathogenesis that may consist of several combined genetic mutations. Currently no specific diagnostic test exists for IBD, but as an understanding of pathogenesis is improved so will the corresponding testing methods. Treatment of IBD consists of inducing and maintaining remission. IBD patients may be maintained on remission by use of a 5-aminosalycilate. However, while the use of aminosalycilates in UC provides considerable benefit, both in inducing remission in mild to moderate disease and in preventing relapse, the usefulness of these drugs to maintain remission in CD is questionable and is no longer recommended. The mainstay of treatment of active disease is a corticosteroid, commonly used for limited periods to return both UC and CD patients to remission, though budesonide, designed for topical administration with limited systemic absorption, has no benefit in maintaining remission. Alternatives, such as the immunosuppressive drugs azathioprine and mercaptopurine, together with methotrexate and cyclosporine have limited efficacy and the capability of inducing grave adverse effects. Anti-TNFα antibodies, such as infliximab and adalimubab, may be used in those patients unresponsive to standard immunosuppressive therapy. However, many patients fail to respond to anti-TNFα therapy, either due to their particular phenotype or by the production of autoantibodies.

STATEMENTS OF INVENTION

In accordance with the present invention there are provided compounds for use in the treatment of autoimmune inflammatory disease and specifically inflammatory bowel disease including Crohn's disease and ulcerative colitis.

In one aspect the invention provides a compound of the relative stereochemistry and formula:

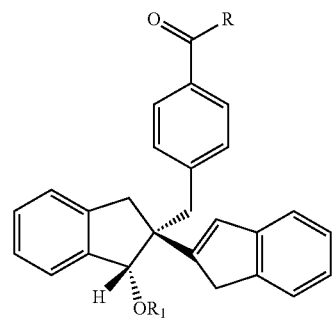

wherein R is selected from one or more of the same or different of
hydrogen,
hydroxyl,
optionally substituted alkyl,
optionally substituted aryl,
alkoxy,
aryloxy,
thiol, and
optionally substituted amino, and wherein $R_1$ is selected from one or more of the same or different of
hydrogen,
acetyl,
optionally substituted alkyl,
optionally substituted aryl, and
an amino acid selected from leucine, valine, isoleucine, and glycine, In all cases the compounds herein include pharmacologically acceptable salts, esters, amides, solvates, and prodrugs thereof.

The invention also provides a compound of the absolute stereochemistry and formula:

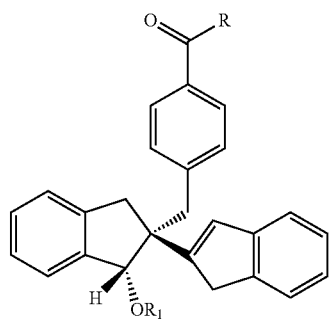

wherein R is selected from one or more of the same or different of
hydrogen,
hydroxyl,
optionally substituted alkyl,
optionally substituted aryl,
alkoxy,
aryloxy,
thiol, and
optionally substituted amino,
and wherein $R_1$ is selected from one or more of the same or different of
hydrogen,
acetyl,
optionally substituted alkyl,
optionally substituted aryl, and
an amino acid selected from leucine, valine, isoleucine, and glycine.

In one embodiment alkyl contains from 1 to 10 carbon atoms in a straight or branched chain and may be saturated or unsaturated, or cycloalkyl groups containing 3 to 8 carbon atoms which may be saturated or unsaturated.

In some embodiments alkyl is substituted with one or more of the same or different from alkyl, alkoxy, alkylamino, amido, amino, aryl, aralkyl, aryloxy, carboxy, halo, hydroxy, nitrile, nitro or oxo groups.

In one embodiment aryl is substituted with one or more of the same or different from alkyl, alkoxy, alkylamino, amido, amino, anhydride, aryl, aralkyl, aryloxy, carboxy, halo, hydroxy, nitrile, nitro, or oxo groups.

In one embodiment amino is substituted with one or more of the same of different from alkyl, hydroxyalkyl, aryl, and substituted aryl. In some cases amino is substituted with aryl substituted by one or more of OH, $NH_2$, and COOH.

In one embodiment R is OH.
In one embodiment $R_1$ is H.

The invention also provides compounds of the following formula with the absolute stereochemistry and formula

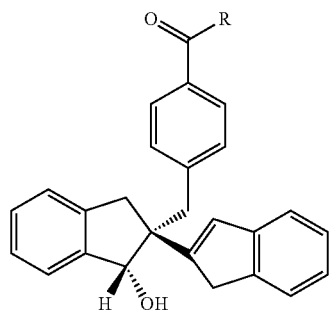

wherein R is selected from: OH, $OCH_3$, $OCH_2CH_3$, $OCH_2CH_2CH_3$, $NH_2$, $NHCH_2CH_2OH$, $NHCH_3$, $N(CH_3)_2$, NH(4-OH-3-benzoic acid)

Also provided are compounds of the absolute stereochemistry and formula

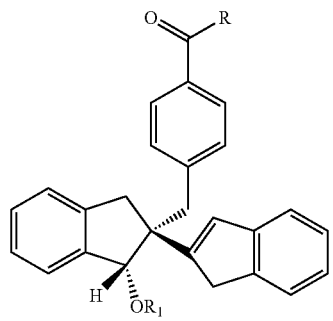

wherein $R^1$ is H or leucine and R is selected from: OH, $OCH_3$, $OCH_2CH_3$, $OCH_2CH_2CH_3$, $NH_2$, $NHCH_2CH_2OH$, $NHCH_3$, $N(CH_3)_2$, NH(4-OH-3-benzoic acid).

In some aspects R may be selected from one or more of the same or different of: H, hydroxy, alkoxy, alkyl carbonyl, aryloxy, anhydride, substituted anhydride, amino, substituted amino, amide, alkylamino, nitro, nitrite, nitrile, mono and polybenzoid aryl groups, substituted aryl groups, thiol, thioureyl, phenylthiol groups, sulphonic acid groups, sulphoxide groups, sulphone groups, alkyl containing 1 to 10 carbon atoms or cycloalkyl groups containing 3 to 8 carbon atoms which may be saturated or unsaturated, and substituted alkyl or cycloalkyl which may be saturated or unsaturated.

In some aspects $R_1$ may be selected from one or more of the same or different of: H, alkoxy, alkyl carbonyl, aryl, acetoxy, alkyl containing 1 to 10 carbon atoms or cycloalkyl groups containing 3 to 8 carbon atoms which may be saturated or unsaturated, substituted alkyl, and an amino acid selected from leucine, valine, isoleucine, and glycine.

Also provided are pharmacologically acceptable salts, esters, amides and solvates thereof.

In one embodiment alkyl or cycloalkyl are substituted with one or more of the same of different of halo, oxo, hydroxy, alkoxy, aryloxy, carboxy, amino, amide, alkylamino, nitro, nitrate, nitrite, nitroso groups, nitrile, heterocyclic groups, aryl, aralkyl groups, alkyl substituted by OH, COOH, and/or $NH_2$.

In one embodiment amino is substituted with one or more of the same of different of hydroxyl, alkylhydroxyl, aryl, and aryl substituted by one or more of OH, $NH_2$, and COOH.

In one case anhydride is substituted with aryl or aryl substituted by one or more of OH, $NH_2$, and COOH.

In one embodiment R is OH and $R_1$ is H.

In some cases R is not OH. In this instance, in some cases salts thereof are excluded.

In some cases $R_1$ is not H. In this instance, in some cases salts thereof are excluded.

In some cases R is not OH and $R_1$ is not H. In this instance, in some cases salts thereof are excluded.

The invention also provides compounds of the structural formula I:

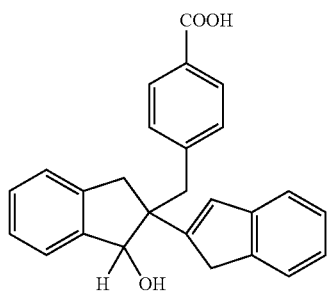

I

Also provided are pharmacologically acceptable isomers and salts of the compound of formula (I)—compound 1.

In particular, the present invention provides compounds of relative stereochemistry as demonstrated in structural formula II:

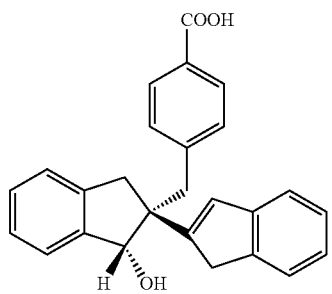

(II)

Also provided are pharmacologically acceptable salts of the compound of formula (II)—compound 2.

The active enantiomers have been characterised, spectroscopically, by their physical and chemical properties and by normal and chiral HPLC retention data.

A specific enantiomeric form has been found to be particularly useful for the treatment of IBD.

The invention also provides the N-Methyl-(D)-Glucamine salt of the compound of formula III:

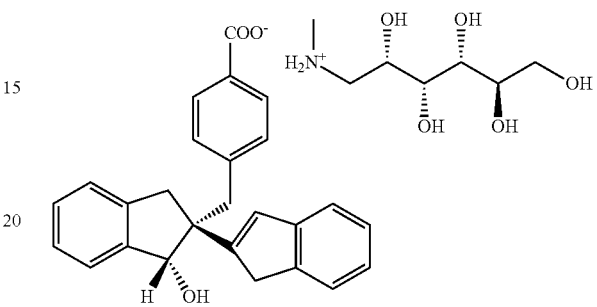

(III, compound 6)

The invention further provides a pharmaceutical composition comprising an effective amount of a compound of the invention and a pharmaceutically acceptable carrier.

The invention also provides a method for the prophylaxis or treatment of inflammatory bowel disease, comprising administering to a subject an effective amount of a compound of the invention.

The invention further provides a method for the prophylaxis or treatment of ulcerative colitis, comprising administering to a subject an effective amount of a compound of the invention.

Also provided is a method for the prophylaxis or treatment of Crohn's disease, comprising administering to a subject an effective amount of a compound of the invention.

The compounds of the invention are also potentially useful in either augmenting or inhibiting signals mediated by IL-2. The clinical uses include the treatment of cancer, autoimmune inflammatory disorders, organ transplantation and HIV.

In particular the invention provides a compound as exemplified below

| Compound No. | Chemical Name |
|---|---|
| 1 | 4-(((1S,2S)-1-hydroxy-2,3-dihydro-1H,1'H-2,2'-biinden-2-yl) methyl)benzoic acid |
| 2 | 4-(((1S,2S)-1-hydroxy-2,3-dihydro-1H,1'H-2,2'-biinden-2-yl) methyl)benzoic acid |
| 3 | 4-(((1R,2R)-1-hydroxy-2,3-dihydro-1H,1'H-2,2'-biinden-2-yl)methyl)benzoic acid |
| 4 | 4-(((1R,2S)-1-hydroxy-2,3-dihydro-1H,1'H-2,2'-biinden-2-yl)methyl)benzoic acid |
| 5 | 4-(((1S,2R)-1-hydroxy-2,3-dihydro-1H,1'H-2,2'-biinden-2-yl)methyl)benzoic acid |
| 6 | 6-(Methylamino)hexane-1,2,3,4,5-pentanol 4-(((1S,2S)-1-hydroxy-2,3-dihydro-1H,1'H-2,2'-biinden-2-yl)methyl)benzoate |
| 7 | 6-(Methylamino)hexane-1,2,3,4,5-pentanol 4-(((1S,2R)-1-hydroxy-2,3-dihydro-1H,1'H-2,2'-biinden-2-yl)methyl)benzoate |
| 8 | (S)-1-Phenylethylammonium 4-(((1S,2S)-1-hydroxy-2,3-dihydro-1H,1'H-2,2'-biinden-2-yl)methyl)benzoate |
| 9 | (R)-1-Phenylethylammonium 4-(((1R,2S)-1-hydroxy-2,3-dihydro-1H,1'H-2,2'-biinden-2-yl)methyl)benzoate |
| 10 | methyl 4-(((1R,2R)-1-hydroxy-2,3-dihydro-1H,1'H-[2,2'-biinden]-2-yl)methyl)benzoate |
| 11 | ethyl 4-(((1R,2R)-1-hydroxy-2,3-dihydro-1H,1'H-[2,2'-biinden]-2-yl)methyl)benzoate |

-continued

| Compound No. | Chemical Name |
|---|---|
| 12 | propyl 4-(((1R,2R)-1-hydroxy-2,3-dihydro-1H,1'H-[2,2'-biinden]-2-yl)methyl)benzoate |
| 13 | 4-{[(1'R,2'R)-1'-hydroxy-1',3'-dihydro-1H,2'H-2,2'-biinden-2'-yl]methyl} Benzamide |
| 14 | 4-{[(1'R,2'R)-1'-hydroxy-1',3'-dihydro-1H,2'H-2,2'-biinden-2'-yl]methyl}-N-(2-hydroxyethyl)benzamide |
| 15 | 4-{[(1'R,2'R)-1'-hydroxy-1',3'-dihydro-1H,2'H-2,2'-biinden-2'-yl]methyl}-N-methylbenzamide |
| 16 | 4-{[(1'R,2'R)-1'-hydroxy-1',3'-dihydro-1H,2'H-2,2'-biinden-2'-yl]methyl}-N,N-dimethylbenzamide |
| 17 | methyl 4-(((1S,2S)-1-hydroxy-2,3-dihydro-1H,1'H-[2,2'-biinden]-2-yl)methyl)benzoate |
| 18 | ethyl 4-(((1S,2S)-1-hydroxy-2,3-dihydro-1H,1'H-[2,2'-biinden]-2-yl)methyl)benzoate |
| 19 | propyl 4-(((1S,2S)-1-hydroxy-2,3-dihydro-1H,1'H-[2,2'-biinden]-2-yl)methyl)benzoate |
| 20 | 4-{[(1'S,2'S)-1'-hydroxy-1',3'-dihydro-1H,2'H-2,2'-biinden-2'-yl]methyl} Benzamide |
| 21 | 4-{[(1'S,2'S)-1'-hydroxy-1',3'-dihydro-1H,2'H-2,2'-biinden-2'-yl]methyl}-N-(2-hydroxyethyl)benzamide |
| 22 | 4-{[(1'S,2'S)-1'-hydroxy-1',3'-dihydro-1H,2'H-2,2'-biinden-2'-yl]methyl}-N-methylbenzamide |
| 23 | 4-{[(1'S,2'S)-1'-hydroxy-1',3'-dihydro-1H,2'H-2,2'-biinden-2'-yl]methyl}-N,N-dimethylbenzamide |
| 24 | 4-{[(1'R,2'R)-1'-(L-leucyloxy)-1',3'-dihydro-1H,2'H-2,2'-biinden-2'-yl]methyl} benzoic acid |
| 25 | 4-{[(1'R,2'R)-1'-(L-valyloxy)-1',3'-dihydro-1H,2'H-2,2'-biinden-2'-yl]methyl} benzoic acid |
| 26 | 4-{[(1'R,2'R)-1'-(L-isoleucyloxy)-1',3'-dihydro-1H,2'H-2,2'-biinden-2'yl]methyl}benzoic acid |
| 27 | 4-{[(1'R,2'R)-1'-(glycyloxy)-1',3'-dihydro-1H,2'H-2,2'-biinden-2'-yl]methyl} benzoic acid |
| 28 | 4-{[(1'S,2'S)-1'-(L-leucyloxy)-1',3'-dihydro-1H,2'H-2,2'-biinden-2'-yl]methyl} benzoic acid |
| 29 | 4-{[(1'S,2'S)-1'-(L-valyloxy)-1',3'-dihydro-1H,2'H-2,2'-biinden-2'-yl]methyl} benzoic acid |
| 30 | 4-{[(1'S,2'S)-1'-(L-isoleucyloxy)-1',3'-dihydro-1H,2'H-2,2'-biinden-2'-yl]methyl}benzoic acid |
| 31 | 4-{[(1'S,2'S)-1'-(glycyloxy)-1',3'-dihydro-1H,2'H-2,2'-biinden-2'-yl]methyl}benzoic acid |
| 32 | methyl 4-(((1R,2R)-1-(((S)-2-amino-4-methylpentanoyl)oxy)-2,3-dihydro-1H,1'H-[2,2'-biinden]-2-yl)methyl)benzoate |
| 33 | ethyl 4-(((1R,2R)-1-(((S)-2-amino-4-methylpentanoyl)oxy)-2,3-dihydro-1H,1'H-[2,2'-biinden]-2-yl)methyl)benzoate |
| 34 | propyl 4-(((1R,2R)-1-(((S)-2-amino-4-methylpentanoyl)oxy)-2,3-dihydro-1H,1'H-[2,2'-biinden]-2-yl)methyl)benzoate |
| 35 | (1R,2R)-2-(4-carbamoylbenzyl)-2,3-dihydro-1H,1'H-2,2'-biinden-1-yl L-leucinate |
| 36 | (1R,2R)-2-{4-[(2-hydroxyethyl)carbamoyl]benzyl}-2,3-dihydro-1H,1'H-2,2'-biinden-1-yl L-leucinate |
| 37 | (1R,2R)-2-[4-(methylcarbamoyl)benzyl]-2,3-dihydro-1H,1'H-2,2'-biinden-1-yl L-leucinate |
| 38 | (1R,2R)-2-[4-(dimethylcarbamoyl)benzyl]-2,3-dihydro-1H,1'H-2,2'-biinden-1-yl L-leucinate (38) |
| 39 | methyl 4-(((1S,2S)-1-(((S)-2-amino-4-methylpentanoyl)oxy)-2,3-dihydro-1H,1'H-[2,2'-biinden]-2-yl)methyl)benzoate |
| 40 | ethyl 4-(((1S,2S)-1-(((S)-2-amino-4-methylpentanoyl)oxy)-2,3-dihydro-1H,1'H-[2,2'-biinden]-2-yl)methyl)benzoate |
| 41 | propyl 4-(((1S,2S)-1-(((S)-2-amino-4-methylpentanoyl)oxy)-2,3-dihydro-1H,1'H-[2,2'-biinden]-2-yl)methyl)benzoate |
| 42 | (1S,2S)-2-(4-carbamoylbenzyl)-2,3-dihydro-1H,1'H-2,2'-biinden-1-yl L-leucinate |
| 43 | (1S,2S)-2-{4-[(2-Hydroxyethyl)carbamoyl]benzyl}-2,3-dihydro-1H,1'H-2,2'-biinden-1-yl leucinate |
| 44 | (1S,2S)-2-[4-(methylcarbamoyl)benzyl]-2,3-dihydro-1H,1'H-2,2'-biinden-1-yl L-leucinate |
| 45 | (1S,2S)-2-[4-(dimethylcarbamoyl)benzyl]-2,3-dihydro-1H,1'H-2,2'-biinden-1-yl L-leucinate |
| 46 | 2-hydroxy-5-(4-(((1R,2R)-1-hydroxy-2,3-dihydro-1H,1'H-[2,2'-biinden]-2-yl)methyl)benzamido)benzoic acid |
| 47 | 2-hydroxy-5-(4-(((1S,2S)-1-hydroxy-2,3-dihydro-1H,1'H-[2,2'-biinden]-2-yl)methyl)benzamido)benzoic acid |

The invention also provides a compound of the formula:

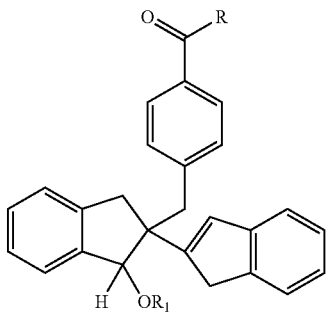

This compound compromises two diastereoisomers

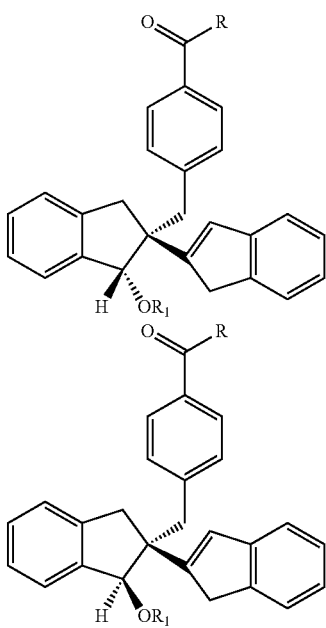

The preferred isomer is

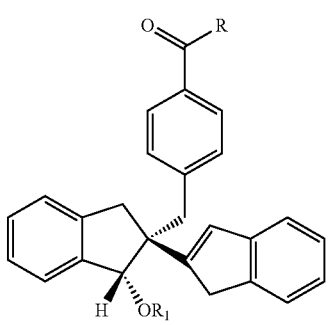

The invention further provides a pharmaceutical composition comprising any of the compounds described above.

The active compound may be present in the medicament for use in man at a suitable dose to achieve the desired effect. For example, the final dose may be between 0.1 and 10 mg/kg.

It may be possible to administer the compounds of the invention in the form of a bulk active chemical. It is however, preferred that the compounds be administered in the form of a pharmaceutical formulation or composition. Such formulations may comprise one or more pharmaceutically acceptable excipient, carrier or diluent.

The compounds of the invention may be administered in a number of different ways. The compounds may be administered orally. Preferred pharmaceutical formulations for oral administration include tablets, capsules, caplets, solutions, suspensions or syrups.

The pharmaceutical formulations may be provided in a form for modified release such as a time release capsule or tablet.

The medicament may be administered orally, parenterally, intranasally, transcutaneously or by inhalation.

The invention also provides a method for the prophylaxis or treatment of inflammatory bowel disease, comprising administering to a subject an effective amount of a compound of the invention.

The invention further provides a method for the prophylaxis or treatment of ulcerative colitis, comprising administering to a subject an effective amount of a compound of the invention.

Also provided is a method for the prophylaxis or treatment of Crohn's disease, comprising administering to a subject an effective amount of a compound of the invention.

As described herein, compounds of the invention may optionally be substituted with one or more substituents, such as are illustrated generally above, or as exemplified by particular classes, subclasses, and species of the invention. In general, the term substituted refers to the replacement of hydrogen atoms in a given structure with a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The present invention is described in terms known and appreciated by those skilled in the art. For ease of reference certain terms hereinafter are defined to clarify, but not limit, the terms defined.

The term alkyl refers to a straight or branched chain hydrocarbon, preferably having from one to ten carbon atoms. Exemplary alkyl groups are methyl, ethyl, propyl, isopropyl, isobutyl, n-butyl, tert-butyl, isopentyl, n-pentyl, and the like.

The term unsaturated means that a moiety has one or more units of unsaturation.

The term cycloalkyl refers to a non-aromatic cyclic hydrocarbon ring. Exemplary cycloalkyl groups include, but are not limited to, cyclopropyl, cyclobutyl, cyclopentyl, cyclohexyl, and cycloheptyl. The term "cycloalkyl" includes a fused ring system where, for example, a cycloalkyl ring is fused with an aromatic ring.

The term aryl used alone or as part of a larger moiety refers to monocyclic or polycyclic ring systems having a total of five to fourteen ring members, wherein at least one ring in the system is aromatic and wherein each ring in the system contains 3 to 7 ring members. In particular the term aryl refers to a benzene ring or to a fused benzene ring system, such as anthracene, phenanthrene, or naphthalene ring systems. Examples of aryl groups include phenyl, 2-naphthyl, 1-naphthyl, and the like.

The term alkoxy refers to a group —OX, where X is alkyl, as herein defined.

The term aryloxy alone or as part of another group includes any of the above aryl groups linked to an oxygen atom.

As used herein alkoxycarbonyl refers to a group —C(O)OX where X is alkyl as defined herein.

The term amino refers to a nitrogen radical substituted with hydrogen, alkyl, aryl, or combinations thereof. Examples of amino groups include —NHMethyl, —NH$_2$, —N(Methyl)2, —NPhenylMethyl, —NHPhenyl, —NEthylMethyl, and the like. An "alkylamino" refers to a nitrogen radical substituted with at least one alkyl group. Examples of alkylamino groups include —NHMethyl, —N(Methyl)2, —NPropylMethyl, —NHButyl, —NEthylMethyl, —NPhenylMethyl, and the like. An "arylamino" refers to a nitrogen atom substituted with at least one aryl group.

The term "halogen" refers to fluorine, chlorine, bromine, or iodine.

The term "hydroxyl" refers to a group —OH.

The term "thiol" refers to a group —SH.

The compounds of the invention may crystallize in more than one form. This characteristic is referred to as polymorphism, and such polymorphic forms ("polymorphs") are within the scope of the invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein are capable of existing as stereoisomers. The scope of the present invention includes mixtures of stereoisomers as well as purified or enriched mixtures. Also included within the scope of the invention are the individual isomers of the compounds of the invention as well as any wholly or partially equilibrated mixtures thereof. Certain compounds of the invention contain one or more chiral centers. Therefore the present invention includes racemates, purified enantiomers, and enantiomerically enriched mixtures of the compounds of the invention. The compounds of the present invention include racemic and chiral indane dimers.

Preferably the salts of the present invention are pharmaceutically acceptable salts. Salts encompassed within the term pharmaceutically acceptable salts refer to non-toxic salts of the compounds of this invention. Salts of the compounds of the present invention may comprise acid addition salts.

Solvate refers to a complex of variable stoichiometry formed by a solute (in this invention, a compound of the invention, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

Prodrug refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For oral administration in the form of a tablet or capsule, the active drug component can be combined with an oral, non-toxic pharmaceutically acceptable inert carrier such as ethanol, glycerol, water, and the like. Powders may be prepared by comminuting the compound to a suitable fine size and mixing with an appropriate pharmaceutical carrier such as an edible carbohydrate such as starch or mannitol. Flavorings, preservatives, dispersing agents, and coloring agents and the like may also be included.

Capsules may made by preparing a powder, liquid, or suspension mixture and encapsulating within gelatin or other suitable shell material. Lubricants such as colloidal silica, talc, magnesium stearate, calcium stearate, or solid polyethylene glycol may be added to the mixture. A disintegrating or solubilizing agent such as calcium carbonate or sodium carbonate can also be added to improve the availability of the medicament when the capsule is ingested. Other agents such as binders, lubricants, disintegrating agents, and coloring agents can also be incorporated into the mixture. Examples of suitable binders include starch, gelatin, natural sugars, corn sweeteners, natural and synthetic gums, tragacanth, or sodium alginate, carboxymethylcellulose, polyethylene glycol and the like. Suitable lubricants for these dosage forms include, for example, sodium oleate, sodium stearate, magnesium stearate, sodium benzoate, sodium acetate, sodium chloride, and the like. Suitable disintegrators include, without limitation, starch, methyl cellulose, agar, bentonite, xanthan gum, and the like.

Tablets may be formulated by preparing a powder mixture, granulating the mixture, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or the like. The powder mixture can be wet-granulated with a binder such as syrup, starch paste, or solutions of cellulosic or polymeric materials, and pressing through a screen.

The compounds of the present invention can also be combined with a free flowing inert carrier and compressed into tablets directly without going through other steps such as granulating. A clear or opaque protective coating consisting of a sealing coat of a suitable material such as shellac, sugar or polymeric material, and a polish coating for example of wax can be provided. If appropriate colourants be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated by dispersing the compound in a non-toxic vehicle. Solubilisers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in suitable polymers, wax, or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the invention and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include, for example, polyvinylpyrrolidone (PVP). The compounds may also be coupled to a biodegradable polymer achieve controlled release of a drug. Such polymers include polylactic acid, polycyanoacrylates, and block copolymers of hydrogels.

Pharmaceutical formulations adapted for transdermal administration may be presented as discrete patches intended to remain in intimate contact with the skin/epidermis of a patient for a prolonged period of time. For example, the active ingredient may be delivered from the patch by iontophoresis.

Pharmaceutical formulations adapted for topical administration may be formulated as ointments, creams, suspensions, lotions, powders, solutions, pastes, gels, sprays, aerosols, or oils. For treatments of external tissues the formulations may be applied as a topical ointment or cream.

For topical administration in the mouth the formulation may include lozenges, pastilles, and mouthwashes.

For nasal administration, a powder having a particle size for example in the range 20 to 500 microns may be used. The powder may be administered by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of metered dose pressurized aerosols, nebulizers, or insufflators and the like.

For rectal administration the formulation may be presented as suppositories or as enemas.

For vaginal administration the formulation may be in the form of pessaries, tampons, creams, gels, sprays or the like.

For parenteral administration the formulation may be aqueous and non-aqueous sterile injection solutions which may contain various additives such as anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and the like.

The compounds of the present invention and their salts, solvates, and physiologically functional derivatives thereof, may be employed alone or in combination with other therapeutic agents. The compound of the invention and the other pharmaceutically active agent(s) may be administered together or separately. If administered separately, administration may occur simultaneously or sequentially, in any order. The amounts of the compound of the invention and the other pharmaceutically active agent(s) and the relative timings of administration will be selected in order to achieve the desired combined therapeutic effect. The administration in combination of a compound of the invention salts, solvates, or physiologically functional derivatives thereof with other treatment agents may be in combination by administration concomitantly in either a single pharmaceutical composition including both compound or in separate pharmaceutical compositions each including one of the compounds. In some cases the combination of drugs may be administered separately in a sequential manner in which one agent is administered first and a second agent is administered second or the other way around. Such administration may be in a similar time frame or over longer time.

BRIEF DESCRIPTION OF THE DRAWINGS

The invention will be more clearly understood from the following description thereof given by way of example only, in which:—

Figure 10:
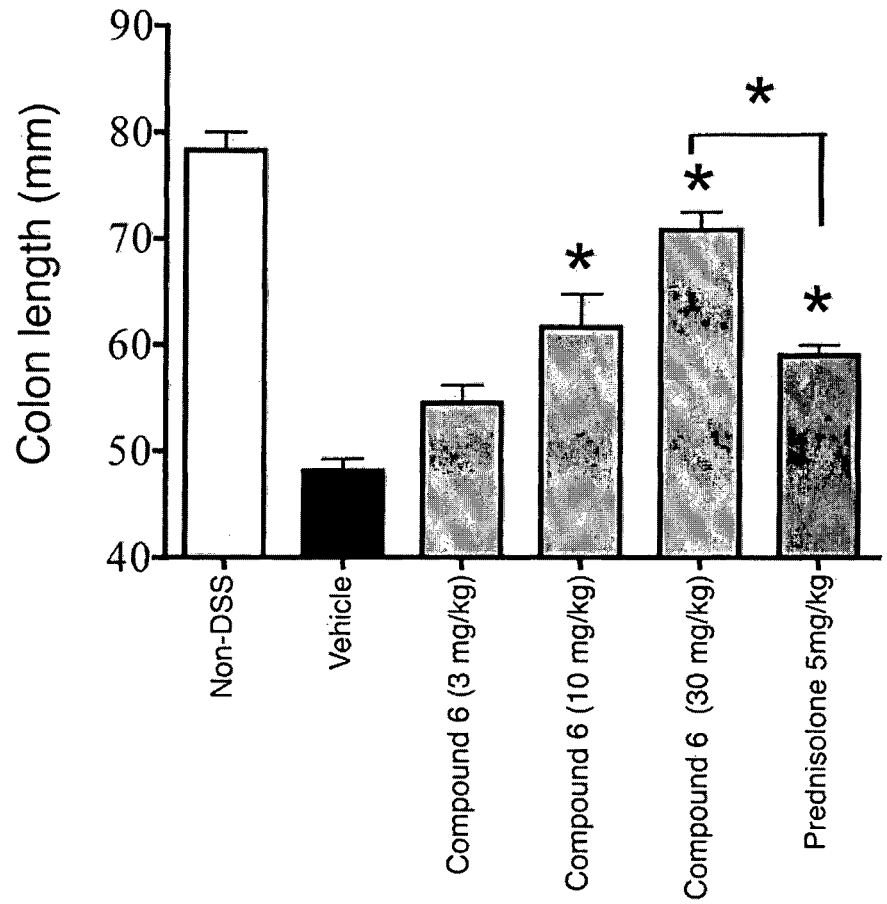
Figure 11:
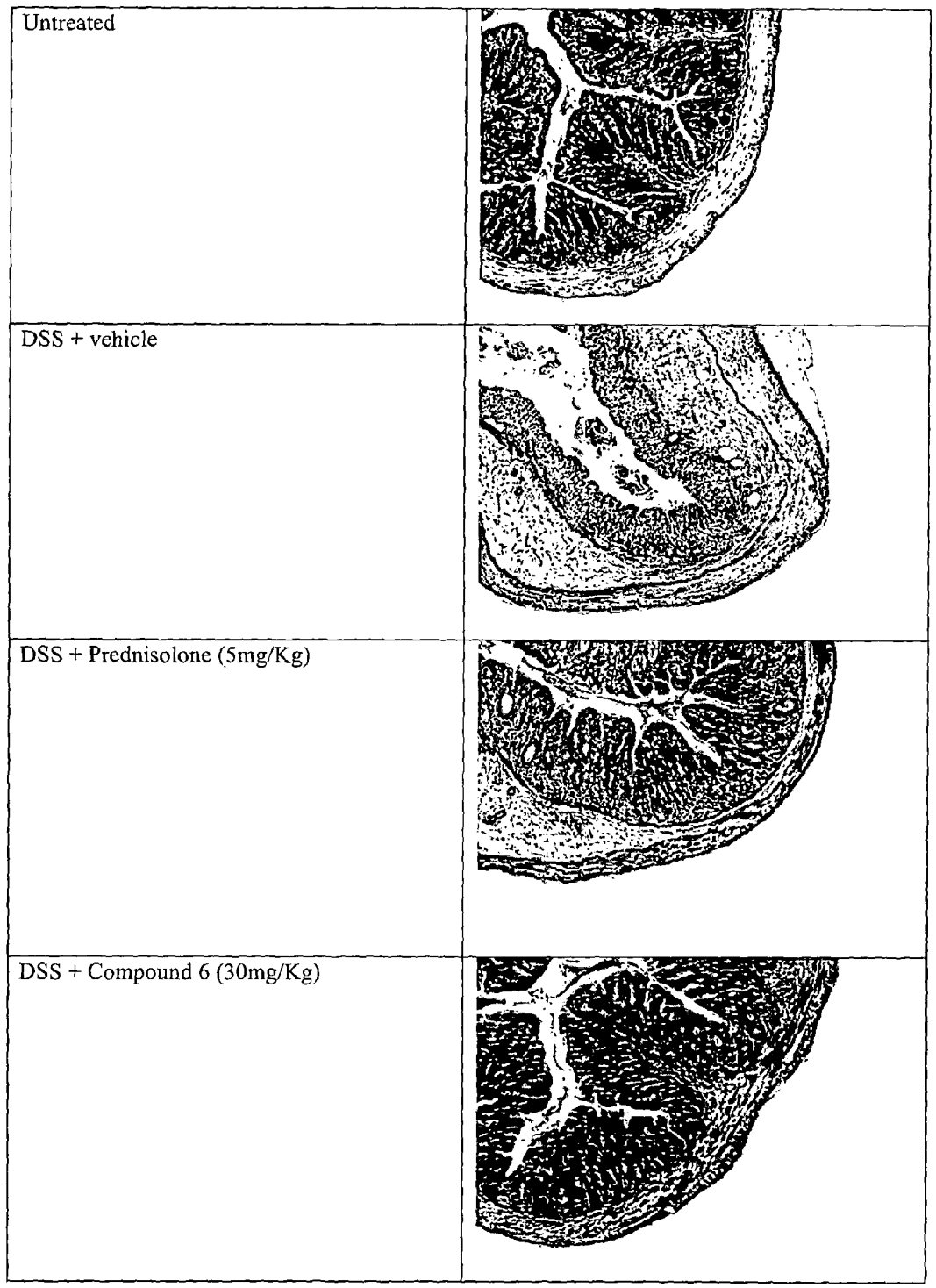
Figure 12:
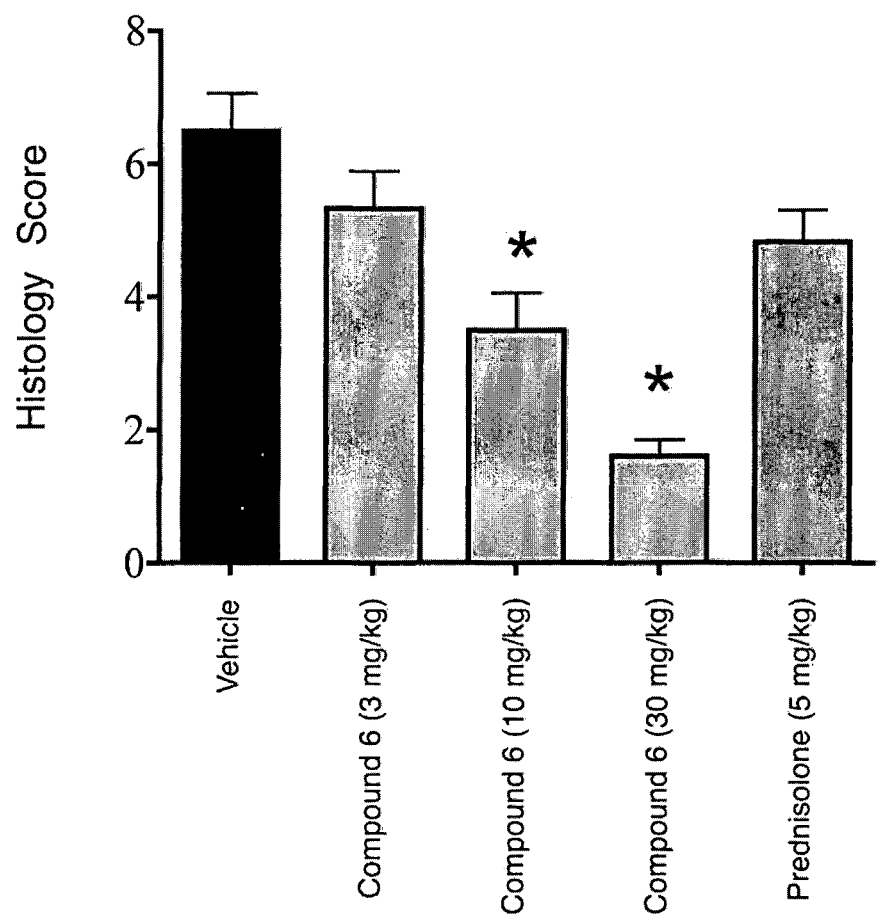
Figure 13:
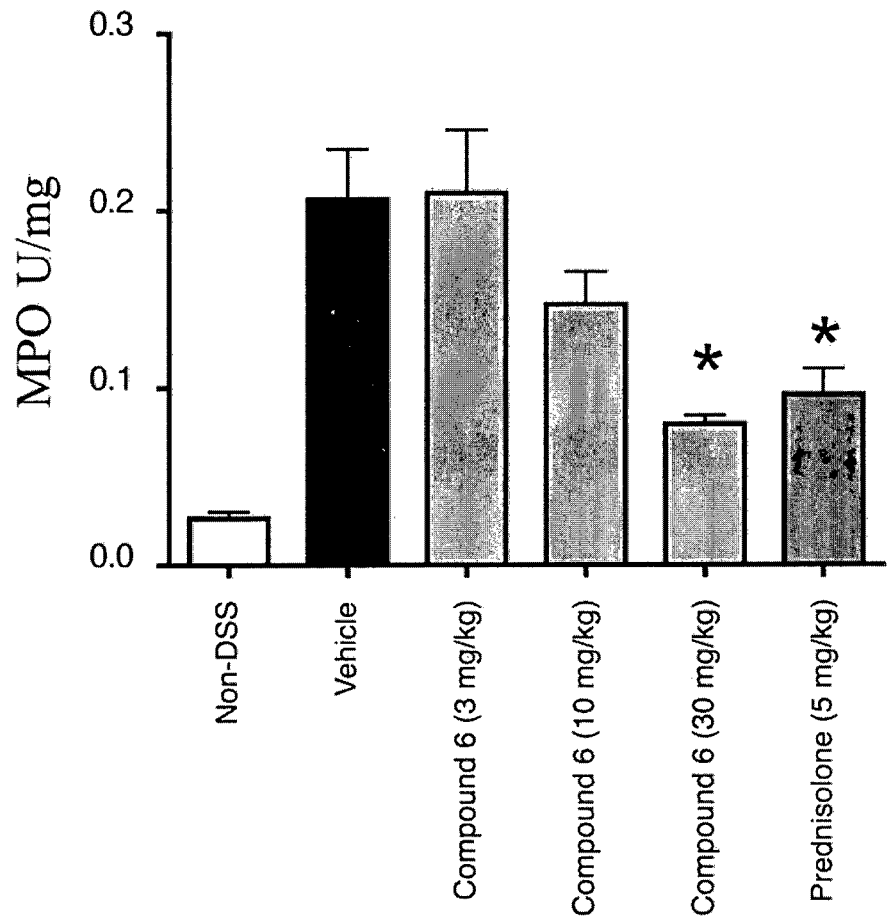
Figure 14:
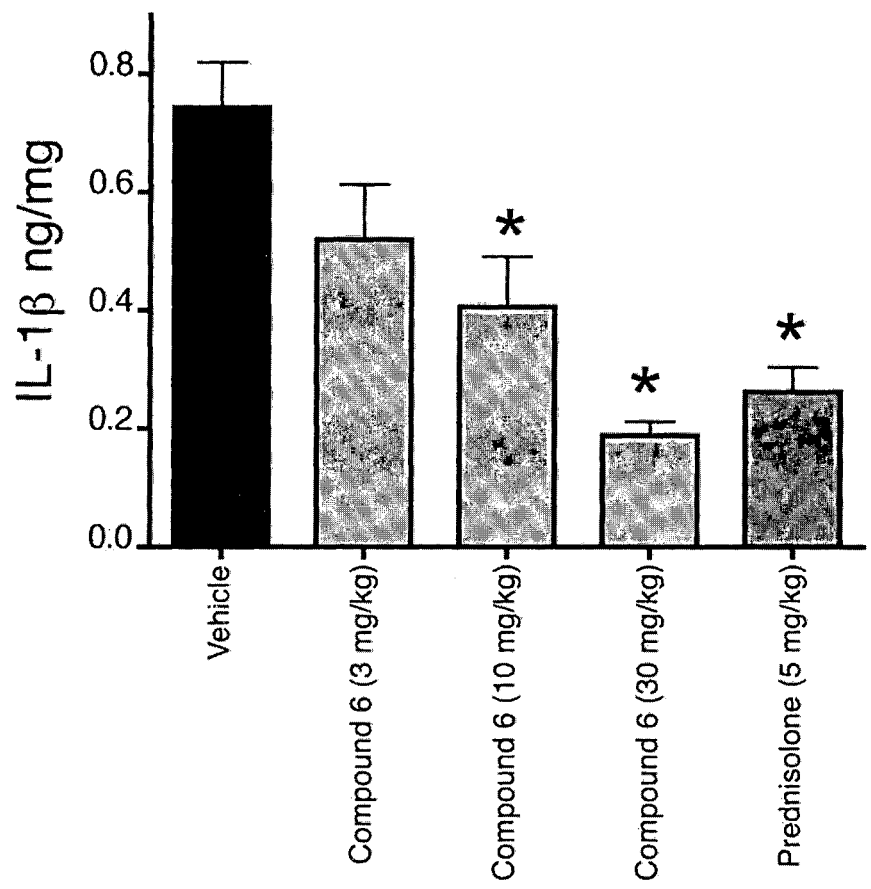
Figure 14:
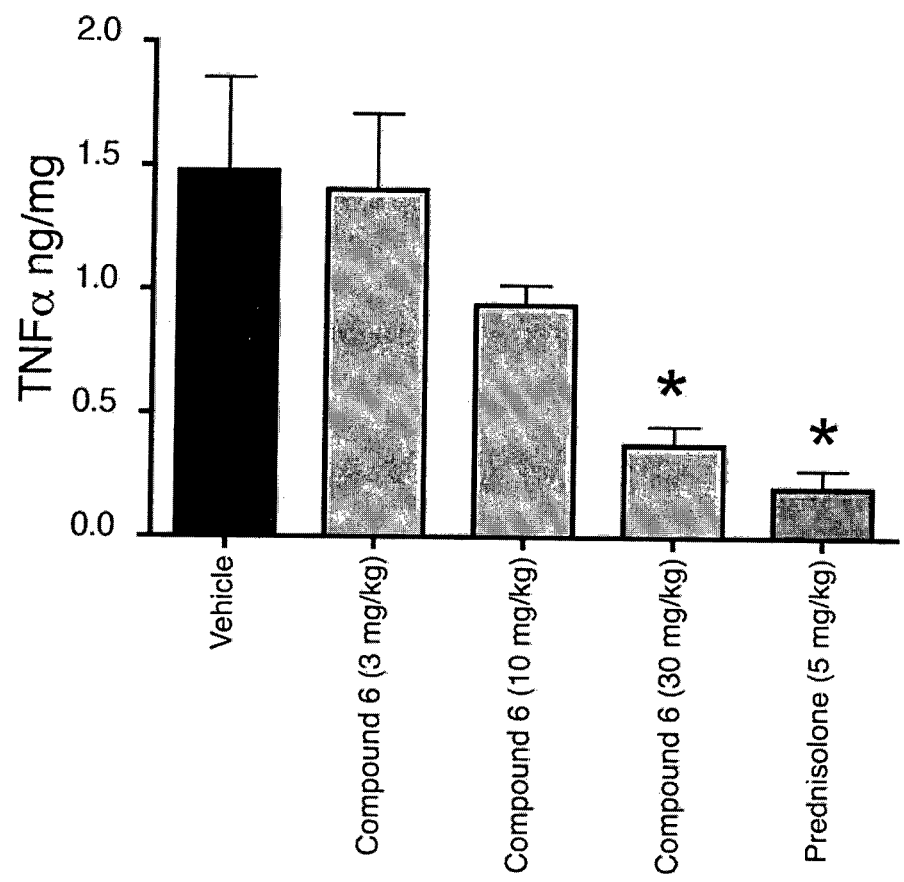
Figure 14:
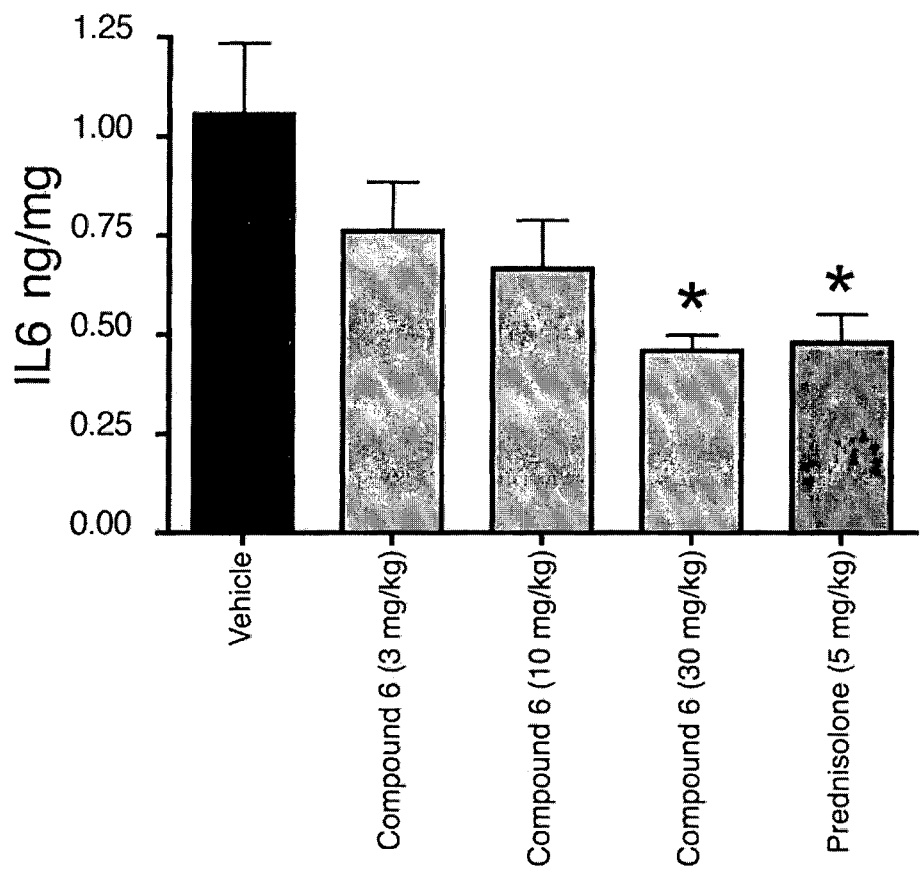
Figure 15:
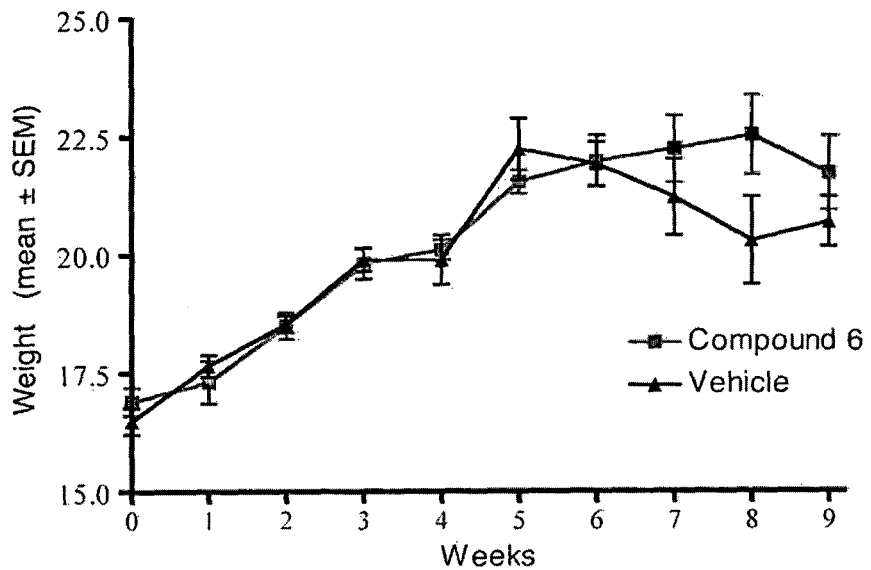
Figure 16:
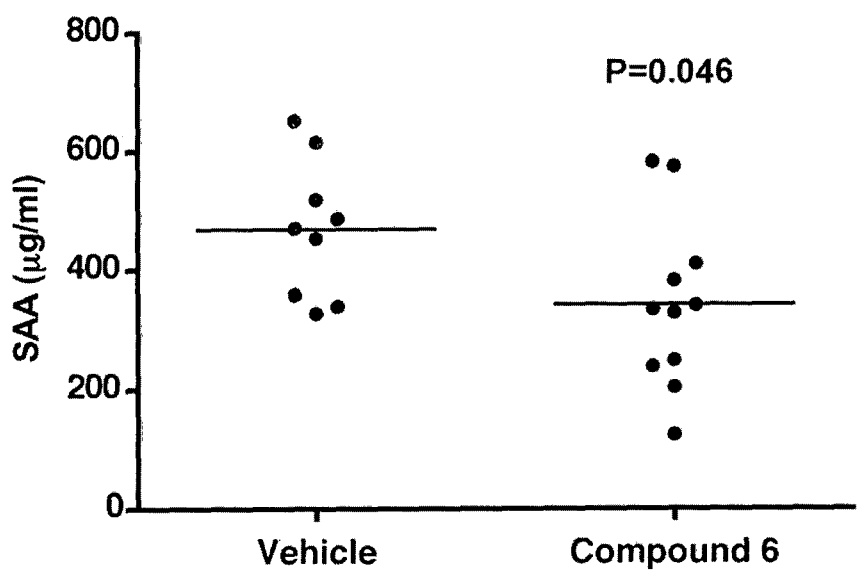
Figure 17:
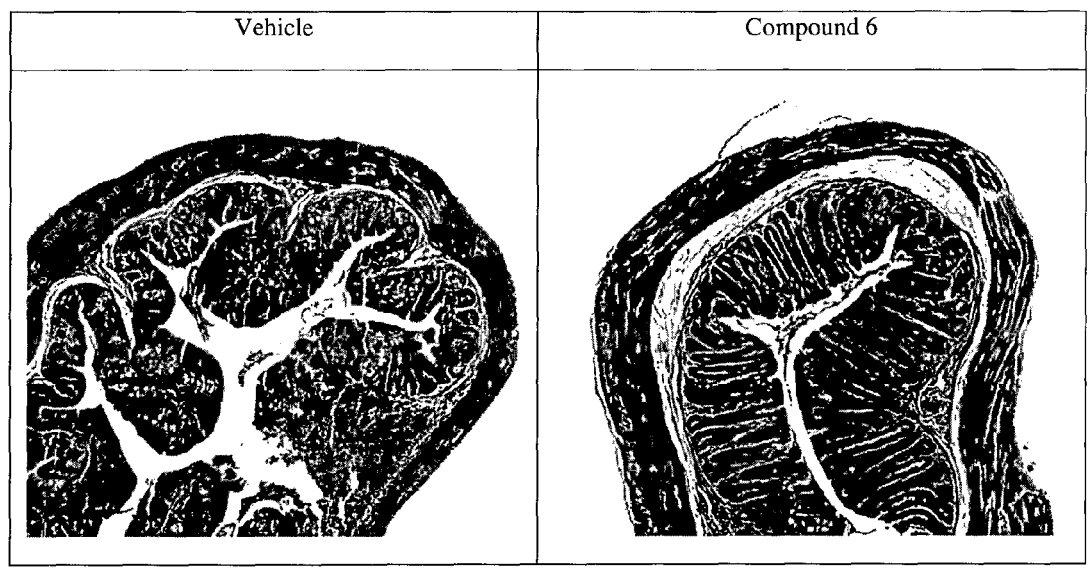
Figure 18:
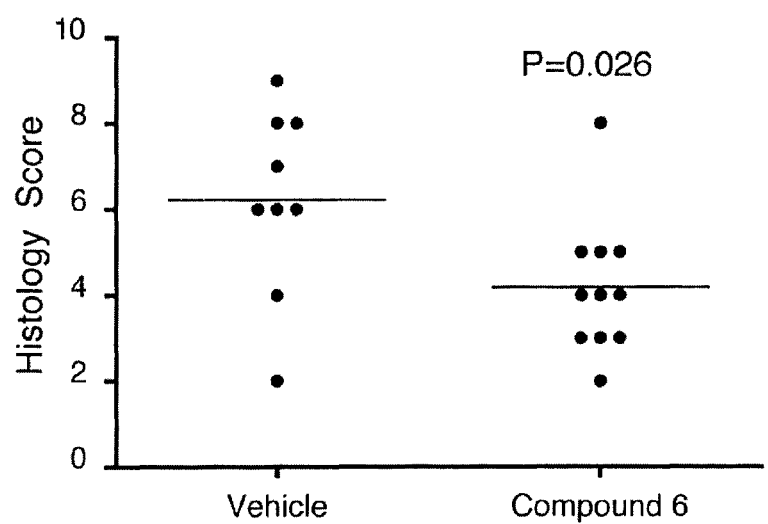
Figure 19:
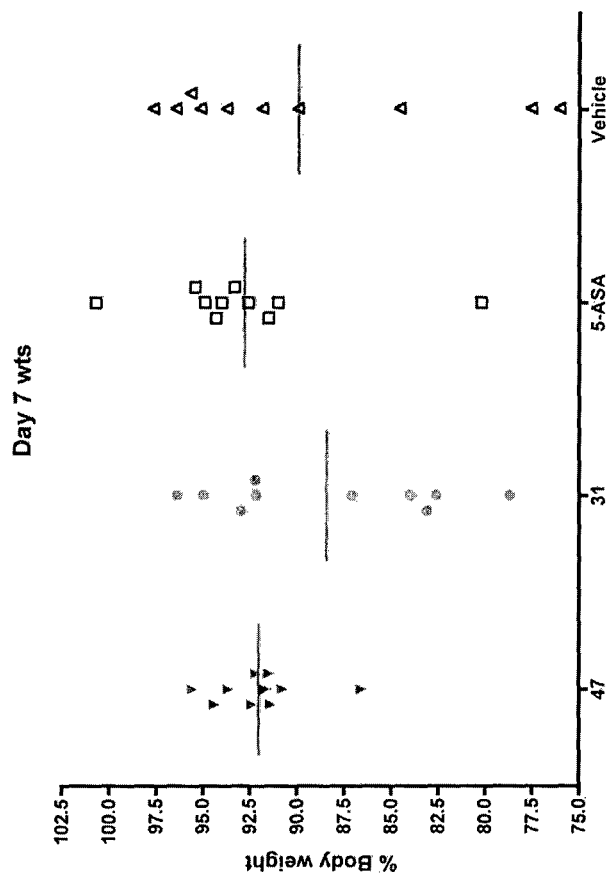
Figure 20:
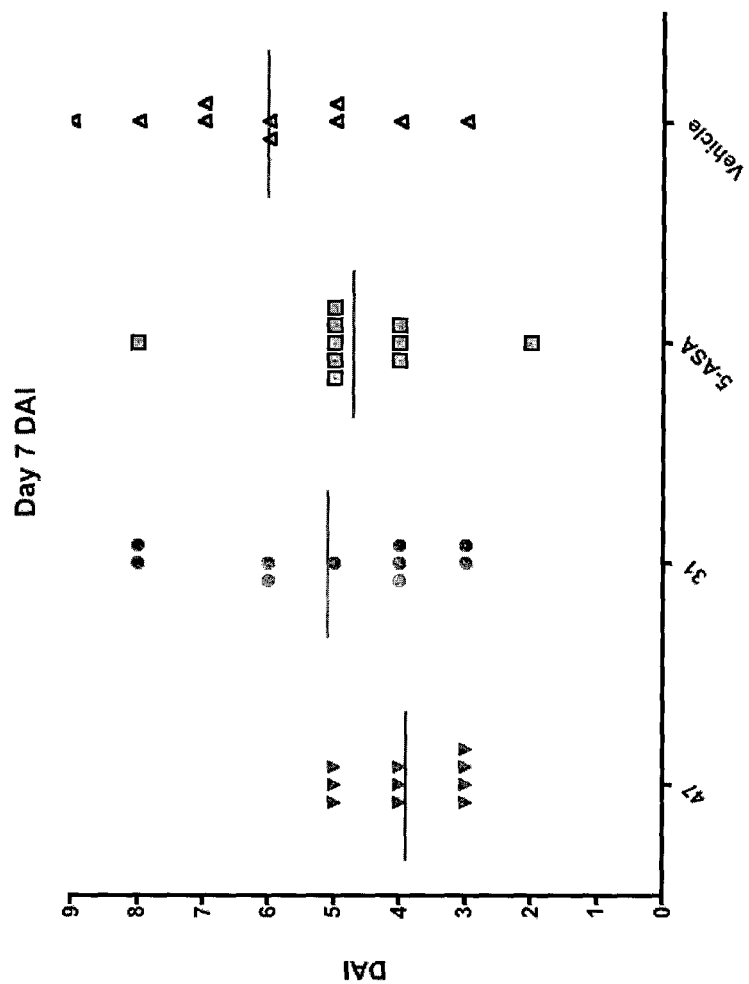
Figure 21:
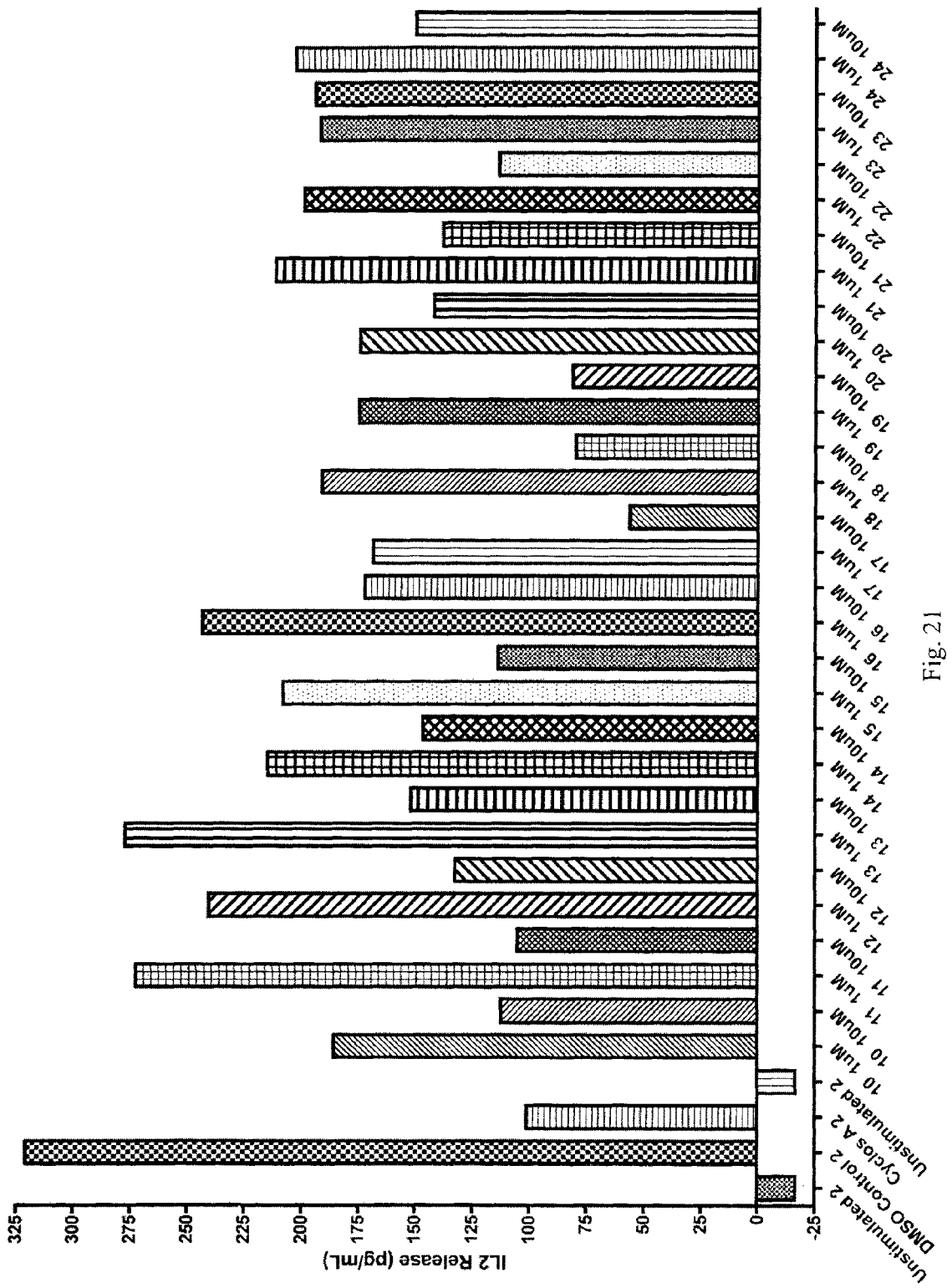
Figure 21:
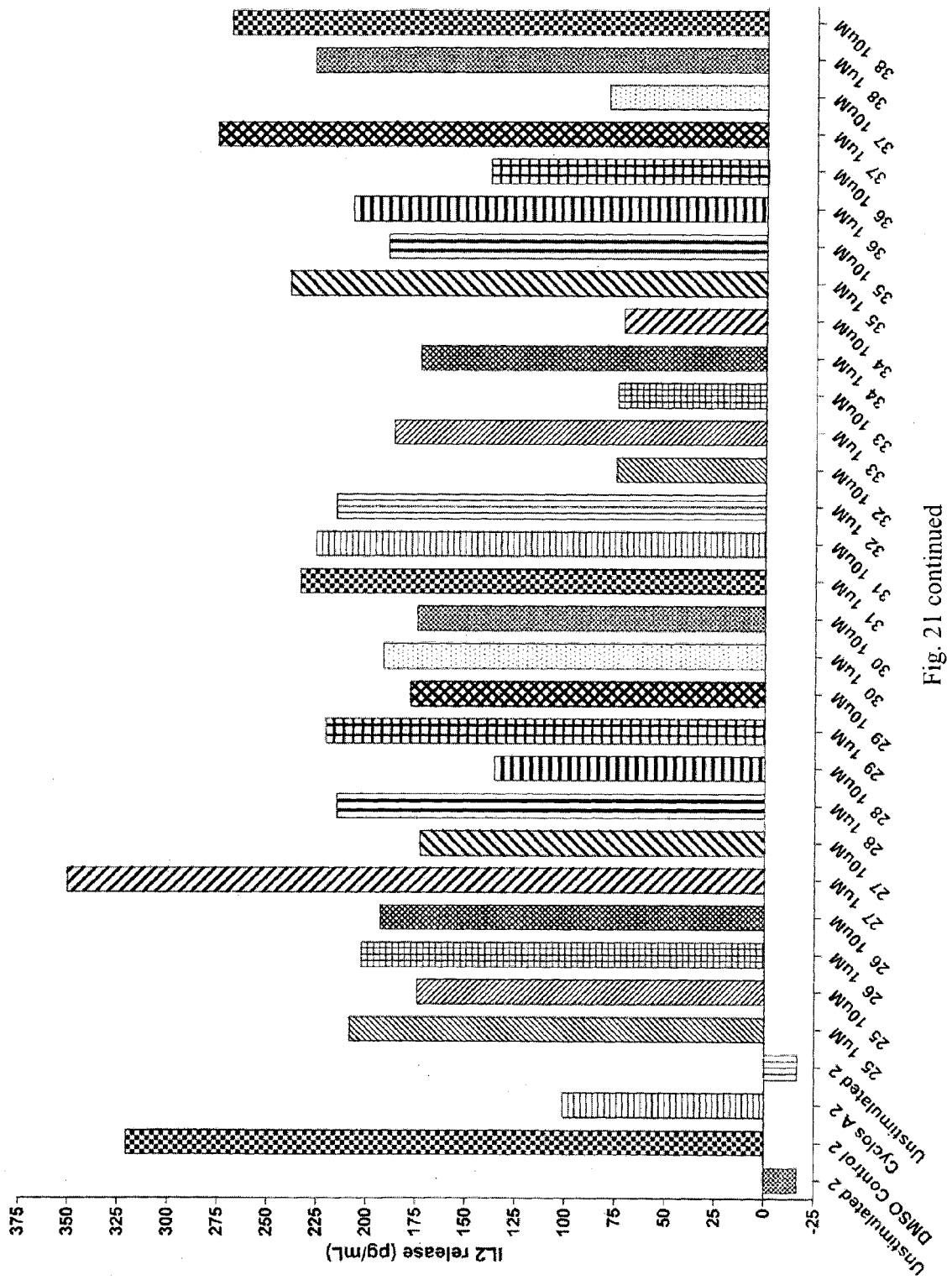
Figure 22:
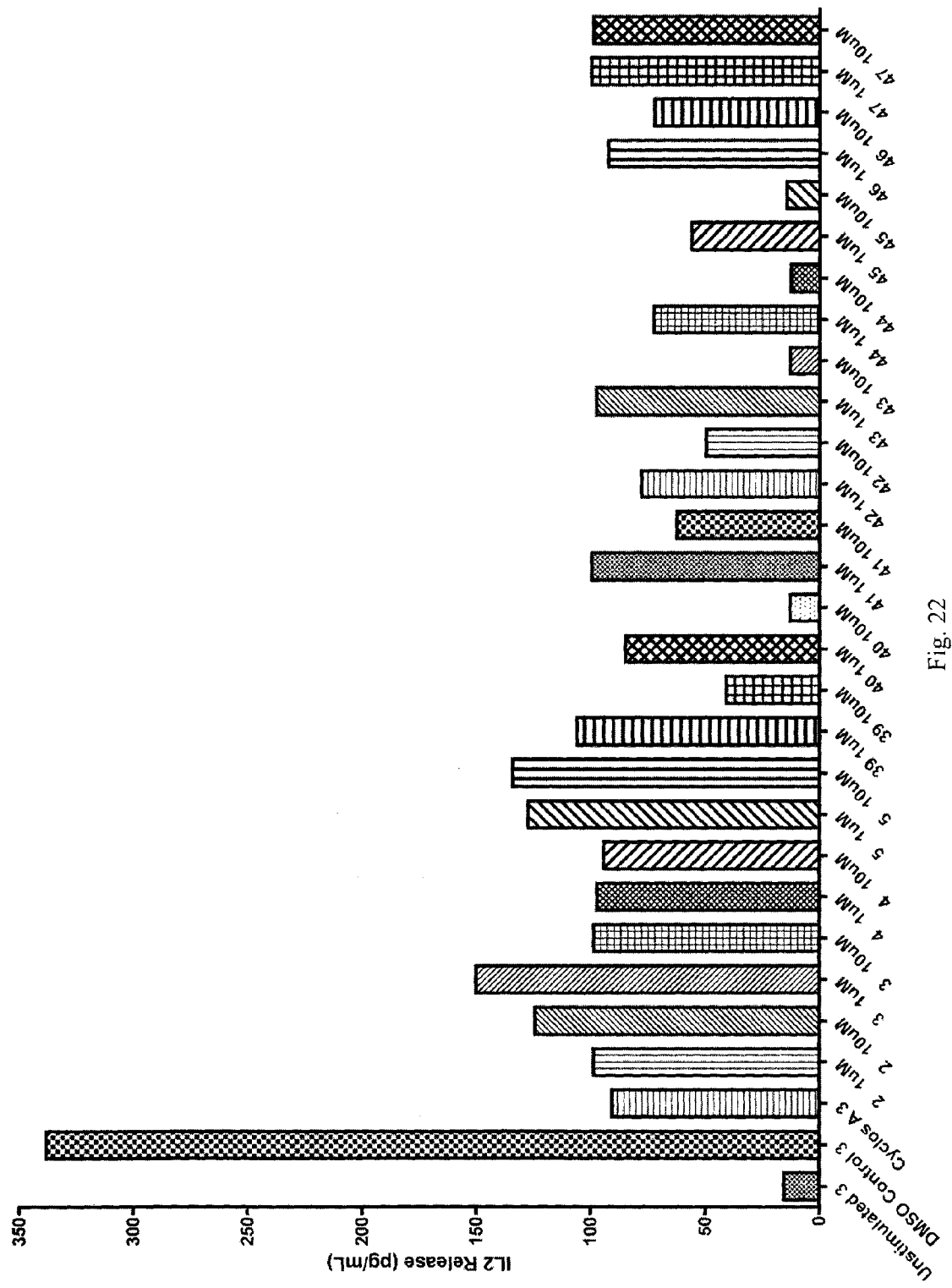

Asterisks indicate a significant (P<0.05) difference (1 way ANOVA) from the vehicle control group;

FIG. 10: Is a bar chart showing the effect of compound 6 on colon length of 5% DSS-treated mice on day 7. Asterisks indicate a significant (P<0.05) difference (1 way ANOVA) from the vehicle control group;

FIG. 11: Shows representative haematoxylin and eosin-stained sections from distal colons of mice. Higher magnifications (×10) are shown;

FIG. 12: Is a bar chart showing the effect of compound 6 on histology scores of colons from DSS-treated mice. Data are Mean±SEM from 5-6 mice. Asterisks indicate a significant (P<0.05) difference (1 way ANOVA) from the vehicle control group. Note, maximum score 10;

FIG. 13: Is a bar chart showing the effect of compound 6 on myeloperoxidase (MPO) activity in the colons of untreated or vehicle, prednisolone and compound 2 treated mice exposed to 5% DSS. Data are Mean±SEM from 5-6 mice. Asterisks indicate a significant (P<0.05) difference (1 way ANOVA) from the vehicle control group;

FIG. 14(A) to (C): Are bar charts showing the effect of compound 6 on Levels of cytokines (IL1β (A), TNFα (B) and IL6 (C)) in mice treated with DSS. Data are Mean±SEM from 5-6 mice. Asterisks indicate a significant (P<0.05) difference (1 way ANOVA) from the vehicle control group;

FIG. 15: Is a group showing weight loss in IL10$^{-/-}$ mice treated with vehicle or compound 6. Mice were administered compound 6 (300 mg/kg/week) or vehicle orally on a Monday/Wednesday/Friday (MWF) dosing schedule. Mice were ~4 weeks of age at start of experiment and were treated for 9 weeks. Mice were weighed weekly and data are presented as Mean±SEM from 9-12 mice per group. Mice were monitored for overt disease, rectal prolapse, and moribund animals were humanely killed;

FIG. 16: Is a scatter graph representing Serum Amyloid A (SAA) levels of individual mice, and Mean (bar), from surviving animals at week 9 (11 and 9 mice in compound 6 or vehicle-treated groups, respectively). Student's t-test was used to test for statistical differences between groups;

FIG. 17: Are representative hematoxylin and eosin-stained sections from distal colons from IL10$^{-/-}$ mice treated for 9 weeks with vehicle or compound 6;

FIG. 18: Histology scores of distal colons of IL10$^{-/-}$ mice treated with vehicle or compound 6. Scatter graph representing histology score of individual mice, and Mean (bar), from surviving animals at week 9 (11 and 9 mice in compound 6 or vehicle-treated groups, respectively). Student's t-test was used to test for statistical differences between groups;

FIG. 19 is a scatter graph showing weight loss in 5% DSS-treated mice at day 7. Data are Mean±SEM from 6-7 mice per group; for compound 31 and 47, in DSS murine colitis (Method 2);

FIG. 20 is a scatter graph showing DAI in 5% DSS-treated mice on day 7. Data are Mean±SEM from 6-7 mice per group; for compound 31 and 47, in DSS murine colitis (Method 2);

FIG. 21 is a bar chart illustrating the effect of compounds 10-16 and 18-38 on IL2 release from Jurkat cells; and FIG. 22 is a bar chart illustrating the effect of compounds 2-5 and 39-47 on IL2 release from Jurkat cells

DETAILED DESCRIPTION OF THE INVENTION

Compound 1 represents a pair of diastereoisomers that result from the reduction and demethylation of the ketone compound A which has a chiral centre at C-2, and is, as a result, a pair of enantiomers.

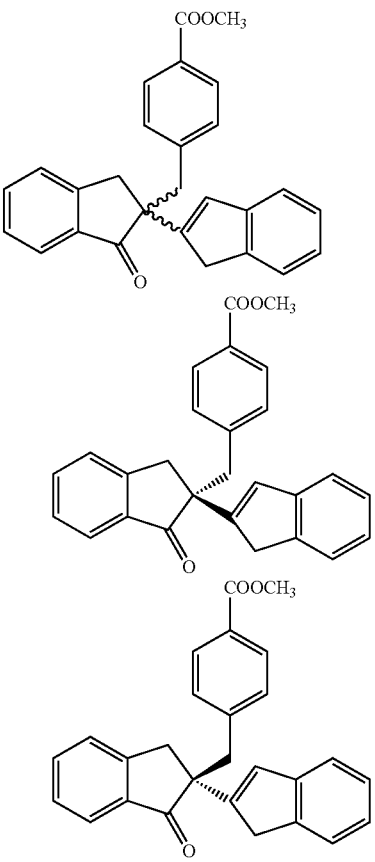

Compound A

Enantiomers of compound A

Reduction of this compound with LiAlH$_4$ yields a compound of the formula

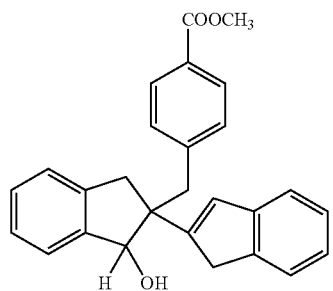 [SMILES: COC(=O)c1ccc(CC2(C3=Cc4ccccc4C3)Cc3ccccc3C2O)cc1]

This compound comprises two diastereoisomers:—

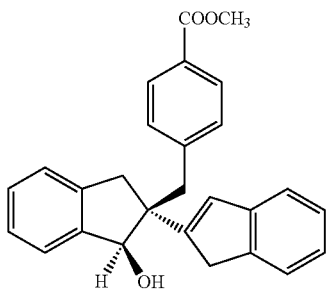

Diastereoisomer B

Diastereoisomer C

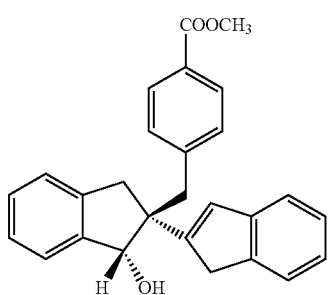

Hydrolysis of Diastereoisomer β gives rise to compounds 2 and 3

Compound 2

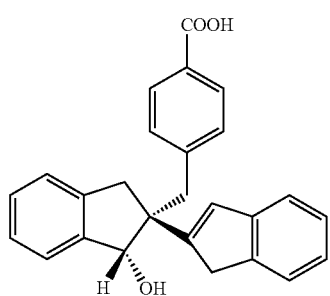

Compound 3

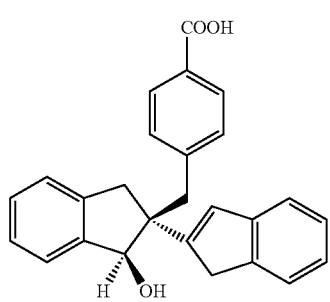

Hydrolysis of Diastereoisomer C gives rise to compounds 4 and 5.

Compound 4

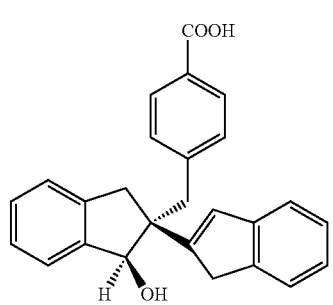

Compound 5

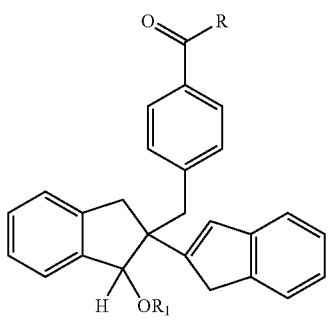

The diastereoisomers can be resolved chemically or chromatographically into their constituent enantiomers.

Figure 1:
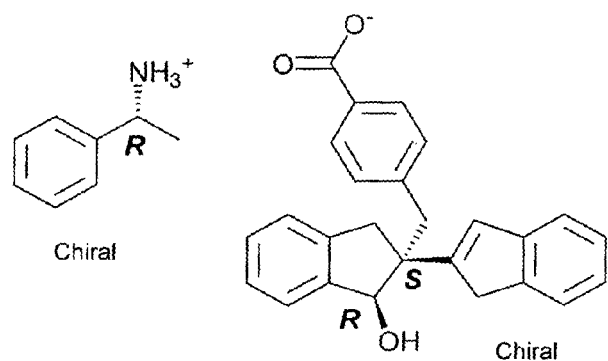
FIG. 1: Is the X-ray crystal structure showing the absolute stereochemistry for the enantiomer compound 4 (R)-(+)-methylbenzylamine salt (compound 9)
Figure 1:
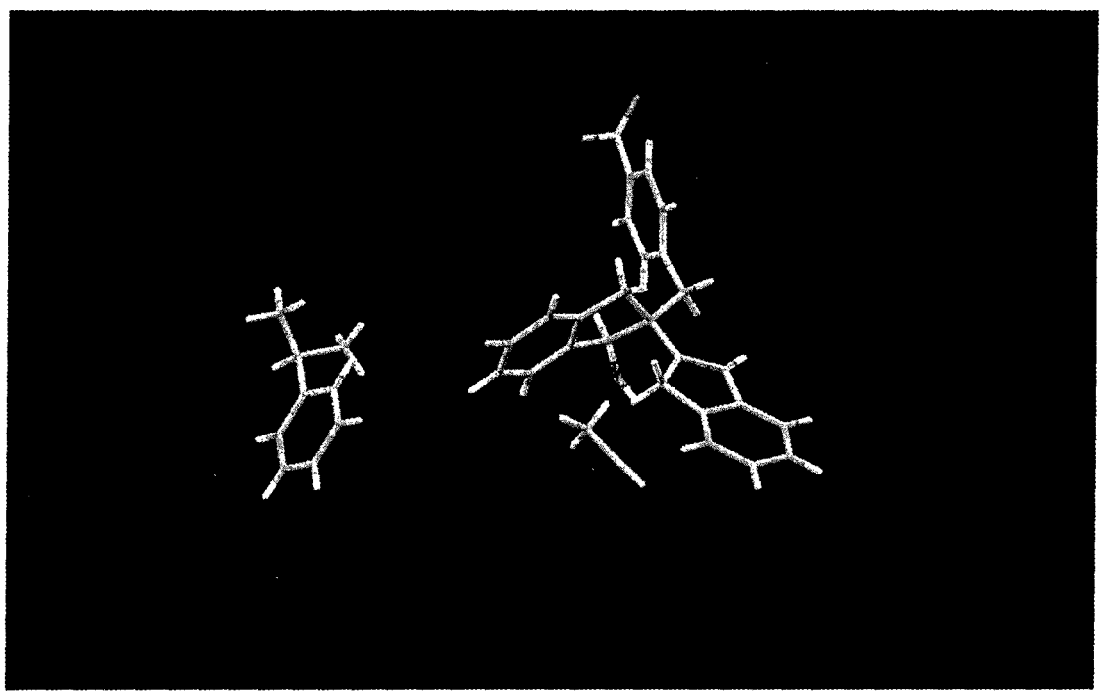

The absolute stereochemistry of compound 4 has been established by single crystal X-ray of compound 4 (R)-(+)-methylbenzylamine salt (compound 9) (FIG. 1).

Figure 2:
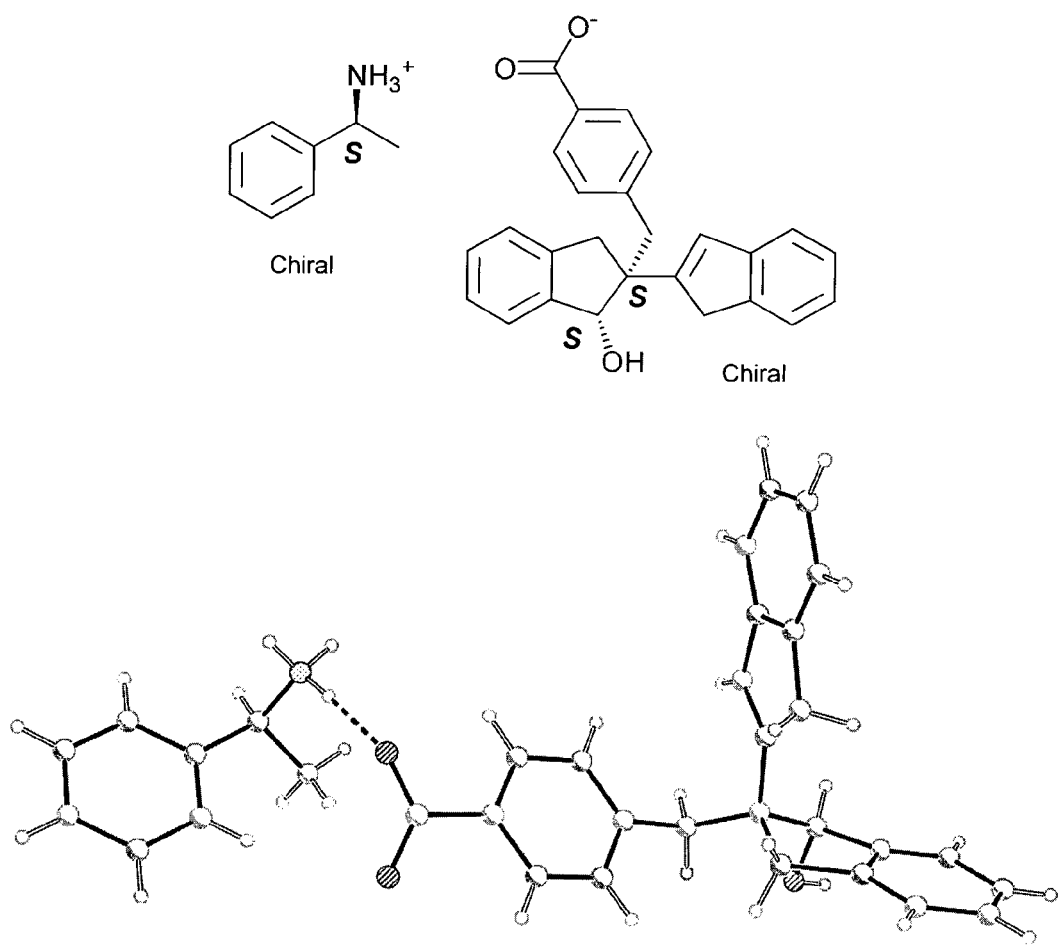
FIG. 2: Is the X-ray crystal structure showing the absolute stereochemistry for the enantiomer compound 2 (S)-(–)-methylbenzylamine salt (compound 8)
Figure 2A:
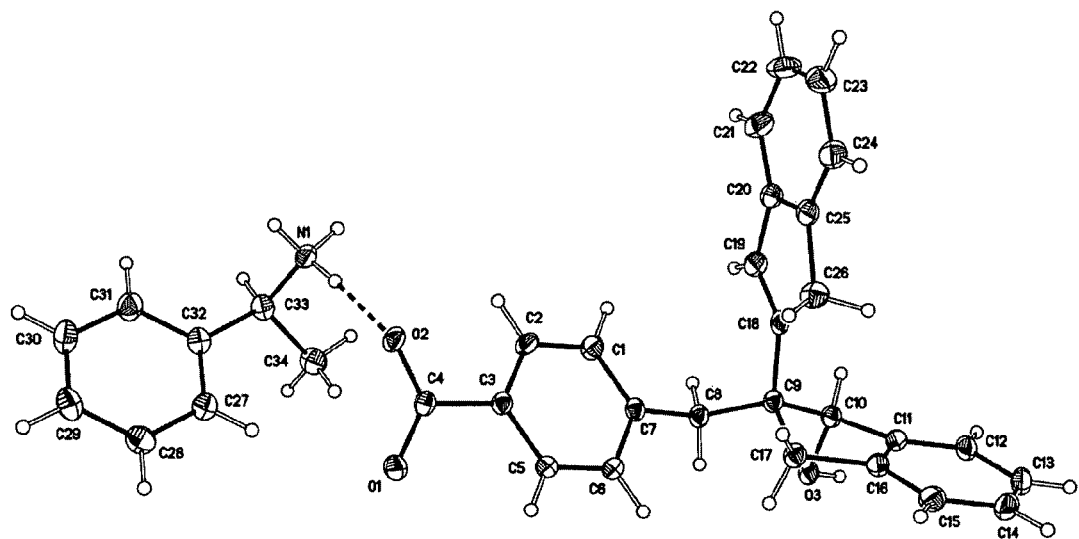
FIG. 2A: Is a view of a molecule of compound 8 from the crystal structure showing the numbering scheme employed. Anisotropic atomic displacement ellipsoids for the non-hydrogen atoms are shown at the 50% probability level. Hydrogen atoms are displayed with an arbitrarily small radius. Only the major disorder component is shown.

The absolute stereochemistry of compound 2 was confirmed by single crystal X-ray of compound 2 (S)-(−)-methylbenzylamine salt (compound 8) (FIGS. 2 and 2A).

The invention also relates to compounds of the formula:

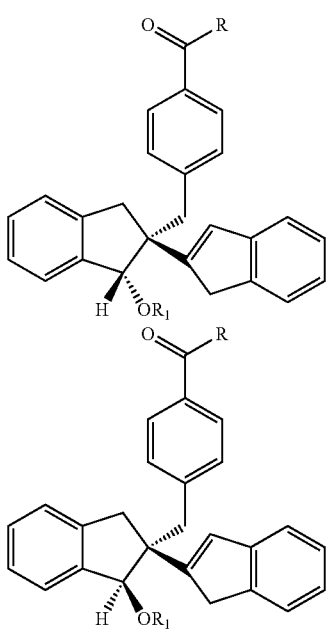

These compounds compromises two diastereoisomers

The preferred diastereoisomer with the following relative stereochemistry is presented below

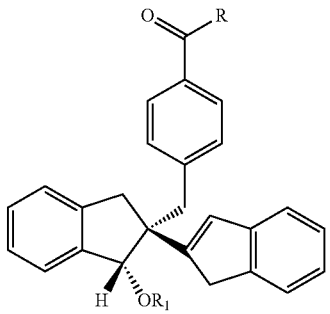

This diastereoisomer is composed of two enantiomers. The absolute stereochemistry of the preferred enantiomer is presented below

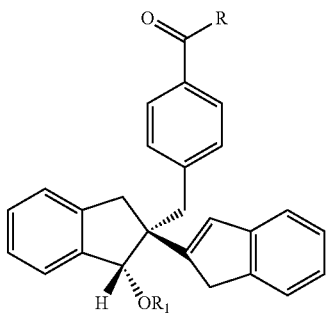

General Reaction Procedures

General synthetic procedures for the coupling of enantiomeric mixtures as exemplified below are described in WO9720806A, the entire contents of which are herein incorporated by reference.

General Preparation of Acid Derivative Compound A

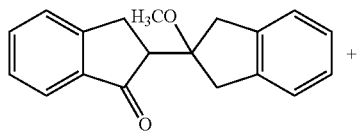

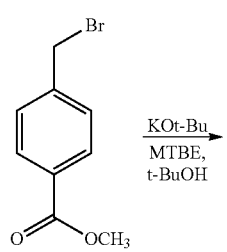

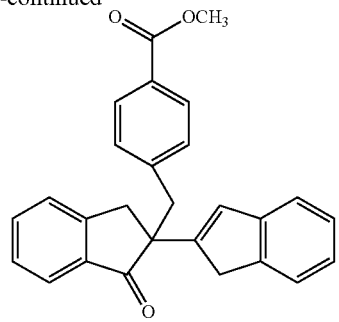

To a stirred solution of the coupled product (4 mmol, 1.00 g) in tert-butanol (5 mL) and diethyl ether (30 mL) under nitrogen was added methyl (4-bromomethyl)benzoate (6 mmol, 1.41 g). To this was added a solution of potassium tert-butoxide in tert-butanol (30 mL) and diethyl ether (5 mL), slowly dropwise. With each drop, the mixture turned a yellow colour and then it reverted its original grey colour. The mixture was stirred for a further 3 hours until the TLC (80:20, hexane:ethyl acetate) showed no more starting material. The reaction was quenched by the addition of sat. $NH_4Cl$. The layers were separated and the aqueous layer extracted with diethyl ether (2×120 mL). The combined organic layers were washed with water, brine, dried over $MgSO_4$ and evaporated. The solid product precipitated from the crude on removal of most of the solvent. This was filtered off and washed with cold diethyl ether to give 0.98 g (62%) of a cream solid.

Reduction of Methyl Benzoate Compound

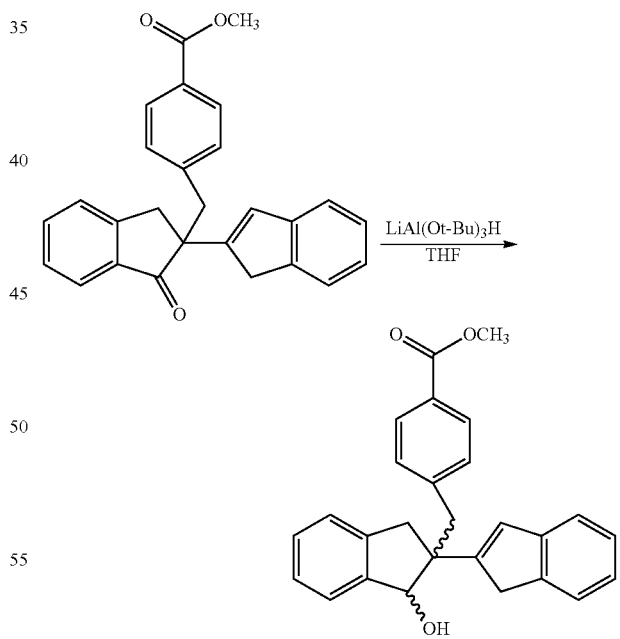

To a stirred solution of the methyl benzoate compound (1.27 mmol, 0.50 g) in THF (15 mL) was added lithium tri-tert-butoxyaluminohydride (1.9 mmol, 0.48 g), slowly portionwise. The reaction was monitored by TLC (80:20, hexane:ethyl acetate) and after 3 h, all of the starting material had been consumed.

The reaction was quenched by pouring onto ice and the crude product extracted into ethyl acetate by stirring the aqueous mixture for 10-15 min with ethyl acetate then pouring into a separatory funnel and allowing it to separate. The combined organic layers were washed with water, brine, dried over MgSO$_4$ and evaporated to give 0.34 g (68%) of a cream-tan solid. The product was isolated as a mixture of two diastereoisomers in an approximately 2:1 ratio.

Analytical Results for the Mixture of Two Diastereoisomers

Purity (HPLC): 94.9% (as a 2:1 ratio of diastereoisomers)

$\delta_H$(300 MHz, CDCl$_3$): 2.77-3.60 (6H, m, 3×CH$_2$), 3.85 (3H, s, CH$_3$), [5.02 (1H, s, CH—OH)] 5.18 (1H, s, CH—OH), [6.23 (1H, s, CH=C)] 6.43 (1H, s, CH=C), 6.90-6.98 (2H, m, Ar—H), 7.11-7.21 (1H, m, Ar—H), 7.22-7.31 (5H, m, Ar—H), 7.36-7.42 (2H, m, Ar—H), 7.78-7.84 (2H, m, Ar—H).

Where possible, the value for the minor diastereoisomer is given in brackets.

$\delta_C$(75.5 MHz, CDCl$_3$): 38.3 (CH$_2$), 38.4 (CH$_2$), 38.6 (CH$_2$), 39.9 (CH$_2$), 40.3 (CH$_2$), 43.4 (CH$_2$), 51.9 (COOCH$_3$), 52.0 (COOCH$_3$), 55.9 (quat. C), 56.3 (quat. C), 82.0 (CH—OH), 82.8 (CH—OH), 120.5 (tert. C), 120.7 (tert. C), 123.5 (tert. C), 123.6 (tert. C), 124.0 (tert. C), 124.2 (tert. C), 124.5 (tert. C), 124.6 (tert. C), 124.8 (tert. C), 124.9 (tert. C), 125.1 (tert. C), 125.2 (tert. C), 126.1 (tert. C), 126.4 (tert. C), 127.0 (quat. C), 127.1 (quat. C), 128.0 (tert. C), 128.2 (tert. C), 128.5 (tert. C), 128.8 (tert. C), 129.0 (tert. C), 129.2 (tert. C), 129.5 (tert. C), 2×130.0 (2×tert. C), 2×130.2 (2×tert. C), 130.7 (tert. C), 140.4 (quat. C), 141.5 (quat. C), 142.8 (quat. C), 143.2 (quat. C), 143.5 (quat. C), 143.6 (quat. C), 143.7 (quat. C), 144.2 (quat. C), 144.3 (quat. C), 144.5 (quat. C), 150.4 (quat. C), 152.6 (quat. C), 167.0 (C=O), 167.2 (C=O).

Hydrolysis of Methyl Benzoate Moiety

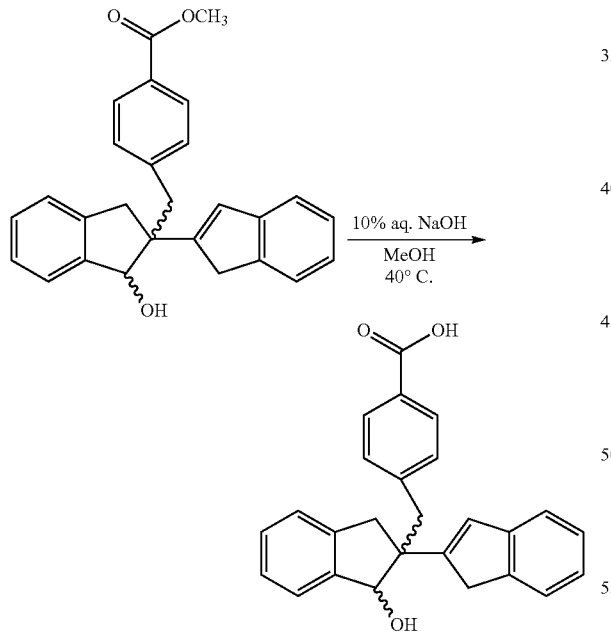

The ester was placed in a round-bottomed flask and 10% aq. NaOH (1 mL) was added to it followed by sufficient methanol to form a solution (6 mL). The solution was heated at 40° C. and monitored by TLC (80:20, hexane:ethyl acetate). After ca. 4 h, no further ester was seen.

The mixture was cooled and sat. NH$_4$Cl added (solution at pH 12). Dilute HCl was added to acidic pH (pH 2). The product was extracted from the cloudy solution into ethyl acetate (3×10 mL). The combined extracts were dried over MgSO$_4$ and evaporated in vacuo to give 0.15 g (quantitative) of a cream solid. The product was isolated as a mixture of two diastereoisomers in an approximately 2:1 ratio.

Analytical Results for the Mixture of Two Diastereoisomers

Purity (HPLC): 95.2% (as a 2:1 ratio of diastereoisomers)

$\delta_H$ (400 MHz, CDCl$_3$): 2.81-3.59 (6H, m, 3×CH$_2$), [5.05 (1H, s, CH—OH)], 5.23 (1H, s, CH—OH), 6.46 (1H, s, CH=C), [6.66 (1H, s, CH=C)], 6.95-7.03 (2H, m, Ar—H), 7.12-7.17 (1H, m, Ar—H), 7.21-7.29 (5H, m, Ar—H), 7.37-7.43 (2H, m, Ar—H), 7.85-7.91 (2H, m, Ar—H).

Where possible, the value for the minor diastereoisomer is given in brackets.

$\delta_C$ (100 MHz, CDCl$_3$): 37.9 (CH$_2$), 38.1 (CH$_2$), 38.2 (CH$_2$), 39.5 (CH$_2$), 39.9 (CH$_2$), 43.1 (CH$_2$), 55.5 (quat. C), 55.9 (quat. C), 81.6 (CH—OH), 82.4 (CH—OH), 120.2 (tert. C), 120.3 (tert. C), 123.1 (tert. C), 123.2 (tert. C), 123.5 (tert. C), 123.9 (tert. C), 124.1 (tert. C), 124.4 (tert. C), 124.5 (tert. C), 124.7 (tert. C), 125.9 (tert. C), 126.0 (tert. C), 126.5 (tert. C), 2×126.7 (quat. C & tert. C), 126.9 (quat. C), 128.1 (tert. C), 128.2 (tert. C), 128.4 (tert. C), 2×129.2 (2×tert. C), 2×129.4 (2×tert. C), 2×129.8 (2×tert. C), 2×129.9 (2×tert. C), 130.4 (tert. C), 140.0 (quat. C), 141.0 (quat. C), 142.3 (quat. C), 142.7 (quat. C), 143.0 (quat. C), 143.2 (quat. C), 143.8 (quat. C), 144.0 (quat. C), 144.1 (quat. C), 144.7 (quat. C), 150.0 (quat. C), 152.0 (quat. C), 170.8 (C=O), 171.1 (C=O).

Chemical Separation of Enantiomers

Preparation of N-BOC D-phenylalanine derivative of methyl benzoate diastereoisomer and/or separation of subsequent diastereoisomers α1 and α2 (or β1 and β2)

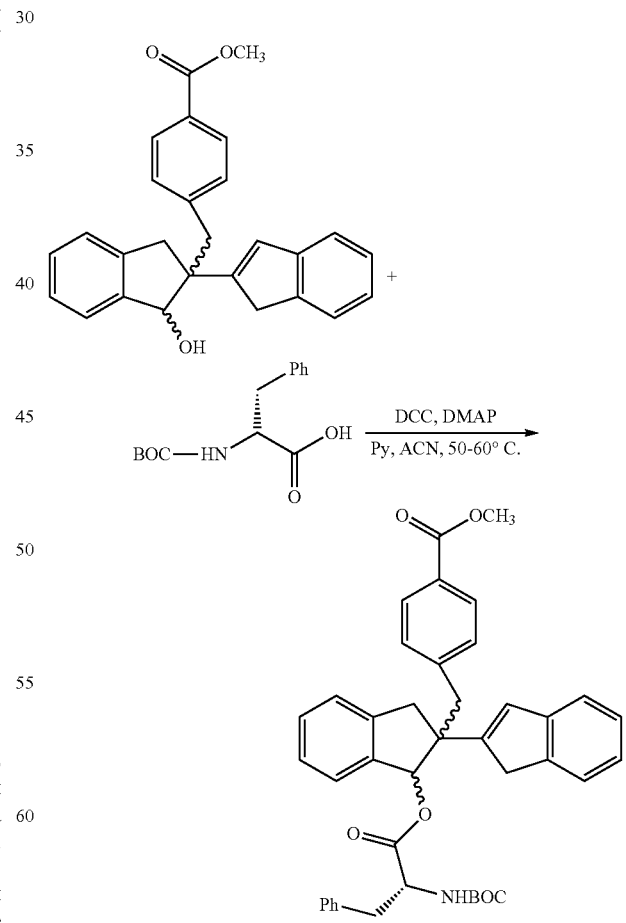

Note: procedure applicable to both diastereoisomers but the example given is for the first diastereoisomer.

Diastereoisomer A (2.5 mmol, 1.0 g) and N-BOC D-phenylalanine (3.1 mmol, 0.8 g) were placed in a round bottom flask fitted with a condenser and suspended in CH₃CN (25 mL) under nitrogen. To this suspension was added pyridine (3.1 mmol, 0.3 mL) followed by a solution of DCC (3.1 mmol, 0.7 g) and DMAP (10% mol, 0.25 mmol, 0.05 g) in CH₃CN (2 mL). The mixture was stirred for 20 h at 50° C., and then allowed to reach room temperature.

The white solid was filtered off and the solvent removed in vacuo. Ethyl acetate was added and the solution obtained was washed with 10% H$_2$SO$_4$, sat. NaHCO$_3$, dried over MgSO$_4$ and evaporated to give 2.1 g of a yellow oil (83% pure by HPLC, yield: quantitative).

The diastereoisomers α1 and α2 were separated by flash chromatography (90 g of silica/g of product) using hexane/MTBE 90:10. From 4.17 g of mixture, 1.3 g of α2, derivative was obtained (as well as 1.71 g of the α1 derivative and 0.3 g as a mixture of both).

Hydrolysis of N-BOC D-phenylalanine Derivative of methyl benzoate Compound (α1, α2, β1 or β2)

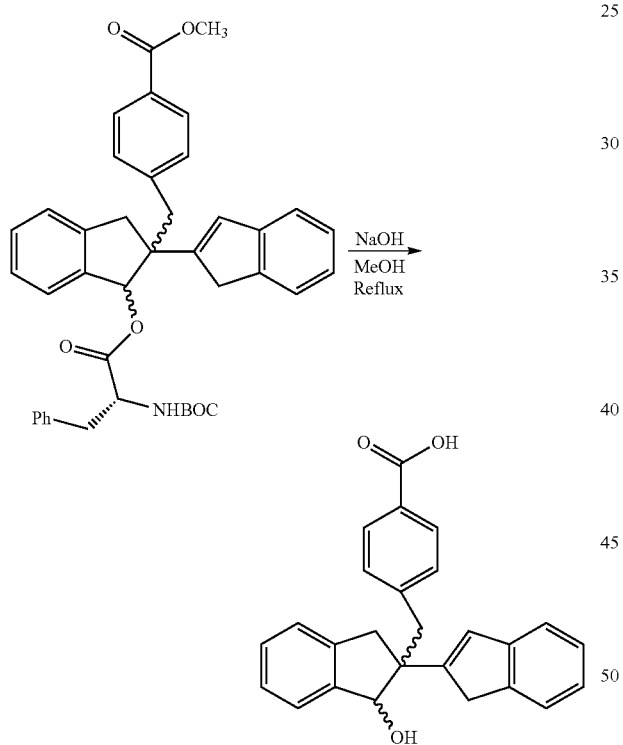

The diastereoisomer α2 (2.3 mmol, 1.45 g) was dissolved in methanol (25 mL) and NaOH (11.5 mmol, 0.45 g) was added and the mixture stirred at reflux temperature and monitored by TLC. After 20 h, the starting material was consumed.

The reaction was cooled to room temperature and quenched by addition of sat. NH$_4$Cl. The methanol was removed in vacuo and the aqueous solution acidified to pH 1 with conc. HCl. The product was extracted with ethyl acetate, dried over MgSO$_4$ and evaporated to give 1.6 g of a yellow gum, which was purified by a short silica column with hexane:MTBE 80:20 as eluent. 0.44 g of acid derivative compound 5 (50% yield) was obtained which was 97.2% pure by HPLC.

Note: An alternative hydrolysis was also carried out using 10% aqueous NaOH in methanol at 40-50° C. This procedure took almost 5 days to go to completion.

Analytical Results for Enantiomers α1, α2, β1, β2

Enantiomer β1 from diastereomer B—Compound 3

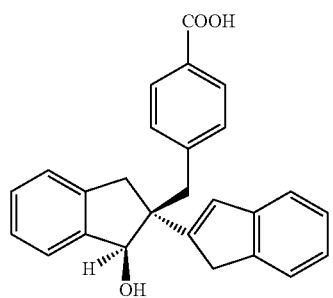 [SMILES: O=C(O)c1ccc(C[C@]2(C3=Cc4ccccc4C3)Cc3ccccc3[C@@H]2O)cc1]

Description: Cream amorphous solid
Melting point 195-196° C.
[α]$_D$: +98.51 (1.07%, MeOH)
Purity: 99.0%
δ$_H$(400 MHz, CDCl$_3$): 2.87 (1H, d, J=13.28 Hz, CH$_2$), 3.00-3.09 (2H, m, CH$_2$), 3.29 (1H, d, J=13.36 Hz, CH$_2$), 3.43-3.61 (2H, m, CH$_2$), 5.27 (1H, s, CH—OH), 6.49 (1H, s, CH═C), 7.00 (2H, d, J=7.88 Hz, Ar—H), 7.16-7.32 (6H, m, Ar—H), 7.44 (2H, d, J=7.24 Hz, Ar—H), 7.90 (2H, d, J=7.92 Hz, Ar—H).

Enantiomer β2 from Diastereoisomer B—Compound 2

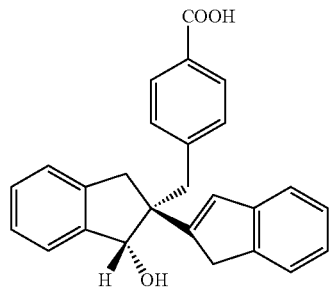 [SMILES: O=C(O)c1ccc(C[C@@]2(C3=Cc4ccccc4C3)Cc3ccccc3[C@H]2O)cc1]

Description: Cream amorphous solid
Melting point 184-185° C.
[α]$_D$: −114.44 (0.18%, MeOH)
Purity: 99.8%
δ$_H$ (400 MHz, CDCl$_3$): 2.87 (1H, d, J=13.32 Hz, CH$_2$), 3.00-3.09 (2H, m, CH$_2$), 3.29 (1H, d, J=13.28 Hz, CH$_2$), 3.46 (1H, d, J=22.64 Hz, CH$_2$), 3.58 (1H, d, J=22.56 Hz, CH$_2$), 5.27 (1H, s, CH—OH), 6.49 (1H, s, CH═C), 7.00 (2H, d, J=8.04 Hz, Ar—H), 7.15-7.34 (6H, m, Ar—H), 7.44 (2H, d, J=7.20 Hz, Ar—H), 7.90 (2H, d, J=8.04 Hz, Ar—H).

Enantiomer α1 from Diastereoisomer C—Compound 4

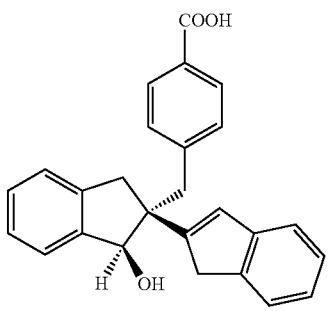 [SMILES: O=C(O)c1ccc(C[C@@]2(C3=Cc4ccccc4C3)Cc3ccccc3[C@@H]2O)cc1]

Description: Cream solid
Melting point 136-140° C.
$[\alpha]_D$: −39.3 (0.66%, MeOH)
Purity: 94.0%
$\delta_H$ (400 MHz, CDCl$_3$): 2.90-3.59 (6H, m, 3×CH$_2$), 5.08 (1H, s, CH—OH), 6.70 (1H, s, CH=C), 7.05 (2H, d, J=8.08 Hz, Ar—H), 7.19 (1H, t, J=7.34 Hz, Ar—H), 7.26-7.47 (7H, 2×m, Ar—H), 7.93 (2H, d, J=8.08 Hz, Ar—H).

Enantiomer α2 from Diastereoisomer C—Compound 5

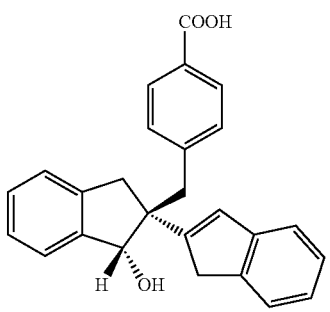 [SMILES: O=C(O)c1ccc(C[C@]2(C3=Cc4ccccc4C3)Cc3ccccc3[C@H]2O)cc1]

Description: Cream amorphous solid
Melting point 195-196° C.
$[\alpha]_D$: +32.1 (1.18%, MeOH)
Purity: 97.2%
$\delta_H$ (400 MHz, CDCl$_3$): 2.94-3.59 (6H, m, 3×CH$_2$), 5.08 (1H, s, CH—OH), 6.70 (1H, s, CH=C), 7.05 (2H, d, J=8.12 Hz, Ar—H), 7.19 (1H, t, J=7.34 Hz, Ar—H), 7.26-7.47 (7H, 2×m, Ar—H), 7.93 (2H, d, J=8.12 Hz, Ar—H).

HPLC Method

Achiral and Chiral HPLC methods were established for the qualitative and quantitative separation of enantiomers compounds 2, 3, 4, 5.

HPLC Resolution of Enantiomers

| Reverse phase method | |
|---|---|
| Column | Hypersil BDS C18, 5μ, 250 × 4.6 mm |
| | Phenomenex Luna C18, 5μ, 250 × 4.6 mm, N: 32 |
| Wavelength | 210 nm |
| Flow rate | 1 mL/min (for ketone and esters) |
| | 0.6 mL/min (for acids and salts) |
| Mobile phase | 70:30 CH$_3$CN:0.1% aq. Acetic acid |
| Sample | 1 mg/mL, made up in mobile phase (or CH$_3$CN:dIW = 50:50 for acids/salts) |
| Retention times | Compound 1 - 20 min |
| | Diastereoisomers C (compounds 4/5) 9 min |
| | Diastereoisomers B (compounds 2/3) 10 min |

| Chiral method | |
|---|---|
| Column | ChiralPack IC, 5μ, 250 × 4.6 mm |
| Wavelength | 210 nm |
| Temperature | 25° C. |
| Flow rate | 0.35 mL/min |
| Mobile phase | n-Heptane/IPA/HOAc (or TFA) = 90/10/0.1 |
| Sample | 1 mg/mL, made up in mobile phase (or nHeptane/IPA/MeOH = 81/9/10 for salts) |
| Retention times | Compound A 54 min and >60 min |
| | Compound 4 - 30 min |
| | Compound 5 - 37 min |
| | Compound 3 - 18 min |
| | Compound 2 - 19 min |

Salt Formation

Salts were prepared by dissolving the free acid of compounds 2, 3, 4 and 5 in aqueous or aqueous organic solvent in the presence of the appropriate base and isolating the salt by evaporation of solvent.

Compound 6

The N-Methyl-(D)-Glucamine salt (NMDG) of Compound 2

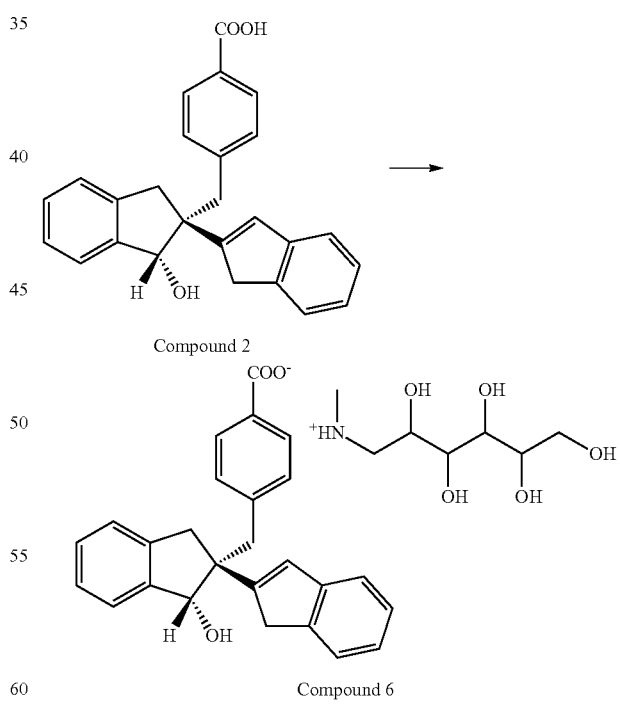

Compound 6 Physiochemical Properties:
Appearance: Off-white solid
Molecular Weight: 577 (free acid: 382)
Molecular Formula: C$_{33}$H$_{39}$O$_8$N (free acid: C$_{26}$H$_{22}$O$_3$)
Melting Point: 165-167° C.

Compound 6: [α]$_D$: −76.5 (sample concentration: 200 mg/10 ml in Water)

Mass (Da): ES+ only [NMDG+Na] was visible

Elemental analysis: Calc: C (68.61), H (6.80), N (2.42), O (22.16). Found: C (68.44), H (6.80), N (2.50), O (21.98)

δ$_H$ (400 MHz, DMSO-d6): 2.48 (3H, apparent s, NCH$_3$), 2.65 (1H, d, J=13.56 Hz, HCH), 2.84-3.02 (4H, m), 3.16 (1H, d, J=13.60 Hz, HCH), 3.40-3.70 (7H, m), 3.85-3.92 (1H, m), 5.06 (1H, s, CH—OH), 5.93 (1H, broad s, CH—OH), 6.41 (1H, s, CH=C), 6.80 (2H, d, J=7.92 Hz, Ar—H), 7.06-7.41 (8H, m, Ar—H), 7.64 (2H, d, J=7.80 Hz, Ar—H).

δ$_C$(100 MHz, DMSO): 33.8 (CH$_3$), 37.9 (CH$_2$), 38.2 (CH$_2$), 39.5 (CH$_2$), 51.6 (CH$_2$—N), 55.8 (quat. C), 63.5 (CH$_2$—O), 69.0 (CH—O), 70.3 (CH—O), 70.6 (CH—O), 71.3 (CH—O), 81.1 (CH—OH), 120.1 (tert. C), 123.4 (tert. C), 123.7 (tert. C), 124.3 (tert. C), 124.4 (tert. C), 126.1 (tert. C), 126.3 (tert. C), 127.0 (tert. C), 127.5 (tert. C), 2×128.5 (2×tert. C), 2×129.1 (2×tert. C), 140.4 (quat. C), 141.1 (quat. C), 142.9 (quat. C), 144.5 (quat. C), 145.2 (quat. C), 154.3 (quat. C), 170.4 (C=O).

X-Ray Studies

The absolute stereochemistry of compound 2 was established by single crystal X-ray analysis of its (S)-(−)-methylbenzylamine salt (compound 8). The results are given in Appendix 2. The results were in agreement with the stereochemistry shown in FIG. 2. The absolute stereochemistry of compounds 4 and 5 were established by conversion of the alcohols (compounds 2-5) to their ketones and by correlation of their optical rotations.

Synthesis of methyl 4-(((1R,2R)-1-hydroxy-2,3-dihydro-1H,1'H-[2,2'-biinden]-2-yl)methyl)benzoate (10)

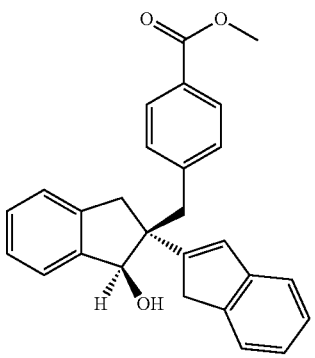 [SMILES: COC(=O)c1ccc(C[C@]2(C3=Cc4ccccc4C3)Cc3ccccc3[C@@H]2O)cc1]

To a solution of 4-(((1R,2R)-1-hydroxy-2,3-dihydro-1H,1'H-[2,2'-biinden]-2-yl)methyl)benzoic acid (100 mg, 0.26 mmol) and K$_2$CO$_3$ (72 mg, 0.52 mmol) in DMF (2.5 mL), was added MeI (148 mg, 1.04 mmol) and then stirred at room temperature for 4 h. The reaction mixture was diluted with 1.5 N HCl (50 mL) and extracted with ethyl acetate (3×25 mL). The separated organic layer was washed with 10% aq. NaHCO$_3$ (25 mL), brine (25 mL), dried over anhydrous Na$_2$SO$_4$ and evaporated under reduced pressure. The residue was purified by CombiFlash using 20% ethyl acetate in chloroform as an eluent to yield 58 mg (56%) of the title compound as an off white solid.

LCMS (—OH): observed 379.3 calculated 396.17, molecular formula C$_{27}$H$_{24}$O$_3$ Purity (HPLC): 94%.

$^1$H NMR (400 MHz, DMSO-d$_6$): δ 2.73 (1H, d, J=13.48 Hz, CH$_2$), 2.96 (2H, s, CH$_2$), 3.20 (1H, d, J=13.52 Hz, CH$_2$), 3.44 (1H, d, J=23.16 Hz, CH$_2$), 3.58 (1H, d, J=23.00 Hz, CH$_2$), 3.78 (3H, s, OCH$_3$), 5.06 (1H, d, J=6.76 Hz, CHOH), 5.85 (1H, d, J=6.88 Hz, OH), 6.40 (1H, s, CH=C), 6.98 (2H, d, J=8.16 Hz, Ar—H), 7.08 (1H, t, J=7.32 Hz, Ar—H), 7.16 (1H, t, J=7.40 Hz, Ar—H), 7.20-7.23 (4H, m, Ar—H), 7.34-7.36 (1H, m, Ar—H), 7.39 (1H, d, J=7.36 Hz, Ar—H), 7.71 (2H, d, J=8.16 Hz, Ar—H).

Synthesis of ethyl 4-(((1R,2R)-1-hydroxy-2,3-dihydro-1H,1'H-[2,2'-biinden]-2-yl)methyl)benzoate (11)

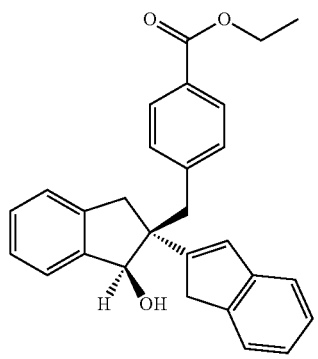 [SMILES: CCOC(=O)c1ccc(C[C@]2(C3=Cc4ccccc4C3)Cc3ccccc3[C@@H]2O)cc1]

To a solution of 4-(((1R,2R)-1-hydroxy-2,3-dihydro-1H,1'H-[2,2'-biinden]-2-yl)methyl)benzoic acid (100 mg, 0.26 mmol) and K$_2$CO$_3$ (72 mg, 0.52 mmol) in DMF (2.5 mL), was added EtI (82 mg, 0.52 mmol) and then stirred at room temperature for 4 h. The reaction mixture was diluted with 1.5 N HCl (50 mL) and extracted with ethyl acetate (3×25 mL). The organic layer was washed with 10% aq. NaHCO$_3$ (25 mL), brine (25 mL), dried over anhydrous Na$_2$SO$_4$ and evaporated under reduced pressure. The residue was purified by CombiFlash using 20% ethyl acetate in chloroform as an eluent to yield 88 mg (82%) of the title compound as an off white solid.

LCMS (—OH): observed 393.3, calculated 410.19, molecular formula C$_{28}$H$_{26}$O$_3$ Purity (HPLC): 92%.

$^1$H NMR (400 MHz, DMSO-d$_6$): δ 1.27 (3H, t, J=7.08 Hz, CH$_3$), 2.72 (1H, d, J=13.52 Hz, CH$_2$), 2.96 (2H, s, CH$_2$), 3.20 (1H, d, J 13.48 Hz, CH$_2$), 3.45 (1H, d, J=23.08 Hz, CH$_2$), 3.59 (1H, d, J=22.84 Hz, CH$_2$), 4.24 (2H, q, J=7.08 Hz, OCH$_2$), 5.05 (1H, d, J=6.84 Hz, CHOH), 5.85 (1H, d, J=6.92 Hz, OH), 6.40 (1H, s, CH=C), 6.97 (2H, d, J=8.24 Hz, Ar—H), 7.08 (1H, td, J=1.16, 7.30 Hz, Ar—H), 7.16 (1H, t, J=6.84 Hz, Ar—H), 7.19-7.25 (4H, m, Ar—H), 7.34-7.36 (1H, m, Ar—H), 7.40 (1H, d, J=7.36 Hz, Ar—H), 7.70 (2H, d, J=8.20 Hz, Ar—H).

Synthesis of propyl 4-(((1R,2R)-1-hydroxy-2,3-dihydro-1H,1'H-[2,2'-biinden]-2-yl)methyl)benzoate (12)

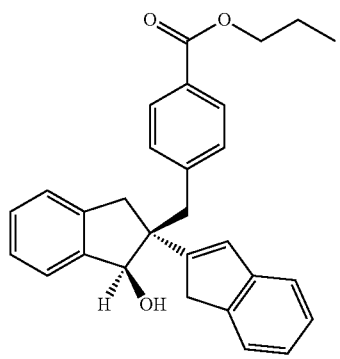 [SMILES: CCCOC(=O)c1ccc(C[C@]2(C3=Cc4ccccc4C3)Cc3ccccc3[C@@H]2O)cc1]

To a solution of 4-(((1R,2R)-1-hydroxy-2,3-dihydro-1H, 1'H-[2,2'-biinden]-2-yl)methyl)benzoic acid (100 mg, 0.26 mmol) and K₂CO₃ (72 mg, 0.52 mmol) in DMF (2.5 mL), was added n-PrI (90 mg, 0.52 mmol) and then stirred at room temperature for 4 h. The reaction mixture was diluted with 1.5 N HCl (50 mL) and extracted with ethyl acetate (3×25 mL). The organic layer was washed with 10% aq. NaHCO₃ (25 mL), brine (25 mL), dried over anhydrous Na₂SO₄ and evaporated under reduced pressure. The residue was purified by CombiFlash using 20% ethyl acetate in chloroform as an eluent to yield 82 mg (73%) of the title compound as an off white solid.

LCMS (—OH): observed 407.3, calculated 424.20, molecular formula $C_{29}H_{28}O_3$ Purity (HPLC): 95%.

¹H NMR (400 MHz, DMSO-d₆): δ 0.93 (3H, t, J=7.40 Hz, CH₃), 1.67 (2H, q, J=6.92 Hz, OCH₂CH₂), 2.72 (1H, d, J=13.56 Hz, CH₂), 2.96 (2H, s, CH₂), 3.20 (1H, d, J=13.52 Hz, CH₂), 3.46 (1H, d, J=22.84 Hz, CH₂), 3.59 (1H, d, J=22.96 Hz, CH₂), 4.16 (2H, t, J=6.56 Hz, OCH₂), 5.05 (1H, d, J=6.88 Hz, CHOH), 5.85 (1H, d, J=6.92 Hz, OH), 6.40 (1H, s, CH=C), 6.98 (2H, d, J=8.16 Hz, Ar—H), 7.10 (1H, dt, J=1.00 Hz, Ar—H), 7.16 (1H, t, J=7.32 Hz, Ar—H), 7.21-7.25 (4H, m, Ar—H), 7.35-7.36 (1H, m, Ar—H), 7.40 (1H, d, J=7.28 Hz, Ar—H), 7.71 (2H, d, J=8.16 Hz, Ar—H).

Synthesis of 4-{[(1'R,2'R)-1'-hydroxy-1',3'-dihydro-1H,2'H-2,2'-biinden-2'-yl]methyl}benzamide (13)

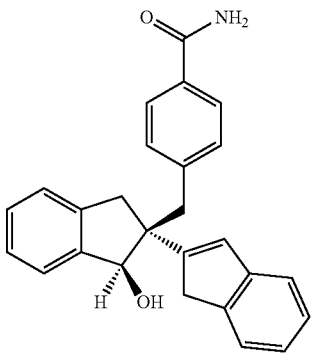 [SMILES: NC(=O)c1ccc(C[C@]2(C3=Cc4ccccc4C3)Cc3ccccc3[C@@H]2O)cc1]

To a solution of 4-(((1R,2R)-1-hydroxy-2,3-dihydro-1H, 1'H-[2,2'-biinden]-2-yl)methyl)benzoic acid (100 mg, 0.26 mmol) in DMSO (5 mL) was added Boc anhydride (69 mg, 0.31 mmol) followed by pyridine (24 mg, 0.26 mmol) and stirred at room temperature for 5 min. Ammonium bicarbonate (62 mg, 0.78 mmol) was added and stirred for additional 1 h. Reaction mixture was poured into water (25 mL) and extracted with ethyl acetate (3×25 mL). The organic layer was washed with brine (25 mL), dried over anhydrous Na₂SO₄ and evaporated under reduced pressure. The residue was purified by CombiFlash using 20% ethyl acetate in chloroform as an eluent to yield 59 mg (59%) of the title compound as an off white solid.

LCMS (+H⁺): observed 382.4, calculated 381.17, molecular formula $C_{26}H_{23}NO_2$ Purity (HPLC): 99%.

¹H NMR (400 MHz, DMSO-d₆): δ 2.68 (1H, d, J=13.60 Hz, CH₂), 2.94 (1H, d J=16.92 Hz, CH₂), 2.99 (1H, d, J=16.00 Hz, CH₂), 3.19 (1H, d, J=13.60 Hz, CH₂), 3.47 (1H, d, J=23.08 Hz, CH₂), 3.61 (1H, d, J=23.00 Hz, CH₂), 5.05 (1H, d, J=6.92 Hz, CHOH), 5.84 (1H, d, J=6.96 Hz, OH), 6.41 (1H, s, CH=C), 6.89 (2H, d, J=8.20 Hz, Ar—H), 7.09 (1H, td, J=1.28, 7.28 Hz, Ar—H), 7.17 (1H, t, J=7.32 Hz, Ar—H), 7.22-7.27 (5H, m, Ar—H and NH), 7.35-7.37 (1H, m, Ar—H), 7.41 (1H, d, J=7.32 Hz, Ar—H), 7.63 (2H, d, J=8.24 Hz, Ar—H), 7.82 (1H, br s, NH).

Synthesis of 4-{[(1'R,2'R)-1'-hydroxy-1',3'-dihydro-1H,2'H-2,2'-biinden-2'-yl]methyl}-N-(2-hydroxyethyl)benzamide (14)

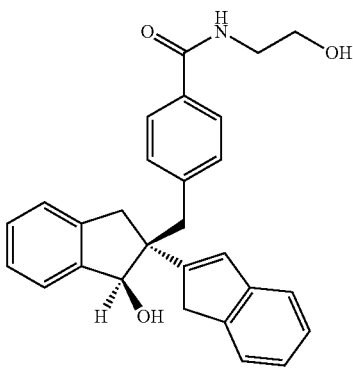 [SMILES: O=C(NCCO)c1ccc(C[C@]2(C3=Cc4ccccc4C3)Cc3ccccc3[C@@H]2O)cc1]

To a solution of 4-(((1R,2R)-1-hydroxy-2,3-dihydro-1H, 1'H-[2,2'-biinden]-2-yl)methyl)benzoic acid (100 mg, 0.26 mmol), Et₃N (157 mg, 1.56 mmol) and 2-amino ethanol (40 mg, 0.65 mmol) in DCM (5 mL), was added T₃P (0.33 mL, 50 wt % solution in ethyl acetate, 0.52 mmol) and then stirred at room temperature for 12 h. The reaction mixture was quenched with water (25 mL) and extracted with DCM (3×25 mL). The organic layer was washed with brine (25 mL), dried over anhydrous Na₂SO₄ and evaporated under reduced pressure. The residue was purified by CombiFlash using 20% ethyl acetate in chloroform as an eluent to yield 80 mg (72%) of the title compound as an off white solid.

LCMS (+H⁺): observed 426.4, calculated 425.20, molecular formula $C_{28}H_{27}NO_3$ Purity (HPLC): 99%.

¹H NMR (400 MHz, DMSO-d₆): δ 2.68 (1H, d, J=13.56 Hz, CH₂), 2.94 (1H, d, J=15.64 Hz, CH₂), 2.98 (1H, d, J=15.84 Hz, CH₂), 3.19 (1H, d, J=13.56 Hz, CH₂), 3.26-3.29 (2H, m, CONHCH₂), 3.43-3.49 (3H, m, 2H of CH and 1H of CH₂), 3.61 (1H, d, J=23.16 Hz, CH₂), 4.68 (1H, t, J=5.60 Hz, CH₂OH), 5.05 (1H, d, J=6.88 Hz, CHOH), 5.84 (1H, d, J=6.96 Hz, CHOH), 6.40 (1H, s, CH=C), 6.89 (2H, d, J=8.20 Hz, Ar—H), 7.09 (1H, dt, J=1.20, 10.13 Hz, Ar—H), 7.17 (1H, t, J=7.40 Hz, Ar—H), 7.21-7.28 (4H, m, Ar—H), 7.35-7.37 (1H, m, Ar—H), 7.41 (1H, d, J=7.28 Hz, Ar—H), 7.61 (2H, d, J=8.20 Hz, Ar—H), 8.28 (1H, t, J=5.64 Hz, NH).

Synthesis of 4-{[(1'R,2'R)-1'-hydroxy-1',3'-dihydro-1H,2'H-2,2'-biinden-2'-yl]methyl}-N-methylbenzamide (15)

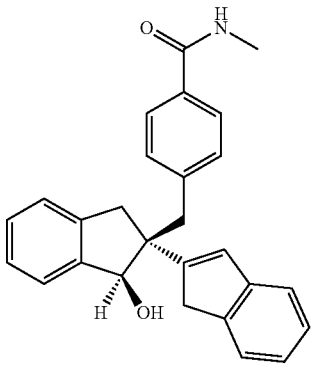 [SMILES: CNC(=O)c1ccc(C[C@]2(C3=Cc4ccccc4C3)Cc3ccccc3[C@@H]2O)cc1]

To a solution of 4-(((1R,2R)-1-hydroxy-2,3-dihydro-1H,1'H-[2,2'-biinden]-2-yl)methyl)benzoic acid (100 mg, 0.26 mmol), Et$_3$N (157 mg, 1.56 mmol) and methyl amine (0.32 mL, 2.0 M solution in THF, 0.65 mmol) in DCM (5 mL), was added. T$_3$P (0.33 mL, 50 wt % solution in ethyl acetate, 0.52 mmol) and then stirred at room temperature for 12 h. The reaction mixture was quenched with water (25 mL) and extracted with DCM (3×25 mL). The organic layer was washed with brine (25 mL), dried over anhydrous Na$_2$SO$_4$ and evaporated under reduced pressure. The residue was purified by CombiFlash using 20% ethyl acetate in chloroform as an eluent to yield 89 mg (86%) of the title compound as an off white solid.

LCMS (+H$^+$): observed 396.4, calculated 395.19, molecular formula C$_{27}$H$_{25}$NO$_2$ Purity (HPLC): 100%.

$^1$H NMR (400 MHz, DMSO-d$_6$): δ 2.67 (1H, d, J=13.60 Hz, CH$_2$), 2.72 (3H, d, J=4.48 Hz, CONHCH$_3$), 2.93 (1H, d, J 15.64 Hz, CH$_2$), 2.98 (1H, d, J=15.68 Hz, CH$_2$), 3.18 (1H, d, J=13.60 Hz, CH$_2$), 3.44 (1H, d, J=23.12 Hz, CH$_2$), 3.59 (1H, d, J=23.04 Hz, CH$_2$), 5.05 (1H, d, J=6.88 Hz, CHOH), 5.83 (1H, d, J=6.92 Hz, OH), 6.40 (1H, s, CH═C), 6.89 (2H, d, J=8.12 Hz, Ar—H), 7.06-7.10 (1H, m, Ar—H), 7.16 (1H, t, J=7.32 Hz, Ar—H), 7.23-7.27 (4H, m, Ar—H), 7.34-7.36 (1H, m, Ar—H), 7.40 (1H, d, J=7.24 Hz, Ar—H), 7.57 (2H, d, J=8.16 Hz, Ar—H), 8.26-8.28 (1H, m, NH).

Synthesis of 4-{[(1'R,2'R)-1'-hydroxy-1',3'-dihydro-1H,2'H-2,2'-biinden-2'-yl]methyl}-N,N-dimethylbenzamide (16)

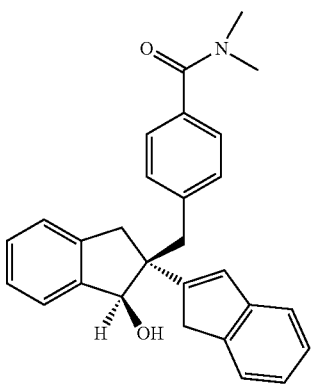 [SMILES: CN(C)C(=O)c1ccc(C[C@]2(C3=Cc4ccccc4C3)Cc3ccccc3[C@@H]2O)cc1]

To a solution of 4-(((1R,2R)-1-hydroxy-2,3-dihydro-1H,1'H-[2,2'-biinden]-2-yl)methyl)benzoic acid (100 mg, 0.26 mmol), Et$_3$N (157 mg, 1.56 mmol) and dimethyl amine (0.33 mL, 2.0 M solution in THF, 0.65 mmol) in DCM (5 mL), was added T$_3$P (0.33 mL, 50 wt % solution in ethyl acetate, 0.52 mmol) and then stirred at room temperature for 12 h. The reaction mixture was quenched with water (25 mL) and extracted with DCM (3×25 mL). The organic layer was washed with brine (25 mL), dried over anhydrous Na$_2$SO$_4$ and evaporated under reduced pressure. The residue was purified by CombiFlash using 20% ethyl acetate in chloroform as an eluent to yield 75 mg (70%) of the title compound as an off white solid.

LCMS (+H$^+$): observed 410.4, calculated 409.20, molecular formula C$_{28}$H$_{27}$NO$_2$ Purity (HPLC): 100%.

$^1$H NMR (400 MHz, DMSO-d$_6$): δ 2.69 (1H, d, J=13.60 Hz, CH$_2$), 2.83 (3H, s, CONCH$_3$), 2.93 (3H, s, CONCH$_3$), 2.98 (2H, s, CH$_2$), 3.16 (1H, d, J=13.52 Hz, CH$_2$), 3.45 (1H, d, J=23.44 Hz, CH$_2$), 3.59 (1H, d, J=23.04 Hz, CH$_2$), 5.06 (1H, d, J=6.84 Hz, CHOH), 5.85 (1H, d, J=6.96 Hz, OH), 6.45 (1H, s, CH═C), 6.89 (2H, d, J=8.04 Hz, Ar—H), 7.07-7.24 (8H, m, Ar—H), 7.34-7.36 (1H, m, Ar—H), 7.40 (1H, d, J=7.24 Hz, Ar—H).

Synthesis of methyl 4-(((1S,2S)-1-hydroxy-2,3-dihydro-1H,1'H-[2,2'-biinden]-2-yl)methyl)benzoate (17)

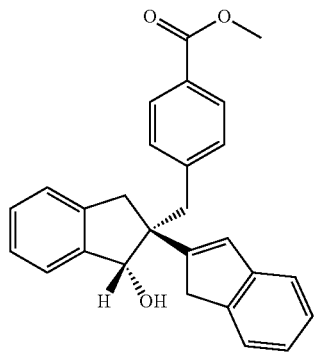 [SMILES: COC(=O)c1ccc(C[C@@]2(C3=Cc4ccccc4C3)Cc3ccccc3[C@H]2O)cc1]

To a solution of 4-(((1S,2S)-1-hydroxy-2,3-dihydro-1H,1'H-[2,2'-biinden]-2-yl)methyl)benzoic acid (100 mg, 0.26 mmol) and K$_2$CO$_3$ (72 mg, 0.52 mmol) in DMF (2.5 mL), was added MeI (148 mg, 1.04 mmol) and then stirred at room temperature for 4 h. The reaction mixture was diluted with 1.5 N HCl (50 mL) and extracted with ethyl acetate (3×25 mL). The organic layer was washed with 10% aq. NaHCO$_3$ (25 mL), brine (25 mL), dried over anhydrous Na$_2$SO$_4$ and evaporated under reduced pressure. The residue was purified by CombiFlash using 20% ethyl acetate in chloroform as an eluent to yield 62 mg (59%) of the title compound as an off white solid.

LCMS (—OH): observed 379.2, calculated 396.17, molecular formula C$_{27}$H$_{24}$O$_3$ Purity (HPLC): 97%.

$^1$H NMR (400 MHz, CDCl$_3$): δ 2.84 (1H, d, J=13.28 Hz, CH$_2$), 3.00 (1H, d, J=15.64 Hz, CH$_2$), 3.05 (1H, d, J=15.56 Hz, CH$_2$), 3.27 (1H, d, J=13.32 Hz, CH$_2$), 3.45 (1H, d, J=22.52 Hz, CH$_2$), 3.57 (1H, d, J=22.60 Hz, CH$_2$), 3.89 (3H, s, OCH$_3$), 5.25 (1H, s, CHOH), 6.47 (1H, s, CH═C), 6.96 (2H, d, J=8.24 Hz, Ar—H), 7.17 (1H, dt, J=2.04, 9.88 Hz, Ar—H), 7.24-7.33 (5H, m, Ar—H), 7.43 (2H, d, J=7.60 Hz, Ar—H), 7.83 (2H, dd, J=1.76, 6.60 Hz, Ar—H).

Synthesis of ethyl 4-(((1S,2S)-1-hydroxy-2,3-dihydro-1H,1'H-[2,2'-biinden]-2-yl)methyl)benzoate (18)

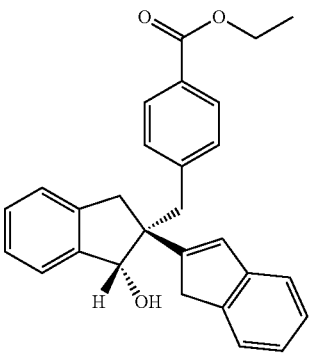 [SMILES: CCOC(=O)c1ccc(C[C@@]2(C3=Cc4ccccc4C3)Cc3ccccc3[C@H]2O)cc1]

To a solution of 4-(((1S,2S)-1-hydroxy-2,3-dihydro-1H,1'H-[2,2'-biinden]-2-yl)methyl)benzoic acid (100 mg, 0.26 mmol) and $K_2CO_3$ (72 mg, 0.52 mmol) in DMF (2.5 mL), was added EtI (81 mg, 0.52 mmol) and then stirred at room temperature for 4 h. The reaction mixture was diluted with 1.5 N HCl (50 mL) and extracted with ethyl acetate (3×25 mL). The organic layer was washed with 10% aq. $NaHCO_3$ (25 mL), brine (25 mL), dried over anhydrous $Na_2SO_4$ and evaporated under reduced pressure. The residue was purified by CombiFlash using 20% ethyl acetate in chloroform as an eluent to yield 55 mg (50%) of the title compound as an off white solid.

LCMS (—OH): observed 393.4, calculated 410.19, molecular formula $C_{28}H_{26}O_3$ Purity (HPLC): 92%.

$^1$H NMR (400 MHz, $CDCl_3$): δ 1.38 (3H, t, J=7.12 Hz, CH_3), 2.84 (1H, d, J=13.28 Hz, CH_2), 3.00 (1H, d, J=15.60 Hz, CH_2), 3.05 (1H, d, J=15.60 Hz, CH_2), 3.27 (1H, d, J=13.28 Hz, CH2), 3.45 (1H, d, J=22.52 Hz, CH_2), 3.58 (1H, d, J=22.52 Hz, CH_2), 4.35 (2H, q, J=7.12 Hz, OCH_2), 5.25 (1H, s, CHOH), 6.48 (1H, s, CH=C), 6.96 (2H, d, J=8.28 Hz, Ar—H), 7.17 (1H, dt, J=2.00, 9.92 Hz, Ar—H), 7.25-7.34 (5H, m, Ar—H), 7.44 (2H, d, J=7.72 Hz, Ar—H), 7.85 (2H, dd, J=1.72, 6.56 Hz, Ar—H).

Synthesis of propyl 4-((1S,2S)-1-hydroxy-2,3-dihydro-1H,1'H-[2,2'-biinden]-2-yl)methyl)benzoate (19)

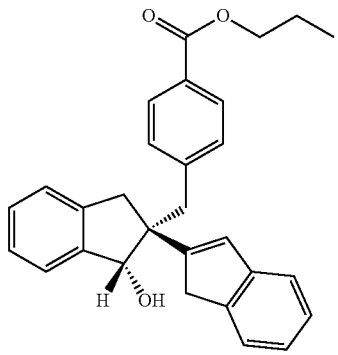 [SMILES: CCCOC(=O)c1ccc(C[C@@]2(C3=Cc4ccccc4C3)Cc3ccccc3[C@H]2O)cc1]

To a solution of 4-(((1S,2S)-1-hydroxy-2,3-dihydro-1H,1'H-[2,2'-biinden]-2-yl)methyl)benzoic acid (100 mg, 0.26 mmol) and $K_2CO_3$ (72 mg, 0.52 mmol) in DMF (2.5 mL), was added n-PrI (89 mg, 0.52 mmol) and then stirred at room temperature for 4 h. The reaction mixture was diluted with 1.5 N HCl (50 mL) and extracted with ethyl acetate (3×25 mL). The organic layer was washed with 10% aq. $NaHCO_3$ (25 mL), brine (25 mL), dried over anhydrous $Na_2SO_4$ and evaporated under reduced pressure. The residue was purified by CombiFlash using 20% ethyl acetate in chloroform as an eluent to yield 54 mg (50%) of the title compound as a pale yellow solid.

LCMS (—OH): observed 407.2, calculated 424.20, molecular formula $C_{29}H_{28}O_3$ Purity (HPLC): 90%.

$^1$H NMR (400 MHz, $CDCl_3$): δ 1.03 (3H, t, J=7.48 Hz, CH_3), 1.73-1.82 (2H, m, CH_2), 2.84 (1H, d, J=13.32 Hz, CH_2), 3.00 (1H, d, J=15.04 Hz, CH_2), 3.06 (1H, d, J=15.52 Hz, CH_2), 3.27 (1H, d, J=13.32 Hz, CH_2), 3.46 (1H, d, J=22.56 Hz, CH_2), 3.58 (1H, d, J=22.68 Hz, CH_2), 4.26 (2H, t, J=6.64 Hz, OCH_2), 5.25 (1H, s, CHOH), 6.48 (1H, s, CH=C), 6.96 (2H, d, J=8.24 Hz, Ar—H), 7.18 (1H, dt, J=1.96, 9.96 Hz, Ar—H), 7.24-7.33 (5H, m, Ar—H), 7.44 (2H, d, J=7.60 Hz, Ar—H), 7.85 (2H, dd, J=1.68, 6.60 Hz, Ar—H).

Synthesis of 4-{[(1'S,2'S)-1'-hydroxy-1',3'-dihydro-1H,2'H-2,2'-biinden-2'-yl]methyl}benzamide (20)

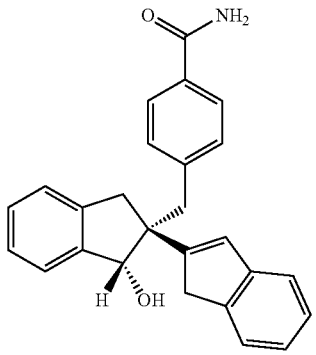 [SMILES: NC(=O)c1ccc(C[C@@]2(C3=Cc4ccccc4C3)Cc3ccccc3[C@H]2O)cc1]

To a solution of 4-(((1S,2S)-1-hydroxy-2,3-dihydro-1H,1'H-[2,2'-biinden]-2-yl)methyl)benzoic acid (100 mg, 0.26 mmol) in DMSO (5 mL) was added Boc anhydride (69 mg, 0.31 mmol) followed by pyridine (24 mg, 0.26 mmol) and stirred at room temperature for 5 min. Ammonium bicarbonate (62 mg, 0.78 mmol) was added and stirred for additional 1 h. Reaction mixture was poured into water (25 mL) and extracted with ethyl acetate (3×25 mL). The organic layer was washed with brine (25 mL), dried over anhydrous $Na_2SO_4$ and evaporated under reduced pressure. The residue was purified by CombiFlash using 20% ethyl acetate in chloroform as an eluent to yield 57 mg (57%) of the title compound as an off white solid.

LCMS (—OH): observed 364.2, calculated 381.17, molecular formula $C_{26}H_{23}NO_2$ Purity (HPLC): 98%.

$^1$H NMR (400 MHz, $CDCl_3$): δ 2.84 (1H, d, J=13.32 Hz, CH_2), 3.00 (1H, d, J=15.68 Hz, CH_2), 3.05 (1H, d, J=15.56 Hz, CH_2), 3.26 (1H, d, J=13.32 Hz, CH_2), 3.46 (1H, d, J=22.60 Hz, CH_2), 3.58 (1H, d, J=22.68 Hz, CH_2), 5.25 (1H, s, CHOH), 5.65 and 6.07 (2H, 2×br s, NH and CHOH), 6.48 (1H, s, CH=C), 6.97 (2H, d, J=8.16 Hz, Ar—H), 7.17 (1H, dt, J=2.00, 9.95 Hz, Ar—H), 7.24-7.33 (5H, m, Ar—H), 7.44 (2H, d, J=7.56 Hz, Ar—H), 7.60 (2H, d, J=8.24 Hz, Ar—H).

Synthesis of 4-{[(1'S,2'S)-1'-hydroxy-1',3'-dihydro-1H,2'H-2,2'-biinden-2'-yl]methyl}-N-(2-hydroxyethyl)benzamide (21)

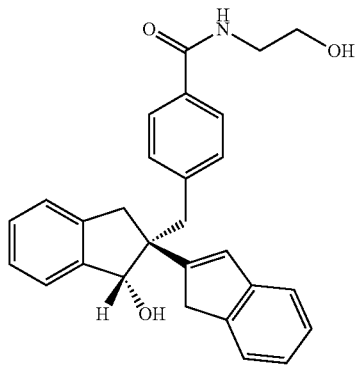 [SMILES: O=C(NCCO)c1ccc(C[C@@]2(C3=Cc4ccccc4C3)Cc3ccccc3[C@H]2O)cc1]

To a solution of 4-(((1S,2S)-1-hydroxy-2,3-dihydro-1H,1'H-[2,2'-biinden]-2-yl)methyl)benzoic acid (100 mg, 0.26 mmol), Et₃N (157 mg, 1.56 mmol) and 2-amino ethanol (40 mg, 0.65 mmol) in DCM (5 mL), was added T₃P (0.33 mL, 50 wt % solution in ethyl acetate, 0.52 mmol) and then stirred at room temperature for 12 h. The reaction mixture was quenched with water (25 mL) and extracted with DCM (3×25 mL). The organic layer was washed with brine (25 mL), dried over anhydrous Na₂SO₄ and evaporated under reduced pressure. The residue was purified by CombiFlash using 20% ethyl acetate in chloroform as an eluent to yield 76 mg (68%) of the title compound as an off white solid.

LCMS (+H⁺): observed 426.5, calculated 425.20, molecular formula C₂₈H₂₇NO₃

Purity (HPLC): 99%.

¹H NMR (400 MHz, DMSO-d₆): δ 2.68 (1H, d, J=13.44 Hz, CH₂), 2.94 (1H, d, J=15.04 Hz, CH₂), 2.98 (1H, d, J=16.28 Hz, CH₂), 3.19 (1H, d, J=13.32 Hz, CH₂), 3.25-3.30 (2H, m, CH₂), 3.44-3.49 (3H, m, 3H of 2×CH₂), 3.61 (1H, d, J=23.16 Hz, CH₂), 4.68 (1H, t, J=5.48 Hz, CH₂OH), 5.05 (1H, d, J=6.84 Hz, CH—OH), 5.84 (1H, d, J=6.88 Hz, CH—OH), 6.40 (1H, s, CH=C), 6.89 (2H, d, J=8.20 Hz, Ar—H), 7.09 (1H, dt, J=1.16, 10.12 Hz, Ar—H), 7.17 (1H, t, J=7.32 Hz, Ar—H), 7.22-7.28 (4H, m, Ar—H), 7.36 (1H, t, J=3.48 Hz, Ar—H), 7.41 (1H, d, J=7.20 Hz, Ar—H), 7.61 (2H, d, J=8.20 Hz, Ar—H), 8.28 (1H, t, J=5.52 Hz, NH).

Synthesis of 4-{[(1'S,2'S)-1'-hydroxy-1',3'-dihydro-1H,2'H-2,2'-biinden-2'-yl]methyl}-N-methylbenzamide (22)

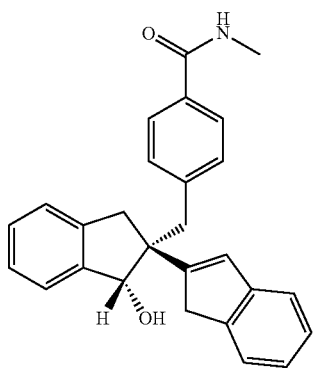 [SMILES: CNC(=O)c1ccc(C[C@@]2(C3=Cc4ccccc4C3)Cc3ccccc3[C@H]2O)cc1]

To a solution of 4-(((1S,2S)-1-hydroxy-2,3-dihydro-1H,1'H-[2,2'-biinden]-2-yl)methyl)benzoic acid (100 mg, 0.26 mmol), Et₃N (157 mg, 1.56 mmol) and methyl amine (0.32 mL, 2.0 M solution in THF, 0.65 mmol) in DCM (5 mL), was added T₃P (0.33 mL, 50 wt % solution in ethyl acetate, 0.52 mmol) and then stirred at room temperature for 12 h. The reaction mixture was quenched with water (25 mL) and extracted with DCM (3×25 mL). The organic layer was washed with brine (25 mL), dried over anhydrous Na₂SO₄ and evaporated under reduced pressure. The residue was purified by CombiFlash using 20% ethyl acetate in chloroform as an eluent to yield 80 mg (78%) of the title compound as an off white solid.

LCMS (+H⁺): observed 396.4, calculated 395.19, molecular formula C₂₇H₂₅NO₂

Purity (HPLC): 93%.

¹H NMR (400 MHz, DMSO-d₆): δ 2.68 (1H, d, J=13.64 Hz, CH₂), 2.72 (3H, d, J=4.48 Hz, CH₃), 2.94 (1H, d, J=16.28 Hz, CH₂), 2.99 (1H, d, =15.84 Hz, CH₂), 3.19 (1H, d, J=13.56 Hz, CH₂), 3.45 (1H, d, J=22.92 Hz, CH₂), 3.60 (1H, d, J=23.40 Hz, CH₂), 5.05 (1H, d, J=6.88 Hz, CHOH), 5.84 (1H, d; J=6.92 Hz, CHOH), 6.40 (1H, s, CH=C), 6.90 (2H, d, J=8.12 Hz, Ar—H), 7.09 (1H, t, J=7.24 Hz, Ar—H), 7.15-7.26 (5H, m, Ar—H), 7.35-7.37 (1H, m, Ar—H), 7.41 (1H, d, J=7.24 Hz, Ar—H), 7.58 (2H, d, J=8.16 Hz, Ar—H), 8.27 (1H, d, J=4.36 Hz, NH).

Synthesis of 4-{[(1'S,2'S)-1'-hydroxy-1',3'-dihydro-1H,2'H-2,2'-biinden-2'-yl]methyl}-N,N-dimethylbenzamide (23)

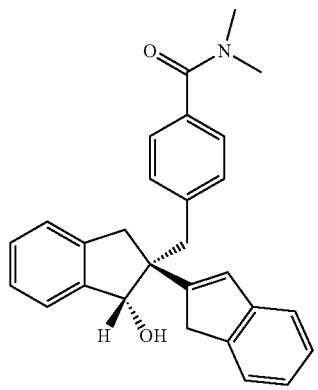 [SMILES: CN(C)C(=O)c1ccc(C[C@@]2(C3=Cc4ccccc4C3)Cc3ccccc3[C@H]2O)cc1]

To a solution of 4-(((1S,2S)-1-hydroxy-2,3-dihydro-1H,1'H-[2,2'-biinden]-2-yl)methyl)benzoic acid (100 mg, 0.26 mmol), Et₃N (157 mg, 1.56 mmol) and dimethyl amine (0.33 mL, 2.0 M solution in THF, 0.65 mmol) in DCM (5 mL), was added T₃P (0.33 mL, 50 wt % solution in ethyl acetate, 0.52 mmol) and then stirred at room temperature for 12 h. The reaction mixture was quenched with water (25 mL) and extracted with DCM (3×25 mL). The organic layer was washed with brine (25 mL), dried over anhydrous Na₂SO₄ and evaporated under reduced pressure. The residue was purified by CombiFlash using 20% ethyl acetate in chloroform as an eluent to yield 80 mg (75%) of the title compound as an off white solid.

LCMS (+H⁺): observed 410.4, calculated 409.20, molecular formula C₂₈H₂₇NO₂

Purity (HPLC): 97%.

¹H NMR (400 MHz, DMSO-d₆): δ 2.70 (1H, d, J=13.64 Hz, CH₂), 2.83-2.98 (8H, m, 2H of CH₂ and 6H of 2×CH₃), 3.16 (1H, d, J=13.60 Hz, CH$_2$), 3.45 (1H, d, J=22.92 Hz, CH$_2$), 3.59 (1H, d, J=23.20 Hz, CH$_2$), 5.06 (1H, s, CHOH), 6.45 (1H, s, CH=C), 6.89 (2H, d, J=8.08 Hz, Ar—H), 7.09 (1H, dt, J=1.20, 10.12 Hz, Ar—H), 7.13-7.17 (3H, m, Ar—H), 7.19-7.25 (4H, m, Ar—H), 7.34-7.36 (1H, m, Ar—H), 7.40 (1H, d, J=7.36 Hz, Ar—H).

Synthesis of 4-{[(1R,2'R)-1'-(L-leucyloxy)-1',3'-dihydro-1H,2'H-2,2'-biinden-2'-yl]methyl}benzoic acid (24)

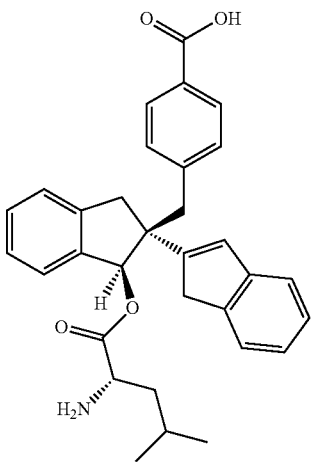 [SMILES: CC(C)C[C@H](N)C(=O)O[C@H]1c2ccccc2C[C@]1(Cc1ccc(C(=O)O)cc1)C1=Cc2ccccc2C1]

To a solution of 4-(((1R,2R)-1-hydroxy-2,3-dihydro-1H,1'H-[2,2'-biinden]-2-yl)methyl)benzoic acid (200 mg, 0.52 mmol), DCC (129 mg, 0.62 mmol) and DMAP (6 mg, 0.052 mmol) in ethyl acetate (10 mL), was added N-[(9H-fluoren-9-ylmethoxy)carbonyl]-L-leucine (183 mg, 0.52 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na$_2$SO$_4$. The organic layer was evaporated under reduced pressure and the residue 1 (210 mg) was dissolved in dry THF (5 mL) and cooled to 0° C. Dimethylamine (5 mL, 20% in THF) was added drop wise at N$_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 125 mg (49%) of the title compound as an off white solid.

LCMS (+H$^+$): observed 496.4, calculated 495.24, molecular formula C$_{32}$H$_{33}$NO$_4$ Purity (HPLC): 93%.

$^1$H NMR (400 MHz, DMSO-d$_6$): δ 0.90 (3H, d, J=8.00 Hz, CH$_3$), 0.93 (3H, d, J=8.00 Hz, CH$_3$), 1.58-1.66 (1H, m, CH), 1.68-1.76 (2H, m, CH$_2$), 3.13-3.37 (5H, m, 5H of 3×CH$_2$), 3.49 (1H, d, J=24.00 Hz, CH$_2$), 4.05 (1H, t, J=4.00 Hz, CH—N), 6.39 (1H, s, CH—O), 6.53 (1H, s, CH=C), 7.06-7.11 (3H, m, Ar—H), 7.16-7.23 (3H, m, Ar—H), 7.29-7.39 (4H, m, Ar—H), 7.73 (2H, d, J=8.00 Hz, Ar—H).

$^{13}$C NMR (100 MHz, DMSO-d$_6$): δ 22.36 (CH$_3$), 22.75 (CH$_3$), 24.36-25.80 (CH), 39.36-40.61 (4×CH$_2$), 51.59 and 54.71 (quat. C and CH—N), 84.38 (CH—O), 120.93, 123.92, 124.72, 125.27, 126.24, 126.72, 127.13, 129.20, 2×129.29, 129.51, 129.77, 2×130.35 (13×tert. C and 1×quat. C), 139.90 (quat. C), 142.99 (quat. C), 143.23 (quat. C), 143.90 (quat. C), 144.36 (quat. C), 151.55 (quat. C), 167.65 (O—C=O), 170.70 (C=O).

Synthesis of 4-{[(1'R,2'R)-1'-(L-valyloxy)-1',3'-dihydro-1H,2'H-2,2'-biinden-2'-yl]methyl}benzoic acid (25)

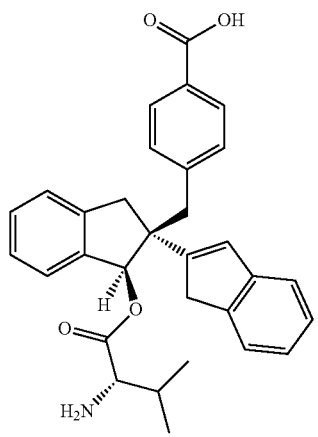 [SMILES: CC(C)[C@H](N)C(=O)O[C@H]1c2ccccc2C[C@]1(Cc1ccc(C(=O)O)cc1)C1=Cc2ccccc2C1]

To a solution of 4-(((1R,2R)-1-hydroxy-2,3-dihydro-1H,1'H-[2,2'-biinden]-2-yl)methyl)benzoic acid (230 mg, 0.60 mmol), DCC (148 mg, 0.72 mmol) and DMAP (7 mg, 0.059 mmol) in ethyl acetate (12 mL), was added N-[(9H-fluoren-9-ylmethoxy)carbonyl]-L-valine (193 mg, 0.60 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na$_2$SO$_4$. The organic layer was evaporated under reduced pressure and the residue 1 (250 mg) was dissolved in dry THF (7 mL) and cooled to 0° C. Dimethylamine (7 mL, 20% in THF) was added drop wise at N$_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 105 mg (36%) of the title compound as an off white solid.

LCMS (+H$^+$): observed 482.6, calculated 481.23, molecular formula C$_{31}$H$_{31}$NO$_4$ Purity (HPLC): 95%.

$^1$H NMR (400 MHz, DMSO-d$_6$): δ 0.97-1.05 (6H, m, (CH$_3$)$_2$), 2.30-2.35 (1H, m, CH), 3.12 (1H, d, J=12.84 Hz, CH$_2$), 3.16 (1H, d, J=5.48 Hz, CH$_2$), 3.21-3.24 (2H, m, CH$_2$), 3.41-3.49 (2H, m, CH$_2$), 4.05 (1H, d, J=4.28 Hz, CH—N), 6.40 (1H, s, CH—O), 6.56 (1H, s, CH=C), 7.08 (1H, dt, J=1.24, 10.15 Hz, Ar—H), 7.10-7.21 (5H, m, Ar—H), 7.28-7.40 (4H, m, Ar—H), 7.73 (2H, d, J=4.48 Hz, Ar—H).

$^{13}$C NMR (100 MHz, DMSO-d$_6$): δ 18.14 (CH$_3$), 18.43 (CH$_3$), 29.89 (CH), 39.36-40.61 (3×CH$_2$), 54.76 and 58.16 (quant. C and CH—N), 84.73 (CH—O), 120.91, 123.89, 124.72, 125.27, 126.39, 126.71, 127.08, 129.15, 2×129.26, 129.69, 129.83, 2×130.42 (13×tert. C and 1×quat. C), 139.93

(quat. C), 142.97 (quat. C), 143.53 (quat. C), 143.97 (quat. C), 144.36 (quat. C), 151.42 (quat. C), 167.66 (O—C=O), 169.09 (C=O).

Synthesis of 4-{[(1'R,2'R)-1'-(L-isoleucyloxy)-1',3'-dihydro-1H,2'H-2,2'-biinden-2'-yl]methyl}benzoic acid (26)

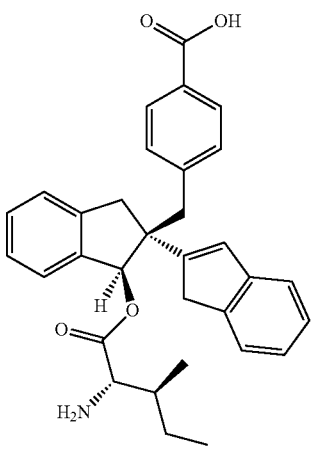 [SMILES: CC[C@H](C)[C@H](N)C(=O)O[C@H]1c2ccccc2C[C@]1(Cc1ccc(C(=O)O)cc1)C1=Cc2ccccc2C1]

To a solution of 4-(((1R,2R)-1-hydroxy-2,3-dihydro-1H, 1'H-[2,2'-biinden]-2-yl)methyl)benzoic acid (250 mg, 0.65 mmol), DCC (160 mg, 0.78 mmol) and DMAP (8 mg, 0.06 mmol) in ethyl acetate (15 mL), was added N-[(9H-fluoren-9-ylmethoxy)carbonyl]-L-isoleucine (228 mg, 0.65 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (275 mg) was dissolved in dry THF (10 mL) and cooled to 0° C. Dimethylamine (10 mL, 20% in THF) was added drop wise at $N_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 110 mg (31%) of the title compound as an off white solid.

LCMS (+H$^+$): observed 496.6, calculated 495.24, molecular formula $C_{32}H_{33}NO_4$ Purity (HPLC): 91%.

$^1$H NMR (400 MHz, DMSO-d6): δ 0.90 (3H, t, J=7.40 Hz, CH$_3$), 0.93 (3H, d, J=6.96 Hz, CH$_3$), 1.26-1.36 (1H, m, CH$_2$—CH$_3$), 1.44-1.52 (1H, m, CH$_2$—CH$_3$), 2.02-2.08 (1H, m, CH—CH$_3$), 3.09-3.25 (4H, m, 2×CH$_2$), 3.35-3.48 (2H, m, CH$_2$), 4.11 (1H, d, J=7.12 Hz, CH—N), 6.40 (1H, s, CH—O), 6.54 (1H, s, CH=C), 7.05-7.21 (6H, m, Ar—H), 7.27-7.38 (4H, m, Ar—H), 7.72 (2H, d, J=8.24 Hz, Ar—H), 8.58 (2H, br s, NH$_2$).

$^{13}$C NMR (100 MHz, DMSO-d6): δ 11.98 (CH$_3$), 14.95 (CH$_3$), 25.20 (CH$_2$), 36.42 (CH), 36.35-40.60 (3×CH$_2$), 54.77 (CH—N or quat. C), 57.26 (quat. C or CH—N), 84.77 (CH—O), 120.91, 123.89, 124.72, 125.23, 126.39, 126.72, 127.05, 129.15, 2×129.24, 129.65 129.78, 2×130.45 (13×tert. C and 1×quat. C), 139.91 (quat. C), 142.97 (quat. C), 143.43 (quat. C), 143.99 (quat. C), 144.36 (quat. C), 151.46 (quat. C), 167.66 (C=O), 168.83 (C=O).

Synthesis of 4-{[(1'R,2'R)-1'-(glycyloxy)-1',3'-dihydro-1H,2'H-2,2'-biinden-2'-yl]methyl}benzoic acid (27)

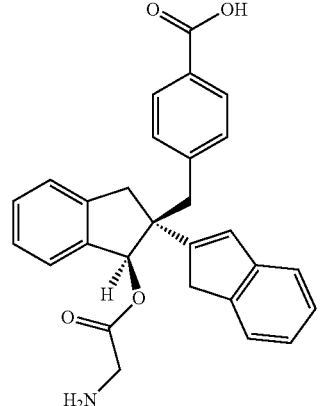

To a solution of 4-(((1R,2R)-1-hydroxy-2,3-dihydro-1H, 1'H-[2,2'-biinden]-2-yl)methyl)benzoic acid (220 mg, 0.57 mmol), DCC (142 mg, 0.69 mmol) and DMAP (7 mg, 0.059 mmol) in ethyl acetate (10 mL), was added N-[(9H-fluoren-9-ylmethoxy)carbonyl]glycine (171 mg, 0.57 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (250 mg) was dissolved in dry THF (8 mL) and cooled to 0° C. Dimethylamine (8 mL, 20% in THF) was added drop wise at $N_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 130 mg (56%) of the title compound as an off white solid.

LCMS (−H$^+$): observed 438.2, calculated 439.18, molecular formula $C_{28}H_{25}NO_4$ Purity (HPLC): 97%.

$^1$H NMR (400 MHz, DMSO-d6): δ 3.05-3.28 (5H, m, 5H of 3×CH$_2$), 3.45-3.50 (1H, m, CH$_2$), 3.60-3.76 (2H, m, NCH$_2$), 6.32 (1H, s, CH—O), 6.48 (1H, s, CH=C), 7.02 (2H, d, J=8.12 Hz, Ar—H), 7.05-7.09 (1H, m, Ar—H), 7.15-7.22 (3H, m, Ar—H), 7.28-7.36 (4H, m, Ar—H), 7.70 (2H, d, J=8.08 Hz, Ar—H).

$^{13}$C NMR (100 MHz, DMSO-d6): δ 39.36-40.61 (4×CH$_2$), 54.86 (quat. C), 82.96 (CH—O), 120.91, 123.94, 124.65, 125.24, 125.87, 126.69, 127.14, 2×129.21, 129.32, 129.52, 129.76, 2×130.33 (13×tert. C and 1×quat. C), 140.42 (quat.

C), 142.96 (quat. C), 143.04 (quat. C), 143.61 (quat. C), 144.43 (quat. C), 151.89 (quat. C), 167.89 (C=O).

Synthesis of 4-{[(1'S,2'S)-1'-(L-leucyloxy)-1',3'-dihydro-1H,2'H-2,2'-biinden-2'-yl]methyl}benzoic acid (28)

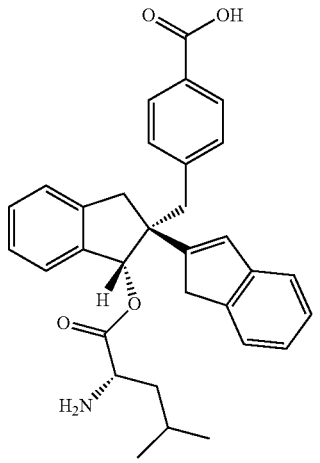 [SMILES: CC(C)C[C@H](N)C(=O)O[C@@H]1c2ccccc2C[C@@]1(Cc1ccc(C(=O)O)cc1)C1=Cc2ccccc2C1]

To a solution of 4-(((1S,2S)-1-hydroxy-2,3-dihydro-1H,1'H-[2,2'-biinden]-2-yl)methyl)benzoic acid (200 mg, 0.52 mmol), DCC (129 mg, 0.62 mmol) and DMAP (6 mg, 0.052 mmol) in ethyl acetate (10 mL), was added N-[(9H-fluoren-9-ylmethoxy)carbonyl]-L-leucine (183 mg, 0.52 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (210 mg) was dissolved in dry THF (5 mL) and cooled to 0° C. Dimethylamine (5 mL, 20% in THF) was added drop wise at $N_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 120 mg (47%) of the title compound as an off white solid.

LCMS (+H$^+$): observed 496.5, calculated 495.24, molecular formula $C_{32}H_{33}NO_4$ Purity (HPLC): 98%.

$^1$H NMR (400 MHz, DMSO-d$_6$): δ 0.84 (3H, d, J=6.24 Hz, CH$_3$), 0.86 (3H, d, J=6.28 Hz, CH$_3$), 1.37-1.71 (3H, 2×m, 1H of CH— and 2H of CH$_2$), 3.04-3.53 (7H, m, 6H of 3×CH and 1H of CH—N), 6.26 (1H, s, CH—O), 6.48 (1H, s, CH=C), 7.01 (2H, d, J=8.04 Hz, Ar—H), 7.08 (1H, dt, J=1.04, 10.12 Hz, Ar—H), 7.14-7.24 (4H, m, Ar—H), 7.25-7.36 (3H, m, Ar—H), 7.69 (2H, d, J=8.12 Hz, Ar—H).

Synthesis of 4-{[(1'S,2'S)-1'-(L-valyloxy)-1',3'-dihydro-1H,2'H-2,2'-biinden-2'-yl]methyl}benzoic acid (29)

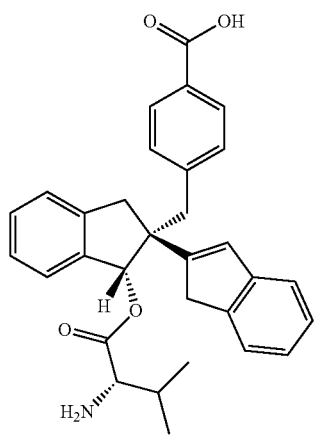 [SMILES: CC(C)[C@H](N)C(=O)O[C@@H]1c2ccccc2C[C@@]1(Cc1ccc(C(=O)O)cc1)C1=Cc2ccccc2C1]

To a solution of 4-(((1S,2S)-1-hydroxy-2,3-dihydro-1H,1'H-[2,2'-biinden]-2-yl)methyl)benzoic acid (230 mg, 0.60 mmol), DCC (148 mg, 0.72 mmol) and DMAP (7 mg, 0.06 mmol) in ethyl acetate (12 mL), was added N-[(9H-fluoren-9-ylmethoxy)carbonyl]-L-valine (193 mg, 0.60 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (250 mg) was dissolved in dry THF (8 mL) and cooled to 0° C. Dimethylamine (8 mL, 20% in THF) was added drop wise at $N_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 105 mg (36%) of the title compound as an off white solid.

LCMS (+H$^+$): observed 482.5, calculated 481.23, molecular formula $C_{31}H_{31}NO_4$ Purity (HPLC): 96%.

$^1$H NMR (400 MHz, DMSO-d$_6$): δ 0.80 (3H, d, J=6.80 Hz, CH$_3$), 0.87 (3H, d, J=6.80 Hz, CH$_3$), 1.88-1.90 (1H, m, CH), 3.05-3.47 (7H, m, 3×CH$_2$ and 1H of CH—N), 6.27 (1H, s, CH—O), 6.49 (1H, s, CH=C), 6.95 (2H, d, J=8.00 Hz, Ar—H), 7.07 (1H, t, J=14.40 Hz, Ar—H), 7.14-7.22 (3H, m, Ar—

H), 7.25-7.29 (2H, m, Ar—H), 7.32-7.35 (2H, m, Ar—H), 7.67 (2H, d, J=8.00 Hz, Ar—H).

Synthesis of 4-{[(1'S,2'S)-1'-(L-isoleucyloxy)-1',3'-dihydro-1H,2'H-2,2'-biinden-2'-yl]methyl}benzoic acid (PH30)

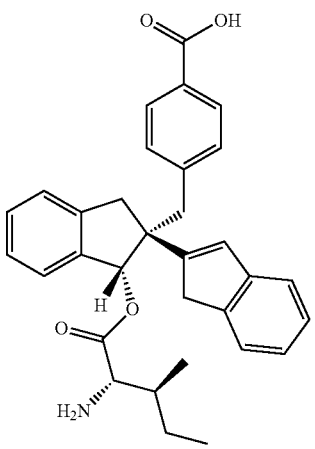 [SMILES: CC[C@H](C)[C@H](N)C(=O)O[C@@H]1c2ccccc2C[C@@]1(Cc1ccc(C(=O)O)cc1)C1=Cc2ccccc2C1]

To a solution of 4-(((1S,2S)-1-hydroxy-2,3-dihydro-1H,1'H-[2,2'-biinden]-2-yl)methyl)benzoic acid (250 mg, 0.65 mmol), DCC (160 mg, 0.78 mmol) and DMAP (8 mg, 0.06 mmol) in ethyl acetate (10 mL), was added N-[(9H-fluoren-9-ylmethoxy)carbonyl]-L-isoleucine (228 mg, 0.65 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (275 mg) was dissolved in dry THF (8 mL) and cooled to 0° C. Dimethylamine (8 mL, 20% in THF) was added drop wise at $N_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 110 mg (31%) of the title compound as an off white solid.

LCMS ($+H^+$): observed 496.4, calculated 495.24, molecular formula $C_{32}H_{33}NO_4$ Purity (HPLC): 95%.

$^1$H NMR (400 MHz, DMSO-d6): δ 0.77 (3H, t, J=8.00 Hz, CH$_3$), 0.82 (3H, d, J=4.00 Hz, CH$_3$), 1.02-1.12 (1H, m, CH$_2$—CH$_3$), 1.28-1.38 (1H, m, CH$_2$—CH$_3$), 1.62-1.68 (1H, m, CH—CH$_3$), 3.10-3.50 (7H, m, 6H of 3×CH$_2$ and 1H of CH—N), 6.26 (1H, s, CH—O), 6.49 (1H, s, CH=C), 7.01 (2H, d, J=8.00 Hz, Ar—H), 7.07 (1H, t, J=8.00 Hz, Ar—H), 7.13-7.21 (3H, m, Ar—H), 7.25-7.29 (2H, m, Ar—H), 7.33 (2H, t, J=8.00 Hz, Ar—H), 7.70 (2H, d, J=8.00 Hz, Ar—H).

$^{13}$C NMR (100 MHz, DMSO-d6): δ 11.94 (CH$_3$), 15.88 (CH$_3$), 24.90 (CH$_2$CH$_3$), 39.35-40.60 (3×CH$_2$ and 1×CH), 54.77 (quat. C or CH—N), 58.69 (CH—N or quat. C), 82.53 (CH—O), 120.86, 123.91, 124.60, 125.22, 125.84, 126.66, 127.02, 2×129.21, 2×129.32, 129.44, 2×130.05 (13×tert. C and 1×quat. C), 140.79 (quat. C), 2×143.01 (2×quat. C), 143.11 (quat. C), 144.45 (quat. C), 151.95 (quat. C), 175.25 (C=O).

Synthesis of 4-{[(1'S,2'S)-1'-(glycyloxy)-1',3'-dihydro-1H,2'H-2,2'-biinden-2'-yl]methyl}benzoic acid (31)

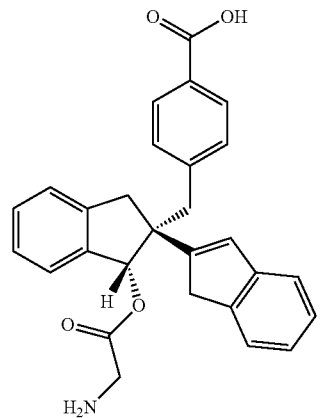 [SMILES: NCC(=O)O[C@@H]1c2ccccc2C[C@@]1(Cc1ccc(C(=O)O)cc1)C1=Cc2ccccc2C1]

To a solution of 4-(((1S,2S)-1-hydroxy-2,3-dihydro-1H,1'H-[2,2'-biinden]-2-yl)methyl)benzoic acid (220 mg, 0.57 mmol), DCC (142 mg, 0.69 mmol) and DMAP (7 mg, 0.057 mmol) in ethyl acetate (10 mL), was added N-[(9H-fluoren-9-ylmethoxy)carbonyl]glycine (171 mg, 0.57 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (250 mg) was dissolved in dry THF (8 mL) and cooled to 0° C. Dimethylamine (8 mL, 20% in THF) was added drop wise at $N_2$ atmosphere and the reaction mixture was slowly allowed to stir at room temperature for 1 h. The reaction mixture was evaporated under reduced pressure and the residue was purified by CombiFlash using 10% methanol in chloroform as an eluent to yield 130 mg (56%) of the title compound as an off white solid.

LCMS ($-H^+$): observed 438.4, calculated 439.18, molecular formula $C_{28}H_{25}NO_4$ Purity (HPLC): 95%.

$^1$H NMR (400 MHz, DMSO-d$_6$): δ 2.84-3.57 (8H, 2×m, 4×CH$_2$), 6.30 (1H, s, CH—O), 6.48 (1H, s, CH=C), 7.00 (2H, d, J=8.00 Hz, Ar—H), 7.09 (1H, t, J=7.20 Hz, Ar—H), 7.14-7.22 (3H, m, Ar—H), 7.28-7.37 (4H, m, Ar—H), 7.69 (2H, d, J=8.00 Hz, Ar—H).

Synthesis of methyl 4-(((1R,2R)-1-(((S)-2-amino-4-methylpentanoyl)oxy)-2,3-dihydro-1H,1'H-[2,2'-biinden]-2-yl)methyl)benzoate (32)

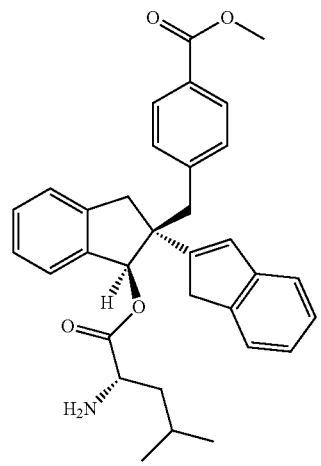 [SMILES: COC(=O)c1ccc(C[C@]2(C3=Cc4ccccc4C3)Cc3ccccc3[C@@H]2OC(=O)[C@@H](N)CC(C)C)cc1]

To a solution of methyl 4-(((1R,2R)-1-hydroxy-2,3-dihydro-1H,1'H-[2,2'-biinden]-2-yl)methyl)benzoate (10, 180 mg, 0.45 mmol), DCC (112 mg, 0.54 mmol) and DMAP (6 mg, 0.045 mmol) in ethyl acetate (10 mL), was added Fmoc leucine (158 mg, 0.45 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (250 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 30% ethyl acetate in petroleum ether as an eluent to yield 150 mg (66%) of the title compound as a colorless semi solid.

LCMS (+H$^+$): observed 510.0, calculated 509.26, molecular formula $C_{33}H_{35}NO_4$ Purity (HPLC): 94%.

$^1$H NMR (400 MHz, CDCl$_3$): δ 0.98 (3H, d, J=6.56 Hz, CH$_3$), 1.01 (3H, d, J=6.64 Hz, CH$_3$), 1.56-1.96 (3H, 3×m, 2H of CH$_2$—CH and 1H of —CH—), 3.06-3.37 (6H, m, 6H of 3×CH$_2$), 3.64 (1H, dd, J=5.40, 8.90 Hz, CH—N), 3.89 (3H, s, OCH$_3$), 6.45 (1H, s, CH—O), 6.54 (1H, s, CH═C), 7.03 (2H, d, J=8.28 Hz, Ar—H), 7.12-7.16 (1H, m, Ar—H), 7.19-7.30 (5H, m, Ar—H), 7.32-7.35 (2H, m, Ar—H), 7.85 (2H, d, J=8.28 Hz, Ar—H).

$^{13}$C NMR (100 MHz, CDCl$_3$): δ 21.74 (CH$_3$), 23.15 (CH$_3$), 24.85 (CH), 39.67 (CH$_2$), 40.45 (CH$_2$), 40.81 (CH$_2$), 43.77 (CH$_2$), 52.03 (OCH$_3$ or CH—N), 53.19 (quat C), 54.38 (CH—N or OCH$_3$), 83.48 (CH—O), 120.70, 123.50, 124.49, 124.62, 125.76, 126.46, 127.07, 128.30, 3×129.25, 129.79, 2×129.94 (13×tert. C and 1×quat. C), 140.21 (quat. C), 142.16 (quat. C), 142.54 (quat. C), 143.65 (quat. C), 144.22 (quat. C), 150.99 (quat. C), 167.03 (C═O), 175.90 (C═O).

Synthesis of ethyl 4-(((1R,2R)-1-(((S)-2-amino-4-methylpentanoyl)oxy)-2,3-dihydro-1H,1'H-[2,2'-biinden]-2-yl)methyl)benzoate (33)

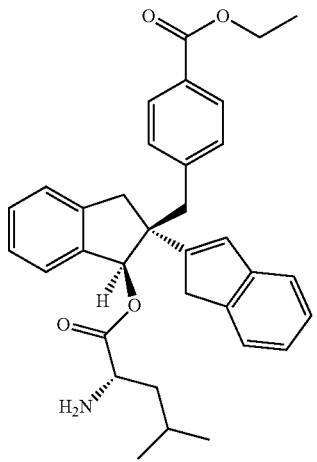 [SMILES: CCOC(=O)c1ccc(C[C@]2(C3=Cc4ccccc4C3)Cc3ccccc3[C@@H]2OC(=O)[C@@H](N)CC(C)C)cc1]

To a solution of ethyl 4-(((1R,2R)-1-hydroxy-2,3-dihydro-1H,1'H-[2,2'-biinden]-2-yl)methyl)benzoate (11, 200 mg, 0.48 mmol), DCC (120 mg, 0.58 mmol) and DMAP (6 mg, 0.048 mmol) in ethyl acetate (10 mL), was added Fmoc leucine (168 mg, 0.48 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (250 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 30% ethyl acetate in petroleum ether as an eluent to yield 150 mg (60%) of the title compound as a colorless semi solid.

LCMS (+H$^+$): observed 524.2, calculated 523.27, molecular formula $C_{34}H_{37}NO_4$ Purity (HPLC): 98%.

$^1$H NMR (400 MHz, CDCl$_3$): δ 0.97 (3H, d, J=6.56 Hz, CH$_3$), 1.01 (3H, d, J=6.64 Hz, CH$_3$), 1.37 (3H, t, J=7.08 Hz, CH$_3$), 1.56-1.60 (1H, m, CH$_2$—CH), 1.66-1.73 (1H, m, CH$_2$—CH), 1.88-1.93 (1H, m, —CH—(CH$_3$)$_2$), 3.06-3.36 (6H, m, 4H of CH and 2H of allylic CH$_2$), 3.62 (1H, dd, J=5.36, 8.92 Hz, CH—N), 4.35 (2H, q, J=7.12 Hz, OCH$_2$), 6.44 (1H, s, CH—O), 6.53 (1H, s, CH═C), 7.02 (2H, d, J=8.20 Hz, Ar—H), 7.10-7.15 (1H, m, Ar—H), 7.18-7.29 (5H, m, Ar—H), 7.31-7.35 (2H, m, Ar—H), 7.85 (2H, d, J=8.20 Hz, Ar—H).

$^{13}$C NMR (100 MHz, CDCl$_3$): δ 14.32 (CH$_3$), 21.74 (CH$_3$), 23.16 (CH$_3$), 24.85 (CH), 39.67 (CH$_2$), 40.47 (CH$_2$), 40.79 (CH$_2$), 43.85 (CH$_2$), 53.22 (quat C), 54.38 (CH—N), 60.86 (OCH$_2$), 83.45 (CH—O), 120.70 (tert. C), 123.50 (tert. C), 124.48 (tert. C), 124.62 (tert. C), 125.75 (tert. C), 126.45 (tert. C), 127.06 (tert. C), 128.65 (quat. C), 3×129.23 (3×tert. C), 129.77 (tert. C), 2×129.88 (2×tert. C), 140.25 (quat. C), 142.17 (quat. C), 142.55 (quat. C), 143.51 (quat. C), 144.24 (quat. C), 151.03 (quat. C), 166.55 (C═O), 176.02 (C═O).

Synthesis of propyl 4-(((1R,2R)-1-(((S)-2-amino-4-methylpentanoyl)oxy)-2,3-dihydro-1H,1'H-[2,2'-biinden]-2-yl)methyl)benzoate (34)

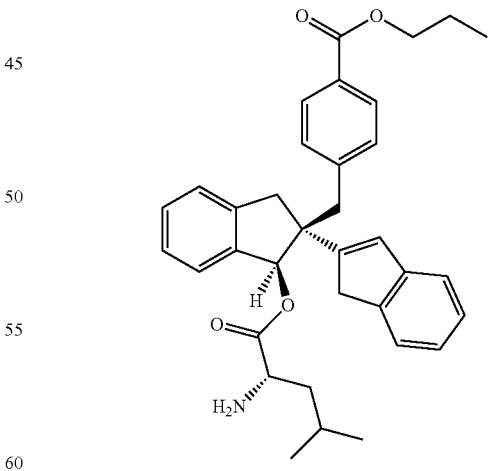

To a solution of propyl 4-(((1R,2R)-1-hydroxy-2,3-dihydro-1H,1'H-[2,2'-biinden]-2-yl)methyl)benzoate (12, 190 mg, 0.44 mmol), DCC (111 mg, 0.54 mmol) and DMAP (6 mg, 0.045 mmol) in ethyl acetate (10 mL), was added Fmoc leucine (158 mg, 0.45 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na₂SO₄. The organic layer was evaporated under reduced pressure and the residue 1 (250 mg) was dissolved in dry THF (6 mL) and cooled to 0° C. Dimethylamine (6 mL, 20% in THF) was added drop wise and the reaction mixture was slowly allowed to stir at room temperature for 1 h. The reaction mixture was evaporated under reduced pressure and the residue was purified by CombiFlash using 30% ethyl acetate in petroleum ether as an eluent to yield 122 mg (51%) of the title compound as a colorless semi solid.

LCMS (+H⁺): observed 538.2, calculated 537.29, molecular formula $C_{35}H_{39}NO_4$ Purity (HPLC): 89%.

¹H NMR (400 MHz, CDCl₃): δ 0.97-1.04 (9H, m, 3×CH₃), 1.56-1.96 (5H, 3×m, 4H of 2×CH₂ and 1H of CH), 3.07-3.38 (6H, m, 6H of 3×CH₂), 3.62-3.68 (1H, m, CH—N), 4.26 (2H, t, J=6.60 Hz, OCH₂), 6.45 (1H, s, CH—O), 6.54 (1H, s, CH=C), 7.03 (2H, d, J=8.28 Hz, Ar—H), 7.12-7.16 (1H, m, Ar—H), 7.18-7.32 (5H, m, Ar—H), 7.34 (2H, dd, J=3.32, 7.34 Hz, Ar—H), 7.86 (2H, d, J=8.24 Hz, Ar—H).

¹³C NMR (100 MHz, CDCl₃): 10.52 (CH₃), 21.74, 22.10, 23.13 (2×CH₃ and 1×CH), 24.84 (CH₂), 39.66 (CH₂), 40.46 (CH₂), 40.77 (CH₂), 43.67 (CH₂), 53.15 (quat. C), 54.36 (CH—N), 66.46 (CH₂—O), 83.56 (CH—O), 120.70 (tert. C), 123.51 (tert. C), 124.48 (tert. C), 124.61 (tert. C), 125.78 (tert. C), 126.45 (tert. C), 127.07 (tert. C), 128.67 (quat. C), 3×129.23 (3×tert. C), 129.79 (tert. C), 2×129.89 (2×tert. C), 140.18 (quat. C), 142.19 (quat. C), 142.56 (quat. C), 143.50 (quat. C), 144.24 (quat. C), 151.02 (quat. C), 166.60 (C=O), 175.69 (C=O).

Synthesis of (1R,2R)-2-(4-carbamoylbenzyl)-2,3-dihydro-1H,1'H-2,2'-biinden-1-yl L-leucinate (35)

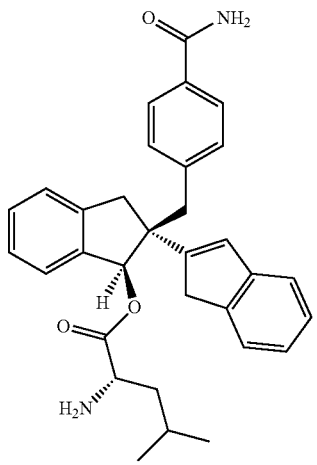 [SMILES: CC(C)C[C@H](N)C(=O)O[C@H]1c2ccccc2C[C@]1(Cc1ccc(C(N)=O)cc1)C1=Cc2ccccc2C1]

To a solution of 4-{[(1'R,2'R)-1'-hydroxy-1',3'-dihydro-1H,2'H-2,2'-biinden-2'-yl]methyl}benzamide (13, 140 mg, 0.36 mmol), DCC (90 mg, 0.44 mmol) and DMAP (4.3 mg, 0.036 mmol) in ethyl acetate (10 mL), was added Fmoc leucine (126 mg, 0.36 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na₂SO₄. The organic layer was evaporated under reduced pressure and the residue 1 (250 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 10% methanol in chloroform as an eluent to yield 110 mg (63%) of the title compound as an off white solid.

LCMS (+H⁺): observed 495.5, calculated 494.26, molecular formula $C_{32}H_{34}N_2O_3$ Purity (HPLC): 91%.

¹H NMR (400 MHz, DMSO-d₆): δ 0.87 (3H, d, J=6.56 Hz, CH₃), 0.91 (3H, d, J=6.64 Hz, CH₃), 1.42-1.48 (1H, m, CH₂—CH), 1.52-1.58 (1H, m, CH₂—CH), 1.72-1.82 (1H, m, CH), 3.04-3.56 (7H, 3×m, 6H of 3×CH₂ and 1H of CH—N), 6.30 (1H, s, CH—O), 6.49 (1H, s, CH=C), 7.00 (2H, d, J=8.20 Hz, Ar—H), 7.08 (1R, dt, J=1.16, 10.15 Hz, Ar—H), 7.16 (1H, t, J=7.28 Hz, Ar—H), 7.21 (2H, t, J=6.48 Hz, Ar—H), 7.25-7.30 (2H, m, Ar—H), 7.34 (2H, t, J=7.80 Hz, Ar—H), 7.65 (2H, d, J=8.20 Hz, Ar—H), 7.84 (1H, br s, NH₂).

¹³C NMR (100 MHz, DMSO-d6): δ 22.33 (CH₃), 23.27 (CH₃), 24.66 (CH), 39.36-40.62 (3×CH₂), 43.51 (CH₂), 53.27 (quat. C), 54.75 (CH—N), 82.79 (CH—O), 120.89 (tert. C), 123.93 (tert. C), 124.65 (tert. C), 125.23 (tert. C), 125.81 (tert. C), 126.70 (tert. C), 127.14 (tert. C), 2×127.45 (2×tert. C), 129.21 (tert. C), 129.44 (tert. C), 2×129.98 (2×tert. C), 132.49 (quat. C), 140.62 (quat. C), 142.08 (quat. C), 142.86 (quat. C), 143.03 (quat. C), 144.44 (quat. C), 152.06 (quat. C), 168.04 (O—C=O), 175.44 (C=O).

Synthesis of (1R,2R)-2-{4-[(2-hydroxyethyl)carbamoyl]benzyl}-2,3-dihydro-1H,1'H-2,2'-biinden-1-yl L-leucinate (36)

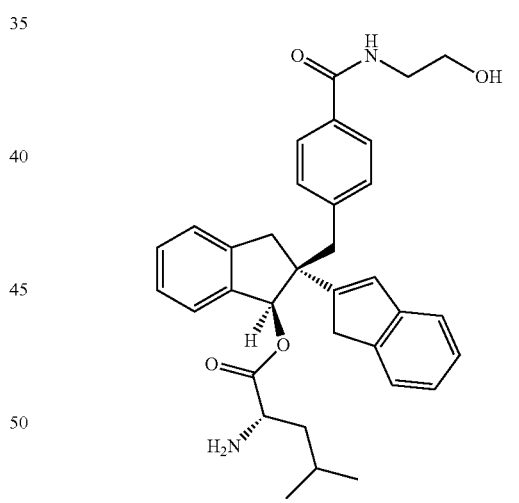

To a solution of 4-{[(1'R,2'R)-1'-(L-leucyloxy)-1',3'-dihydro-1H,2'H-2,2'-biinden-2'-yl]methyl}benzoic acid (24, 130 mg, 0.26 mmol), Et₃N (78 mg, 0.78 mmol) and 2-amino ethanol (24 mg, 0.39 mmol) in DCM (5 mL), was added T₃P (0.33 mL, 50 wt % solution in ethyl acetate, 0.52 mmol) and then stirred at room temperature for 12 h. The reaction mixture was quenched with water (25 mL) and extracted with DCM (3×25 mL). The separated organic layer was washed with brine (25 mL), dried over anhydrous Na₂SO₄ and evaporated under reduced pressure. The residue was purified by CombiFlash using 10% methanol in chloroform as an eluent to yield 70 mg (54%) of the title compound as an off white solid.

LCMS (+H⁺): observed 539.6, calculated 538.28, molecular formula $C_{34}H_{38}N_2O_4$.

Purity (HPLC): 92%.

¹H NMR (400 MHz, DMSO-d₆): δ 0.87 (3H, d, J=6.52 Hz, CH₃), 0.92 (3H, d, J=6.64 Hz, CH₃), 1.38-1.46 (1H, m, CH₂—CH—), 1.50-1.56 (1H, m, CH₂—CH—), 1.74-1.82 (1H, m, CH₂—CH—), 3.03-3.56 (11H, 10H of 5×CH₂ and 1H of CH—N), 4.70 (1H, br s, CH₂—OH), 6.29 (1H, s, CH—O), 6.49 (1H, s, CH=C), 7.00 (2H, d, J=8.24 Hz, Ar—H), 7.09 (1H, dt, J=1.20, 10.16 Hz, Ar—H), 7.15-7.23 (3H, m, Ar—H), 7.27-7.37 (4H, m, Ar—H), 7.64 (2H, d, J=8.24 Hz, Ar—H), 8.31 (1H, t, J=5.64 Hz, NH).

¹³C NMR (100 MHz, DMSO-d₆): 22.33 (CH₃), 23.38 (CH₃), 24.72 (CH), 39.36-40.62 (3×CH₂), 42.55 (CH₂), 44.19 (CH₂), 53.63 (CH—N or quat. C), 54.79 (quat. C or CH—N), 60.20 (CH₂OH), 82.46 (CH—O), 120.88 (tert. C), 123.94 (tert. C), 124.63 (tert. C), 125.21 (tert. C), 125.72 (tert. C), 126.69 (tert. C), 3×127.12 (3×tert. C), 129.17, 129.37, 2×130.01, 132.77 (4×tert. C and 1×quat. C), 140.78 (quat. C), 141.91 (quat. C), 142.76 (quat. C), 143.04 (quat. C), 144.45 (quat. C), 152.12 (quat. C), 166.44 (C=O), 176.37 (C=O).

Synthesis of (1R,2R)-2-[4-(methylcarbamoyl)benzyl]-2,3-dihydro-1H,1'H-2,2'-biinden-1-yl L-leucinate (37)

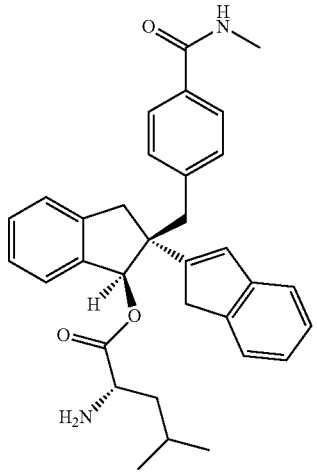 [SMILES: CNC(=O)c1ccc(C[C@]2(C3=Cc4ccccc4C3)Cc3ccccc3[C@@H]2OC(=O)[C@@H](N)CC(C)C)cc1]

To a solution of 4-{[(1'R,2'R)-1'-hydroxy-1',3'-dihydro-1H,2'H-2,2'-biinden-2'-yl]methyl}-N-methylbenzamide (15, 150 mg, 0.38 mmol), DCC (94 mg, 0.45 mmol) and DMAP (5 mg, 0.038 mmol) in ethyl acetate (10 mL), was added Fmoc leucine (133 mg, 0.38 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na₂SO₄. The organic layer was evaporated under reduced pressure and the residue 1 (250 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 10% methanol in chloroform as an eluent to yield 100 mg (52%) of the title compound as an off white solid.

LCMS (+H⁺): observed 509.5, calculated 508.27, molecular formula $C_{33}H_{36}N_2O_3$ Purity (HPLC): 99%.

¹H NMR (400 MHz, CDCl₃): δ 0.95 (3H, d, J=6.52 Hz, CH₃), 0.98 (3H, d, J=6.52 Hz, CH₃), 1.60-1.76 (2H, m, CH₂—CH), 1.86-1.96 (1H, m, CH), 2.97 (3H, d, J=4.80 Hz, NH—CH₃), 3.04-3.36 (6H, m, 3×CH₂), 3.62-3.68 (1H, m, CH—N), 6.08-6.14 (1H, m, NH—CH₃), 6.45 (1H, s, CH—O), 6.51 (1H, s, CH=C), 7.00 (2H, d, J=8.20 Hz, Ar—H), 7.09-7.19 (2H, m, Ar—H), 7.21-7.29 (4H, m, Ar—H), 7.32 (2H, d, J=6.84 Hz, Ar—H), 7.50-7.56 (2H, m, Ar—H).

¹³C NMR (100 MHz, CDCl₃): δ 21.74 (CH₃), 23.14 (CH₃), 24.84 (CH₃—N or CH), 26.80 (CH or CH₃—N), 39.67 (CH₂), 40.46 (CH₂), 40.64 (CH₂), 43.74 (CH₂), 53.17 (quant. C), 54.38 (CH—N), 83.48 (CH—O), 120.68 (tert. C), 123.51 (tert. C), 124.47 (tert. C), 124.63 (tert. C), 125.75 (tert. C), 126.45 (tert. C), 2×126.52 (2×tert. C), 127.06 (tert. C), 129.25 (tert. C), 129.75 (tert. C), 2×130.06 (2×tert. C), 132.66 (quat. C), 140.22 (quat. C), 141.84 (quat. C), 142.21 (quat. C), 142.56 (quat. C), 144.25 (quat. C), 151.10 (quat. C), 168.03 (C=O).

Synthesis of (1R,2R)-2-[4-(dimethylcarbamoyl)benzyl]-2,3-dihydro-1H,1'H-2,2'-biinden-1-yl L-leucinate (38)

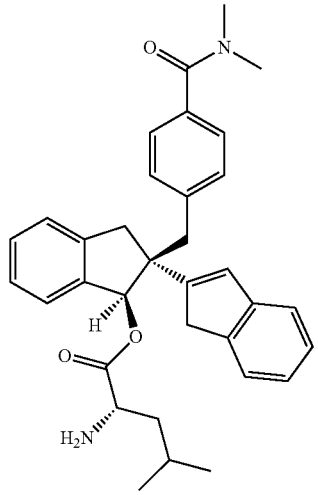 [SMILES: CC(C)C[C@H](N)C(=O)O[C@H]1c2ccccc2C[C@]1(Cc1ccc(C(=O)N(C)C)cc1)C1=Cc2ccccc2C1]

To a solution of 4-{[(1R,2'R)-1'-hydroxy-1',3'-dihydro-1H,2'H-2,2'-biinden-2'-yl]methyl}-N,N-dimethylbenzamide (16, 185 mg, 0.45 mmol), DCC (112 mg, 0.54 mmol) and DMAP (6 mg, 0.045 mmol) in ethyl acetate (10 mL), was added Fmoc leucine (158 mg, 0.45 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na₂SO₄. The organic layer was evaporated under reduced pressure and the residue 1 (250 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 10% methanol in chloroform as an eluent to yield 120 mg (51%) of the title compound as an off white solid.

LCMS (+H⁺): observed 523.2, calculated 522.29, molecular formula $C_{34}H_{38}N_2O_3$ Purity (HPLC): 95%.

¹H NMR (400 MHz, CDCl₃): δ 0.97 (3H, d, J=6.52 Hz, CH₃), 1.01 (3H, d, J=6.56 Hz, CH₃), 1.60-1.94 (3H, 3×m, 1H of

CH and 2H of CH₂—CH), 2.92 (3H, s, N—CH₃), 3.05-3.36 (9H, m, 6H of 3×CH₂ and 3H of N—CH₃), 3.63-3.67 (1H, m, CH—N), 6.43 (1H, s, CH—O), 6.53 (1H, s, CH═C), 6.97 (2H, d, J=8.00 Hz, Ar—H), 7.10-7.14 (1H, m, Ar—H), 7.18-7.28 (7H, m, Ar—H), 7.30-7.35 (2H, m, Ar—H).

¹³C NMR (100 MHz, CDCl₃): δ 21.76 (CH₃), 23.14 (CH₃), 24.85 (CH), 39.70, 40.29 and 40.57 (2×CH₂ and 1×N—CH₃), 43.61 (CH₂), 53.13 (quat. C), 54.42 (CH—N), 83.62 (CH—O), 120.66 (tert. C), 123.48 (tert. C), 124.42 (tert. C), 124.61 (tert. C), 125.72 (tert. C), 126.43 (tert. C), 2×126.89 (2×tert. C), 127.01 (tert. C), 129.20 (tert. C), 129.72 (quat. C), 2×129.82 (2×tert. C), 134.25 (quat. C), 139.75 (quat. C), 140.19 (quat. C), 142.26 (quat. C), 142.60 (quat. C), 144.31 (quat. C), 151.23 (quat. C), 171.54 (C═O).

Synthesis of methyl 4-((1S,2S)-1-(((S)-2-amino-4-methylpentanoyl)oxy)-2,3-dihydro-1H,1'H-[2,2'-biinden]-2-yl)methyl)benzoate (39)

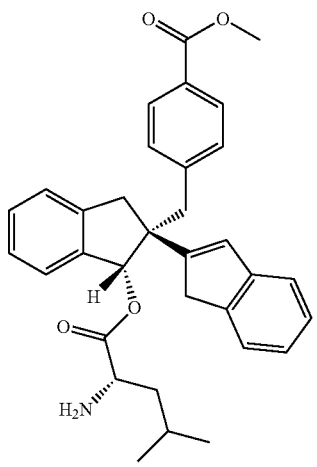 [SMILES: COC(=O)c1ccc(C[C@@]2(C3=Cc4ccccc4C3)Cc3ccccc3[C@H]2OC(=O)[C@@H](N)CC(C)C)cc1]

To a solution of methyl 4-(((1S,2S)-1-hydroxy-2,3-dihydro-1H,1'H-[2,2'-biinden]-2-yl)methyl)benzoate (17, 200 mg, 0.50 mmol), DCC (125 mg, 0.60 mmol) and DMAP (6 mg, 0.045 mmol) in ethyl acetate (10 mL), was added Fmoc leucine (176 mg, 0.50 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na₂SO₄. The organic layer was evaporated under reduced pressure and the residue 1 (220 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 30% ethyl acetate in petroleum ether as an eluent to yield 150 mg (60%) of the title compound as a colorless semi solid.

LCMS (+H⁺): observed 510.2, calculated 509.26, molecular formula C₃₃H₃₅NO₄

Purity (HPLC): 96%.

¹H NMR (400 MHz, CDCl₃): δ 0.93 (3H, d, J=6.44 Hz, CH₃), 0.94 (3H, d, J=5.20 Hz, CH₃), 1.54-1.80 (3H, 2×m, 2H of CH₂—CH and 1H of CH₂CH), 3.05-3.39 (6H, m, 3×CH₂), 3.70-3.74 (1H, m, CH—N), 3.89 (3H, s, OCH₃), 6.42 (1H, s, CH—O), 6.51 (1H, s, CH═C), 7.01 (2H, d, J=8.32 Hz, Ar—H), 7.11-7.16 (1H, m, Ar—H), 7.18-7.31 (6H, m, Ar—H), 7.36 (1H, d, J=7.28 Hz, Ar—H), 7.84 (2H, d, J=8.28 Hz, Ar—H).

¹³C NMR (100 MHz, CDCl₃): δ 21.95 (CH₃), 22.78 (CH₃), 24.77 (CH), 39.62 (CH₂), 40.37 (CH₂), 40.73 (CH₂), 43.69 (CH₂), 52.02, 52.96 and 54.40 (OCH₃, quat C and CH—N), 83.54 (CH—O), 120.71, 123.54, 124.49, 124.64, 125.59, 126.45, 127.04, 128.28, 3×129.21, 129.77, 2×130.00 (13× tert. C and 1×quat. C), 140.06 (quat. C), 142.06 (quat. C), 142.56 (quat. C), 143.62 (quat. C), 144.22 (quat. C), 150.94 (quat. C), 167.04 (C═O), 175.51 (C═O).

Synthesis of ethyl 4-(((1S,2S)-1-(((S)-2-amino-4-methylpentanoyl)oxy)-2,3-dihydro-1H,1'H-[2,2'-biinden]-2-yl)methyl)benzoate (40)

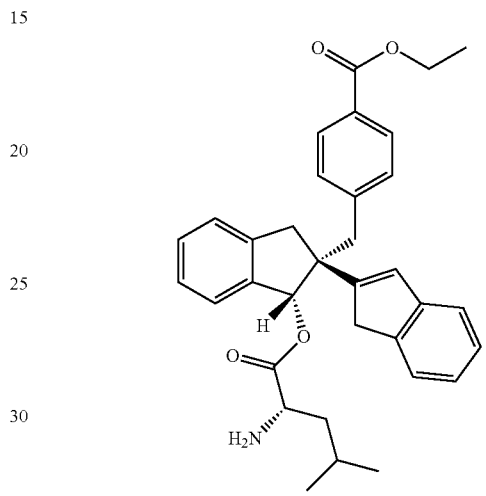

To a solution of ethyl 4-(((1S,2S)-1-hydroxy-2,3-dihydro-1H,1'H-[2,2'-biinden]-2-yl)methyl)benzoate (18, 200 mg, 0.48 mmol), DCC (120 mg, 0.58 mmol) and DMAP (6 mg, 0.048 mmol) in ethyl acetate (10 mL), was added Fmoc leucine (161 mg, 0.48 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na₂SO₄. The organic layer was evaporated under reduced pressure and the residue 1 (250 mg) was dissolved in dry THF (6 mL) and cooled to 0° C. Dimethylamine (6 mL, 20% in THF) was added drop wise and the reaction mixture was slowly allowed to stir at room temperature for 1 h. The reaction mixture was evaporated under reduced pressure and the residue was purified by CombiFlash using 30% ethyl acetate in petroleum ether as an eluent to yield 140 mg (55%) of the title compound as a colorless semi solid.

LCMS (+H⁺): observed 524.2, calculated 523.27, molecular formula C₃₄H₃₇NO₄

Purity (HPLC): 98%.

¹H NMR (400 MHz, CDCl₃): δ 0.89-0.94 (6H, m, (CH₃)₂), 1.37 (3H, t, J=6.80 Hz, CH₃), 1.64-1.80 (3H, m, 1H of CH and 2H of CH₂—CH), 3.02-3.16 (2H, m, CH₂), 3.20-3.36 (4H, m, 2×CH₂), 3.82-3.86 (1H, m, CH—N), 4.34 (2H, q, J=7.20 Hz, OCH₂), 6.41 (1H, s, CH-0), 6.49 (1H, s, CH═C), 6.99 (2H, d, J=8.00 Hz, Ar—H), 7.11-7.15 (1H, m, Ar—H), 7.16-7.30 (6H, m, Ar—H), 7.36 (1H, d, J=7.60 Hz, Ar—H), 7.83 (2H, d, J=8.40 Hz, Ar—H).

¹³C NMR (100 MHz, CDCl₃): δ 14.31 (CH₃), 21.95 (CH₃), 22.80 (CH₃), 24.78 (CH), 39.62 (CH₂), 40.39 (CH₂), 40.70 (CH₂), 43.86 (CH₂), 52.99 (quat C), 54.40 (CH—N), 60.87 (CH₂—O), 83.49 (CH—O), 120.71 (tert. C), 123.54 (tert. C), 124.48 (tert. C), 124.64 (tert. C), 125.57 (tert. C), 126.45 (tert.

C), 127.03 (tert. C), 128.62 (quat. C), 3×129.18 (3×tert. C), 129.74 (tert. C), 2×129.94 (2×tert. C), 140.10 (quat. C), 142.06 (quat. C), 142.57 (quat. C), 143.49 (quat. C), 144.24 (quat. C), 150.99 (quat. C), 166.58 (C=O), 175.80 (C=O).

Synthesis of propyl 4-(((1S,2S)-1-(((S)-2-amino-4-methylpentanoyl)oxy)-2,3-dihydro-1H,1'H-[2,2'-biinden]-2-yl)methyl)benzoate (41)

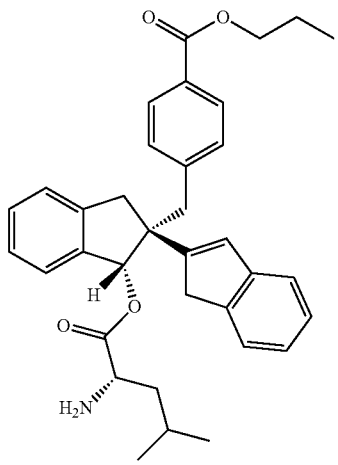 [SMILES: CCCOC(=O)c1ccc(C[C@@]2(C3=Cc4ccccc4C3)Cc3ccccc3[C@H]2OC(=O)[C@@H](N)CC(C)C)cc1]

To a solution of propyl 4-(((1S,2S)-1-hydroxy-2,3-dihydro-1H,1'H-[2,2'-biinden]-2-yl)methyl)benzoate (19, 180 mg, 0.42 mmol), DCC (105 mg, 0.50 mmol) and DMAP (6 mg, 0.042 mmol) in ethyl acetate (10 mL), was added Fmoc leucine (148 mg, 0.42 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (210 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 30% ethyl acetate in petroleum ether as an eluent to yield 120 mg (53%) of the title compound as a colorless semi solid.

LCMS (+H+): observed 538.5, calculated 537.29, molecular formula $C_{35}H_{39}NO_4$ Purity (HPLC): 95%

$^1$H NMR (400 MHz, CDCl$_3$): δ 0.93 (3H, d, J=4.12 Hz, CH$_3$), 0.94 (3H, d, J=4.12 Hz, (CH$_3$), 1.03 (3H, t, J=8.00 Hz, CH$_3$), 1.49-1.81 (5H, m, 1H of CH and 4H of 2×CH$_2$), 3.07-3.41 (6H, m, 3×CH$_2$), 3.64-3.67 (1H, m, CH—N), 4.26 (2H, t, J=8.00 Hz, OCH$_2$), 6.42 (1H, s, CH—O), 6.53 (1H, s, CH=C), 7.01 (2H, d, J=8.00 Hz, Ar—H), 7.13-7.17 (1H, m, Ar—H), 7.20-7.32 (6H, m, Ar—H), 7.37 (1H, d, J=4.00 Hz, Ar—H), 7.86 (2H, d, J=8.00 Hz, Ar—H).

$^{13}$C NMR (100 MHz, CDCl$_3$): δ 10.53 (CH$_3$), 21.93 (CH$_3$), 22.09 (CH$_3$), 22.87 (CH), 24.80 (CH$_2$), 39.61 (CH$_2$), 40.43 (CH$_2$), 40.68 (CH$_2$), 44.24 (CH$_2$), 53.12 (quat. C), 54.39 (CH—N), 66.47 (CH$_2$—O), 83.31 (CH—O), 120.72 (tert. C), 123.53 (tert. C), 124.48 (tert. C), 124.64 (tert. C), 125.54 (tert. C), 126.46 (tert. C), 127.02 (tert. C), 128.65 (quat. C), 129.15 (tert. C), 2×129.19 (2×tert. C), 129.71 (tert. C), 2×129.93 (2×tert. C), 140.18 (quat. C), 142.01 (quat. C), 142.57 (quat. C), 143.51 (quat. C), 144.26 (quat. C), 151.05 (quat. C), 166.64 (O—C=O), 176.39 (C=O).

Synthesis of (1S,2S)-2-(4-carbamoylbenzyl)-2,3-dihydro-1H,1'H-2,2'-biinden-1-yl L-leucinate (42)

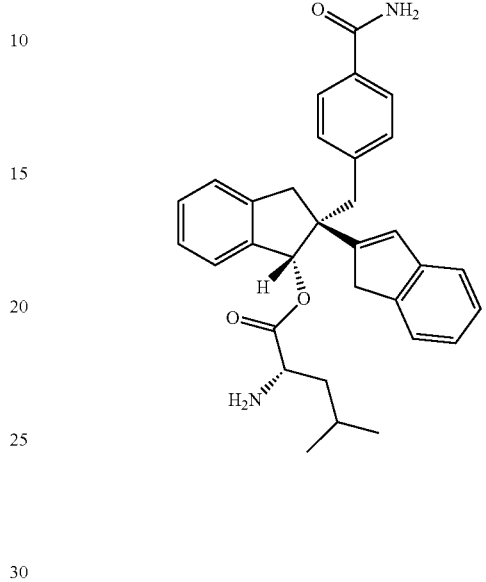

To a solution of 4-{[(1'S,2'S)-1'-hydroxy-1',3'-dihydro-1H,2'H-2,2'-biinden-2'-yl]methyl}benzamide (20, 150 mg, 0.26 mmol), DCC (64 mg, 0.31 mmol) and DMAP (3 mg, 0.026 mmol) in ethyl acetate (10 mL), was added Fmoc leucine (91 mg, 0.26 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue 1 (180 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 10% methanol in chloroform as an eluent to yield 110 mg (86%) of the title compound as an off white solid.

LCMS (+H+): observed 495.2, calculated 494.26, molecular formula $C_{32}H_{34}N_2O_3$ Purity (HPLC): 97%.

$^1$H NMR (400 MHz, DMSO-d$_6$): δ 0.85 (3H, d, J=6.20 Hz, CH$_3$), 0.87 (3H, d, J=6.20 Hz, CH$_3$), 1.40-1.74 (3H, 2×m, 2H of CH$_2$—CH and 1H of CH—CH$_2$), 3.04 (1H, d, J=13.44 Hz, CH$_2$), 3.11-3.28 (4H, m, 2×CH$_2$), 3.48-3.56 (2H, m, 1H of CH$_2$ and CH—N), 6.27 (1H, s, CH—O), 6.49 (1H, s, CH=C), 6.99 (2H, d, J=8.20 Hz, Ar—H), 7.09 (1H, dt, J=1.20, 10.16 Hz, Ar—H), 7.15-7.38 (8H, m, 7H×Ar—H and 1H of NH$_2$), 7.66 (2H, d, J=8.24 Hz, Ar—H), 7.84 (1H, br s, $^{13}$C NMR (100 MHz, DMSO-d$_6$): 22.50 (CH$_3$), 23.18 (CH$_3$), 24.71 (CH), 39.35-40.60 (2×CH$_2$), 44.30 (CH$_2$), 53.26 (quat. C), 54.80 (CH—N), 82.43 (CH—O), 120.89 (tert. C), 123.95 (tert. C), 124.62 (tert. C), 125.22 (tert. C), 125.57 (tert. C), 126.69 (tert. C), 127.14 (quat. C), 2×127.41 (2×tert. C), 129.14 (tert. C), 129.34 (tert. C), 2×130.05 (2×tert. C), 132.47

(tert. C), 140.70 (quat. C), 142.10 (quat. C), 142.73 (quat. C), 143.08 (quat. C), 144.47 (quat. C), 152.17 (quat. C), 168.06 (N—C=O), 176.56 (C=O).

Synthesis of (1S,2S)-2-{4-[(2-Hydroxyethyl)carbamoyl]benzyl}-2,3-dihydro-1H,1'H-2,2'-biinden-1-yl leucinate (43)

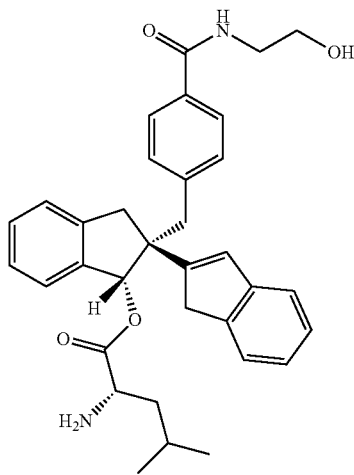 [SMILES: CC(C)C[C@H](N)C(=O)O[C@@H]1c2ccccc2C[C@@]1(Cc1ccc(C(=O)NCCO)cc1)C1=Cc2ccccc2C1]

To a solution of 4-{[(1'S,2'S)-1'-Hydroxy-1',3'-dihydro-1H,2'H-2,2'-biinden-2'-yl]methyl}-N-(2-hydroxyethyl)benzamide (21, 300 mg, 0.79 mmol) and 2,4,6-trimethyl pyridine (85 mg, 0.79 mmol) in DCM (10 mL) was added acetyl chloride (62 mg, 0.79 mmol) at −78° C. and then slowly allowed to warm to room temperature over a period of 1 h. Reaction mixture was quenched with ice (25 mL) and extracted with DCM (3×25 mL). The organic layer was washed with brine (25 mL), dried over anhydrous $Na_2SO_4$ and evaporated under reduced pressure. The residue was purified by CombiFlash using 20% ethyl acetate in chloroform as an eluent to yield 250 mg (68%) of the intermediate 1 as an off white solid.

LCMS (+H$^+$): observed 468.4, calculated 467.56, molecular formula $C_{30}H_{29}NO_4$ Purity (UPLC): 99%.

$^1$H NMR (400 MHz, CDCl$_3$): δ 2.10 (3H, s, CH$_3$), 2.83 (1H, d, J=13.20 Hz, CH$_2$), 3.01-3.03 (2H, m CH$_2$), 3.26 (1H, d, J=13.20 Hz, CH$_2$), 3.46 (1H, d, J=22.40 Hz, CH$_2$), 3.58 (1H, d, J=22.80 Hz, CH$_2$), 3.69-3.73 (2H, m, CONHCH$_2$), 4.28 (2H, t, J=5.60 Hz, CH$_2$OCH$_3$), 5.25 (1H, d, J=7.60 Hz, CH—OH), 6.44 (1H, m, CH—OH or NH), 6.47 (1H, s, CH=C), 6.97 (2H, d, J=8.00 Hz, Ar—H), 7.17 (1H, dt, J=2.00, 9.87 Hz, Ar—H), 7.26-7.32 (5H, m, Ar—H), 7.44 (2H, d, J=6.40 Hz, Ar—H), 7.57 (2H, d, J=8.40 Hz, Ar—H).

To a solution of 2-[(4-{[(1'S,2'S)-1'-Hydroxy-1',3'-dihydro-1H,2'H-2,2'-biinden-2'-yl]methyl}benzoyl)amino]ethyl acetate (intermediate 1, 250 mg, 0.53 mmol), DCC (142 mg, 0.62 mmol) and DMAP (7 mg, 0.053 mmol) in ethyl acetate (10 mL), was added N-[(9H-fluoren-9-ylmethoxy)carbonyl] leucine (226 mg, 0.53 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous $Na_2SO_4$. The organic layer was evaporated under reduced pressure and the residue was purified by CombiFlash using 20% ethyl acetate in chloroform as an eluent to yield 320 mg (76%) of the intermediate 2 as an off white solid.

LCMS (+H$^+$): observed 803.4, calculated 802.95, molecular formula $C_{51}H_{50}N_2O_7$ Purity (UPLC): 96%.

$^1$H NMR (400 MHz, CDCl$_3$): δ 0.93 (6H, d, J=5.53 Hz, CH(CH$_3$)$_2$), 1.46-1.78 (3H, 3×m, CH$_2$—CH—), 2.07 (3H, s, COCH$_3$), 3.06-3.41 (6H, m, 3×CH$_2$), 3.66-3.70 (2H, m, CONHCH$_2$), 4.22-4.27 (3H, m, CH$_2$OCOCH$_3$ and CH—CH$_2$O), 4.42-4.46 (2H, m, CH—CH$_2$O), 4.49-4.54 (1H, m, CH—NH), 5.21 (1H, d, J=8.92 Hz, CH—NH), 6.41-6.43 (2H, m, CH—O and CH$_2$NHCO), 6.51 (1H, s, CH=C), 6.98 (2H, d, J=8.20 Hz, Ar—H), 7.11-7.14 (1H, m, Ar—H), 7.19-7.25 (4H, m, Ar—H), 7.30-7.34 (5H, m, Ar—H), 731 (2H, t, J=7.68 Hz, Ar—H), 7.54 (2H, d, J=8.32 Hz, Ar—H), 7.59-7.63 (2H, m, Ar—H), 7.78 (2H, d, J=7.24 Hz, Ar—H).

To a solution of (1S,2S)-2-(4-{[2-(Acetyloxy)ethyl]carbamoyl}benzyl)-2,3-dihydro-1H,1'H-2,2'-biinden-1-yl N-[(9H-fluoren-9-ylmethoxy)carbonyl]leucinate (intermediate 2, 320 mg, 0.40 mmol) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 10% methanol in chloroform as an eluent to yield 160 mg of the material [38% product mass (581.5) in UPLC] as a solid. The solid was dissolved in THF:H$_2$O (1:1, 10 mL) was added lithium hydroxide dihydrate (6 mg, 0.27 mmol) at 0° C. and then stirred at room temperature for 1 h. The reaction mixture was neutralized with 1.5 N HCl (P$^H$ 7.0) and then extracted with ethyl acetate (3×10 mL), washed with 10% aqueous NaHCO$_3$ (10 mL) followed by brine (10 mL). Organic layer was dried over anhydrous Na$_2$SO$_4$, evaporated under reduced pressure and the residue was purified by CombiFlash using 10% methanol in chloroform as an eluent to yield 35 mg (21%) of the title compound as an off white solid.

LCMS (+H$^+$): observed 540.3, calculated 538.68, molecular formula $C_{34}H_{38}N_2O_4$ Purity (HPLC): 95%.

$^1$H NMR (400 MHz, CDCl$_3$): δ 0.92-0.94 (6H, m, CH(CH$_3$)$_2$), 1.46-1.78 (3H, 3×m, CH$_2$—CH—), 3.06-3.13 (2H, m, CH$_2$), 3.18-3.27 (3H, m, 1H of CH$_2$ and 2H of allylic CH$_2$), 3.37 (1H, d, J=22.40 Hz, CH$_2$), 3.58-3.65 (3H, m, CONHCH$_2$ and CH—NH$_2$), 3.82 (2H, t, J=5.20 Hz, CH$_2$OH), 6.41 (1H, s, CH—O), 6.52 (1H, s, CH=C), 6.61 (1H, t, J=5.20 Hz, CONH or CH$_2$OH), 7.00 (2H, d, J=8.40 Hz, Ar—H), 7.12-7.19 (1H, m, Ar—H), 7.15-7.31 (6H, m, Ar—H), 7.36 (1H, d, J=7.20 Hz, Ar—H), 7.59 (2H, d, J=8.40 Hz, Ar—H).

$^{13}$C NMR (100 MHz, CDCl$_3$): 21.94 (CH$_3$), 22.85 (CH$_3$), 24.79 (CH), 29.27 (CH$_2$), 39.61 (CH$_2$), 40.59 (CH$_2$), 42.82 (CH$_2$), 44.19 (CH$_2$), 53.08 (quat. C), 54.39 (CH—N), 62.44 (CH$_2$OH), 83.26 (CH—O), 12032 (tert. C), 123.54 (tert. C), 124.49 (tert. C), 124.65 (tert. C), 125.54 (tert. C), 126.47 (tert. C), 2×126.66 (2×tert. C), 127.03 (tert. C), 129.18 (tert. C), 129.70 (tert. C), 2×130.13 (2×tert. C), 132.18 (quat. C), 140.18 (quat. C), 142.01 (quat. C), 142.24 (quat. C), 142.55 (quat. C), 144.25 (quat. C), 151.07 (quat. C), 168.36 (C=O), 176.27 (C=O).

Synthesis of (1S,2S)-2-[4-(methylcarbamoyl)benzyl]-2,3-dihydro-1H,1'H-2,2'-biinden-1-yl L-leucinate (44)

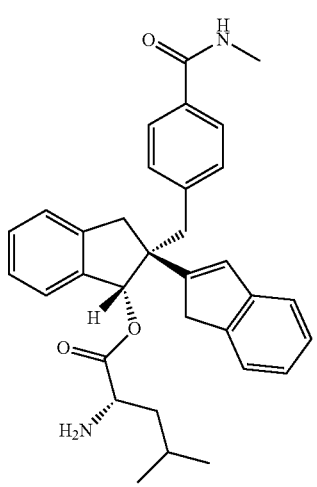 [SMILES: CNC(=O)c1ccc(C[C@@]2(C3=Cc4ccccc4C3)Cc3ccccc3[C@H]2OC(=O)[C@@H](N)CC(C)C)cc1]

To a solution of 4-{[(1'S,2'S)-1'-hydroxy-1',3'-dihydro-1H,2'H-2,2'-biinden-2'-yl]methyl}-N-methylbenzamide (22, 150 mg, 0.38 mmol), DCC (94 mg, 0.45 mmol) and DMAP (5 mg, 0.038 mmol) in ethyl acetate (10 mL), was added Fmoc leucine (134 mg, 0.38 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na$_2$SO$_4$. The organic layer was evaporated under reduced pressure and the residue 1 (180 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 10% methanol in chloroform as an eluent to yield 75 mg (39%) of the title compound as an off white solid.

LCMS (+H$^+$): observed 509.5, calculated 508.27, molecular formula C$_{33}$H$_{36}$N$_2$O$_3$ Purity (HPLC): 97%.

$^1$H NMR (400 MHz, DMSO-d$_6$): δ 0.85 (3H, d, J=6.00 Hz, CH$_3$), 0.87 (3H, d, J=6.40 Hz, CH$_3$), 1.39-1.72 (3H, 2×m, 2H of CH$_2$—CH and 1H of CH—CH$_2$), 2.73 (3H, d, J=4.40 Hz, CH$_3$), 3.04 (1H, d, J=13.60 Hz, CH$_2$), 3.15 (1H, t, J=26.80 Hz, CH$_2$), 3.23-3.27 (3H, m, 3H of 2×CH$_2$), 3.49-3.55 (2H, m, 1H of CH and 1H of CH—N), 6.27 (1H, s, CH—O), 6.48 (1H, s, CH=C), 6.99 (2H, d, J=8.40 Hz, Ar—H), 7.09 (1H, dt, J=1.20, 10.27 Hz, Ar—H), 7.15-7.25 (4H, m, Ar—H), 7.27-7.37 (3H, m, Ar—H), 7.61 (2H, d, J=8.40 Hz, Ar—H), 8.31 (1H, d, J=4.40 Hz, NH).

Synthesis of (1S,2S)-2-[4-(dimethylcarbamoyl)benzyl]-2,3-dihydro-1H,1'H-2,2'-biinden-1-yl L-leucinate (45)

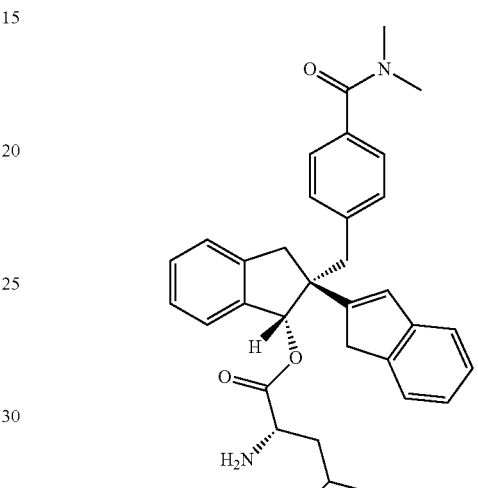

To a solution of 4-{[(1'S,2'S)-1'-hydroxy-1',3'-dihydro-1H,2'H-2,2'-biinden-2'-yl]methyl}-N,N-dimethylbenzamide (23, 100 mg, 0.24 mmol), DCC (56 mg, 0.28 mmol) and DMAP (3 mg, 0.024 mmol) in ethyl acetate (5 mL), was added Fmoc leucine (84 mg, 0.24 mmol) and then stirred at room temperature for 12 h. The solids were filtered, washed with ethyl acetate (25 ml) and the combined filtrate was washed with 1.5 N HCl (25 mL), water (25 mL), brine (10 mL), dried over anhydrous Na$_2$SO$_4$. The organic layer was evaporated under reduced pressure and the residue 1 (140 mg) was dissolved in dry THF (5 mL) and cooled to 0° C. Dimethylamine (5 mL, 20% in THF) was added drop wise and the reaction mixture was slowly allowed to stir at room temperature for 1 h. The reaction mixture was evaporated under reduced pressure and the residue was purified by CombiFlash using 10% methanol in chloroform as an eluent to yield 45 mg (36%) of the title compound as an off white solid.

LCMS (+H$^+$): observed 523.5, calculated 522.29, molecular formula C$_{34}$H$_{38}$N$_2$O$_3$ Purity (HPLC): 97%.

$^1$H NMR (400 MHz, DMSO-d$_6$): δ 0.82-0.87 (6H, m, 2×CH$_3$), 1.58-1.66 (3H, m, 2H of CH$_2$CH and 1H of CH$_2$CH), 2.83 (3H, s, N—CH$_3$), 2.93 (3H, s, N—CH$_3$), 3.11 (1H, d, J=13.20 Hz, CH$_2$), 3.18-3.30 (4H, m, 2×CH$_2$), 3.45 (1H, d, J=22.80 Hz, CH$_2$), 4.26-4.30 (1H, m, CH—N), 6.36 (1H, s, CH—O), 6.55 (1H, s, CH=C), 7.00 (2H, d, J=8.00 Hz, Ar—

H), 7.09 (1H, dt, J=1.20, 10.00 Hz, Ar—H), 7.15-7.23 (5H, m, Ar—H), 7.27-7.37 (4H, m, Ar—H), 8.47 (2H, br s, NH₂).

Synthesis of 2-hydroxy-5-(4-((((1R,2R)-1-hydroxy-2,3-dihydro-1H,1'H-[2,2'-biinden]-2-yl)methyl)benzamido)benzoic acid (46)

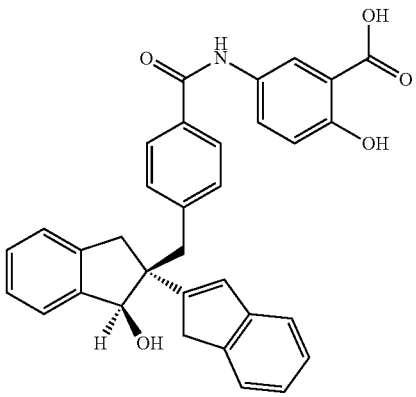 [SMILES: O=C(Nc1ccc(O)c(C(=O)O)c1)c1ccc(C[C@]2(C3=Cc4ccccc4C3)Cc3ccccc3[C@@H]2O)cc1]

To a mixture of ethyl 4-((((1R,2R)-1-hydroxy-2,3-dihydro-1H,1'H-[2,2'-biinden]-2-yl)methyl)benzoate (11, 200 mg, 0.48 mmol), 5-amino-2-hydroxybenzoic acid (75 mg, 0.48 mmol) and THF (1.0 mL) in a 5 mL microwave vial, was added trimethylaluminium (0.5 mL, 20% solution in toluene) and the mixture irradiated at 100° C. for 5 min. The reaction mixture was quenched with slow addition of 1.5 N HCl (2 mL) and extracted with ethyl acetate (3×15 mL). Organic layer was washed with water (25 mL), brine (25 mL), dried over anhydrous Na₂SO₄ and evaporated under reduced pressure. The residue purified by preparative HPLC [Kromasil C18 (250×50 mm), flow rate: 40 mL/min, 0.1% TFA in water/MeOH, run time: 40 min] to yield 75 mg (30%) of the title compound as an off white solid.

LCMS (+H⁺): observed 518.4, calculated 517.19, molecular formula C₃₃H₂₇NO₅.

Purity (HPLC): 90%.

¹H NMR (400 MHz, DMSO-d₆): δ 2.72 (1H, d, J=13.64 Hz, —CH₂—), 2.97 (1H, d, J=17.20 Hz, —CH₂—), 3.01 (1H, d, J=16.36 Hz, —CH₂—), 3.23 (1H, d, J=13.64 Hz, —CH₂), 3.50 (1H, d, J=23.16 Hz, CH₂), 3.65 (1H, d, J=23.16 Hz, CH₂), 5.07 (1H, s, CH—OH), 5.87 (1H, br s, CH—OH), 6.44 (1H, s, CH=C), 6.87 (1H, d, J=8.88 Hz, Ar—H), 6.97 (2H, d, J=8.20 Hz, Ar—H), 7.10 (1H, t, J=7.28 Hz, Ar—H), 7.16-7.21 (1H, m, Ar—H), 7.23-7.29 (4H, m, Ar—H), 7.37 (1H, t, J=3.52 Hz, Ar—H), 7.42 (1H, d, J=7.28 Hz, Ar—H), 7.73 (2H, d, J=8.20 Hz, Ar—H), 7.77 (1H, dd, J=2.68, 8.90 Hz, Ar—H), 8.18 (1H, d, J=2.64 Hz, Ar—H), 10.05 (1H, s, Ar—OH or O=C—OH).

¹³C NMR (100 MHz, DMSO-d₆): δ 39.34-40.59 (3×CH₂), 56.23 (quat C), 81.49 (CH—OH), 117.10, 120.64, 122.41, 123.94, 124.27, 124.80, 124.92, 126.58, 126.81, 2×127.38, 127.67, 128.05, 128.30, 3×130.21, 130.81, 132.74 (16×tert. C and 3×quat. C), 140.77 (quat. C), 143.39 (quat. C), 143.42 (quat. C), 144.88 (quat. C), 145.53 (quat. C), 154.46 (quat. C), 158.14 (quat. C), 165.36 (N—C=O), 172.15 (O—C=O).

Synthesis of 2-hydroxy-5-(4-((((1S,2S)-1-hydroxy-2,3-dihydro-1H,1'H-[2,2'-biinden]-2-yl)methyl)benzamido)benzoic acid (47)

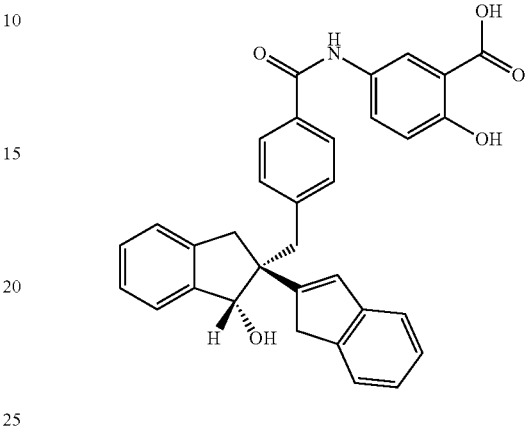

To a mixture of ethyl 4-((((1S,2S)-1-hydroxy-2,3-dihydro-1H, 1'H-[2,2'-biinden]-2-yl)methyl)benzoate (18, 200 mg, 0.48 mmol), 5-amino-2-hydroxybenzoic acid (75 mg, 0.48 mmol) and THF (1.0 mL) in a 5 mL microwave vial, was added trimethylaluminium (0.5 mL, 20% solution in toluene) and the mixture irradiated at 100° C. for 5 min. The reaction mixture was quenched with slow addition of 1.5 N HCl (2 mL) and extracted with ethyl acetate (3×15 mL). Organic layer was washed with water (25 mL), brine (25 mL), dried over anhydrous Na₂SO₄ and evaporated under reduced pressure. The residue purified by preparative HPLC [Kromasil C18 (250×50 mm), flow rate: 40 mL/min, 0.1% TFA in water/MeOH, run time: 40 min] to yield 90 mg (36%) of the title compound as an off white solid.

LCMS (−H⁺): observed 516.0, calculated 517.19, molecular formula C₃₃H₂₇NO₅.

Purity (HPLC): 89%.

¹H NMR (400 MHz, DMSO-d₆): δ 2.72 (1H, d, J=13.64 Hz, CH₂), 2.97 (1H, d, J=16.92 Hz, CH₂), 3.01 (1H, d, J=16.24 Hz, —CH₂—), 3.23 (1H, d, J=13.60 Hz, CH₂), 3.49 (1H, d, J=23.12 Hz, CH₂), 3.64 (1H, d, J=23.12 Hz, CH₂), 5.06 (1H, s, CH—OH), 5.85 (1H, br s, CH—OH), 6.43 (1H, s, CH=C), 6.93 (1H, d, J=8.96 Hz, Ar—H), 6.97 (2H, d, J=8.04 Hz, Ar—H), 7.07 (1H, t, J=7.28 Hz, Ar—H), 7.17 (1H, t, J=7.40 Hz, Ar—H), 7.22-7.28 (4H, m, Ar—H), 7.39 (1H, t, J=3.44 Hz, Ar—H), 7.41 (1H, d, J=7.28 Hz, Ar—H), 7.72 (2H, d, J=8.20 Hz, Ar—H), 7.82 (1H, dd, J=2.60, 8.94 Hz, Ar—H), 8.24 (1H, d, J=2.48 Hz, Ar—H), 10.09 (1H, s, Ar—OH or O=C—OH).

¹³C NMR (100 MHz, DMSO-d₆): δ 38.47-40.58 (3×CH₂), 56.23 (quat C), 81.48 (CH—OH), 112.82, 117.46, 120.64, 122.15, 123.94, 124.27, 124.81, 124.91, 126.58, 126.82, 2×127.39, 127.68, 128.06, 129.00, 2×130.23, 131.35, 132.64 (16×tert. C and 3×quat. C), 140.76 (quat. C), 143.38 (quat. C), 143.53 (quat. C), 144.87 (quat. C), 145.52 (quat. C), 154.45 (quat. C), 157.77 (quat. C), 165.47 (N—C=O), 172.22 (O—C=O).

IL2 and Autoimmune Inflammatory Disease.

Cytokines can be produced by various cell populations and have been shown to augment or limit immune responses to pathogens and influence the autoimmune response. One family of cytokines, which uses the common receptor gamma chain (cc), a component of receptors for interleukin (IL)-2, IL-4, IL-7, IL-9, IL-15 and IL-21, has been classically defined as growth and survival factors.

IL-2 production can induce an immune response by promoting the proliferation and generation of CD4+ Th1, CD4+ Th2 and CD8+ CTL effector cells. Many of the immunosuppressive drugs used in the treatment of autoimmune diseases and organ transplant rejection, such as corticosteroids and immune suppressive drugs (ciclosporin, tacrolimus) work by inhibiting the production of IL-2 by antigen-activated T cells. Others (sirolimus) block IL-2R signalling, thereby preventing the clonal expansion and function of antigen-selected T cells [ref: Opposing functions of IL-2 and IL-7 in the regulation of immune responses Shoshana D. Katzman, Katrina K. Hoyer, Hans Dooms, Iris K. Gratz, Michael D. Rosenblum, Jonathan S. Paw, Sara H. Isakson, Abul K. Abbas. Cytokine 56 (2011) 116-121]

In contrast IL-2 can inhibit the immune response by promoting the survival and functionality of natural (thymic) regulatory T-cells (Tregs), promoting the generation of induced (peripheral) Tregs and inhibiting the generation of CD4+ Th17 effector cells [ref: IL-2 and autoimmune disease. Anneliese Schimpl, A., Berberich, I, Kneitz, B., Kramer, S., Santner-Nanan, B., Wagner, S., Wolf, M., Hünig, T. Cytokine & Growth Factor. Reviews 13 (2002) 369-378]. Interleukin-2/IL-2R deficiency with time leads to multiorgan inflammation and the formation of autoantibodies of various specificities. Depending on the genetic background, death occurs within a few weeks to a few months, mostly from autoimmune hemolytic anemia or inflammatory bowel disease (IBD) [ref. Sadlack B, Merz H, Schorle H, Schimpl A, Feller A C, Horak I. Ulcerative colitis-like disease in mice with a disrupted interleukin-2 gene. Cell 1993; 75:253-61].

IL-2 signalling has been shown to be important in both the initiation and regulation of immune responses. In these dual and opposing roles, IL-2 acts to balance immune response, both driving immune cell activation and subsequent reduction. The potential clinical applicability of either augmenting or inhibiting signals mediated by IL-2 is significant and includes cancer, autoimmune inflammatory diseases, organ transplantation and HIV.

Effect of Compounds on IL-2 Secretion in T Lymphocytes

1. Methodology

The T cell line Jurkat 6.1 (ATCC) was used. Cells were pre-treated for 30 min with 1 μM or 10 μM of the respective compound and then stimulated with plate-bound anti-CD3 (BD Pharmingen) and anti-CD28 (AnCell). DMSO was used as vehicle control. The immunosuppressive agent Cyclosporine A was used as a control for inhibition of IL-2 production. After 24 hs the supernatant was collected and IL-2 secretion was measured by ELISA.

2. Compound Preparation (Stock)

Compounds were prepared by dissolution in DMSO to yield final concentrations of 1 and 10 μg/ml 3. Results Absolute values for IL-2 production:

| Compounds | IL-2 pg/ml | Plate ID |
|---|---|---|
| Unstimulated 2 | −16.56 | 2 |
| DMSO Control 2 | 320.67 | 2 |
| Cyclos A 2 | 101.00 | 2 |
| Unstimulated 2 | −16.56 | 2 |
| 10 1 uM | 185.56 | 2 |
| 10 10 uM | 112.22 | 2 |
| 11 1 uM | 272.22 | 2 |
| 11 10 uM | 105.11 | 2 |
| 12 1 uM | 240.22 | 2 |
| 12 10 uM | 132.44 | 2 |
| 13 1 uM | 276.78 | 2 |
| 13 10 uM | 151.78 | 2 |
| 14 1 uM | 214.44 | 2 |
| 14 10 uM | 146.44 | 2 |
| 15 1 uM | 207.78 | 2 |
| 15 10 uM | 113.67 | 2 |
| 16 1 uM | 243.00 | 2 |
| 16 10 uM | 171.78 | 2 |
| 17 1 uM | 168.44 | 2 |
| 10 10 uM | 56.11 | 2 |
| 18 1 uM | 190.78 | 2 |
| 18 10 uM | 79.56 | 2 |
| 19 1 uM | 174.44 | 2 |
| 19 10 uM | 81.00 | 2 |
| 20 1 uM | 174.11 | 2 |
| 20 10 uM | 141.78 | 2 |
| 21 1 uM | 210.89 | 2 |
| 21 10 uM | 137.78 | 2 |
| 22 1 uM | 198.56 | 2 |
| 22 10 uM | 113.33 | 2 |
| 23 1 uM | 191.44 | 2 |
| 23 10 uM | 193.56 | 2 |
| 24 1 uM | 202.13 | 2 |
| 24 10 uM | 149.63 | 2 |
| 25 1 uM | 208.38 | 2 |
| 25 10 uM | 174.25 | 2 |
| 26 1 uM | 202.25 | 2 |
| 26 10 uM | 192.63 | 2 |
| 27 1 uM | 350.13 | 2 |
| 27 10 uM | 172.88 | 2 |
| 28 1 uM | 214.75 | 2 |
| 28 10 uM | 135.63 | 2 |
| 29 1 uM | 220.50 | 2 |
| 29 10 uM | 177.88 | 2 |
| 30 1 uM | 191.63 | 2 |
| 30 10 uM | 174.50 | 2 |
| 31 1 uM | 233.38 | 2 |
| 31 10 uM | 225.63 | 2 |
| 32 1 uM | 215.25 | 2 |
| 32 10 uM | 74.88 | 2 |
| 33 1 uM | 186.25 | 2 |
| 33 10 uM | 74.38 | 2 |
| 34 1 uM | 173.25 | 2 |
| 34 10 uM | 71.38 | 2 |
| 35 1 uM | 238.88 | 2 |
| 35 10 uM | 189.38 | 2 |
| 36 1 uM | 207.38 | 2 |
| 36 10 uM | 138.13 | 2 |
| 37 1 uM | 275.50 | 2 |
| 37 10 uM | 79.00 | 2 |
| 38 1 uM | 226.75 | 2 |
| 38 10 uM | 268.63 | 2 |
| Unstimulated 3 | 15.38 | 3 |
| DMSO Control 3 | 338.25 | 3 |
| Cyclos A 3 | 90.75 | 3 |
| Stauros 3 | 117.75 | 3 |
| 2 1 uM | 98.71 | 3 |
| 2 10 uM | 124.36 | 3 |
| 3 1 uM | 150.07 | 3 |
| 3 10 uM | 98.57 | 3 |
| 4 1 uM | 97.21 | 3 |
| 4 10 uM | 94.21 | 3 |
| 5 1 uM | 127.29 | 3 |
| 5 10 uM | 134.14 | 3 |
| 39 1 uM | 105.94 | 3 |
| 39 10 uM | 40.69 | 3 |
| 40 1 uM | 84.86 | 3 |
| 40 10 uM | 12.71 | 3 |
| 41 1 uM | 99.50 | 3 |
| 41 10 uM | 62.50 | 3 |
| 42 1 uM | 77.71 | 3 |
| 42 10 uM | 49.57 | 3 |
| 43 1 uM | 97.57 | 3 |
| 43 10 uM | 12.79 | 3 |
| 44 1 uM | 72.50 | 3 |

-continued

| Compounds | IL-2 pg/ml | Plate ID |
|---|---|---|
| 44 10 uM | 12.43 | 3 |
| 45 1 uM | 56.07 | 3 |
| 45 10 uM | 14.29 | 3 |
| 46 1 uM | 92.21 | 3 |
| 46 10 uM | 72.07 | 3 |
| 47 1 uM | 99.64 | 3 |
| 47 10 uM | 98.79 | 3 |

Results of Incubation of Compounds

The effect of synthetic compounds 2-5, 10-16, 18-38 and 39-47 on release of IL2 from Jurkat cells is demonstrated in FIGS. 21 and 22. Compounds were evaluated at 1 and 10 µm concentrations. Most compounds demonstrated an inhibition of release relative to the negative controls. However, compounds 40 (12.71 pg/ml), 43 (12.79 pg/ml), 44 (12.43 pg/ml), 45 (14.29 pg/ml) and 46 (72.07 pg/ml) (FIG. 22) were among the most potent significantly reducing Il2 release relative to the negative control (326.67 pg/ml) and approaching the efficacy of ciclosporin (101.00 pg/ml) at 1 µm. In addition compounds 10 (122.22 pg/ml), 32 (74.88 pg/ml), 33 (74.38 pg/ml) and 34 (71.38 pg/ml) (FIG. 21) were also potent significantly reducing IL-2 release relative to the negative control (320.67 pg/ml) Conversely compound 27 potentiates release of IL2 (350.13 pg/ml) at 1 µm greater than the negative control (338.25 pg/ml). IL-2 signalling has been shown to be important in both the initiation and regulation of immune responses. In these dual and opposing roles, IL-2 acts to balance immune response, both driving immune cell activation and subsequent reduction. The potential clinical applicability of either augmenting or inhibiting signals mediated by IL-2 is significant and includes cancer, autoimmune inflammatory diseases, organ transplantation and HIV.

Inflammatory Bowel Disease (IBD)

Inflammatory Bowel Disease (IBD) is an antiinflammatory immune disease which consists of two idiopathic inflammatory diseases, ulcerative colitis (UC) and Crohn's Disease (CD). The greatest distinction between CD and UC is the range of inflamed bowel tissue. Inflammation in CD is discontinuously segmented, known as regional enteritis, while UC is superficial inflammation extending proximally and continuously from the rectum. At present the cause of IBD is unknown. The disease seems to be related to an exaggerated mucosal immune response to infection of the intestinal epithelium because of an imbalance of pro-inflammatory and immune-regulatory molecules. The inheritance of patterns of IBD, suggest a complex genetic component of pathogenesis that may consist of several combined genetic mutations. Currently no specific diagnosis exists for IBD, but as an understanding of pathogenesis improves so will testing methods. Treatment of IBD consists of inducing and maintaining remission. IBD patients may be maintained on remission by use of a 5-aminosalycilate. However, while the use of aminosalycilates in UC provides considerable benefit, both in inducing remission in mild to moderate disease and in preventing relapse, the usefulness of these drugs to maintain remission in CD is questionable and is no longer recommended. The mainstay of treatment of active disease is a corticosteroid, commonly used for limited periods to return both UC and CD patients to remission, though budesonide, designed for topical administration with limited systemic absorption, has no benefit in maintaining remission. Alternatives, such as the immunosuppressive drugs azathioprine and mercaptopurine, together with methotrexate and cyclosporine have limited efficacy and the capability of inducing grave adverse effects. Anti-TNFα antibodies such as infliximab and adalimubab may be used in those patients unresponsive to standard immunosuppressive therapy. However, many patients fail to respond to anti-TNFα therapy, either due to their particular phenotype or by the production of autoantibodies.

Acute Murine DSS Colitis Model

The dextran sodium sulphate (DSS) colitis model is an experimental mouse model that exhibits many of the symptoms observed in human UC, such as diarrhoea, bloody faeces, mucosal ulceration, shortening of the colon, weight loss and alterations in certain colon cytokines. The study is widely used as a model for studying the pathogenesis of UC and also for screening new therapeutic interventions for the treatment of UC.

In these studies, an acute colitis model was used, with 5% DSS administered in the drinking water of BALB/c mice. This dosage regime induces severe acute colitis, by days 7-8 mice had overt rectal bleeding and marked weight loss; unless sacrificed beforehand, all mice would have died by days 10-12.

Experiment 1

Relating to Compounds 2-6

Mice

Specific Pathogen-Free BALB/c mice, 6-8 weeks of age, were obtained from a commercial supplier (Harlan UK). Mice were fed irradiated diet and housed in individually ventilated cages (Tecniplast UK) under positive pressure.

DSS Treatment

DSS (5%) was dissolved in drinking water. Compounds were administered orally at a dose of 10 mg/kg or 30 mg/kg on days 0-7, and mice were culled on day 8 or day 9, depending on the severity of the disease. The mice were checked each day for morbidity and the weight of individual mice was recorded. Induction of colitis was determined upon autopsy, length of colon and histology. Colons were recovered and stored at −20° C. for immunological analysis. All of the compounds and experimental groups are randomly alphabetically labelled. Throughout experiments all data recording was performed in a blind manner. The codes on boxes/groups were not broken until after the data was analysed i.e. boxes labelled A, B, C etc were identified as untreated, DSS-treated, or DSS+compound-treated.

To quantify the extent of colitis, a disease activity index (DAI) was determined based on weight loss, faecal blood and stool consistency. A score was given for each parameter, with the sum of the scores used as the DAI. For each treatment group n=8.

| | Description of DAI | | |
|---|---|---|---|
| Score | Weight loss % | Stool consistency | Faecal blood |
| 0 | None | Normal | None |
| 1 | 1-3 | | |
| 2 | 3-6 | Loose stool[1] | Visible in stool |
| 3 | 6-9 | | |
| 4 | >9 | Diarrhea[2] | Gross bleeding[3] |

Definitions:
[1]Loose stool—stool not formed, but becomes a paste on handling.
[2]Diarrhea—no stool formation, fur stained around the anus.
[3]Gross bleeding—fresh blood on fur around the anus with excessive blood in the stool.

Administration of Compounds

All compounds were prepared for oral gavage (0.1 mL per os (p.o.) per 10 g body weight) as a suspension in 0.5% carboxymethyl cellulose/2% Tween 80, at a dose of 3-30 mg/Kg. Compounds as free acid were initially dissolved in absolute alcohol and diluted with 14+1 with 0.5% carboxymethyl, cellulose/2% Tween 80; this resulted in a fine precipitate in suspension while N-Methyl-(D)-Glucamine salts were soluble in the vehicle alone.

Figure 3:
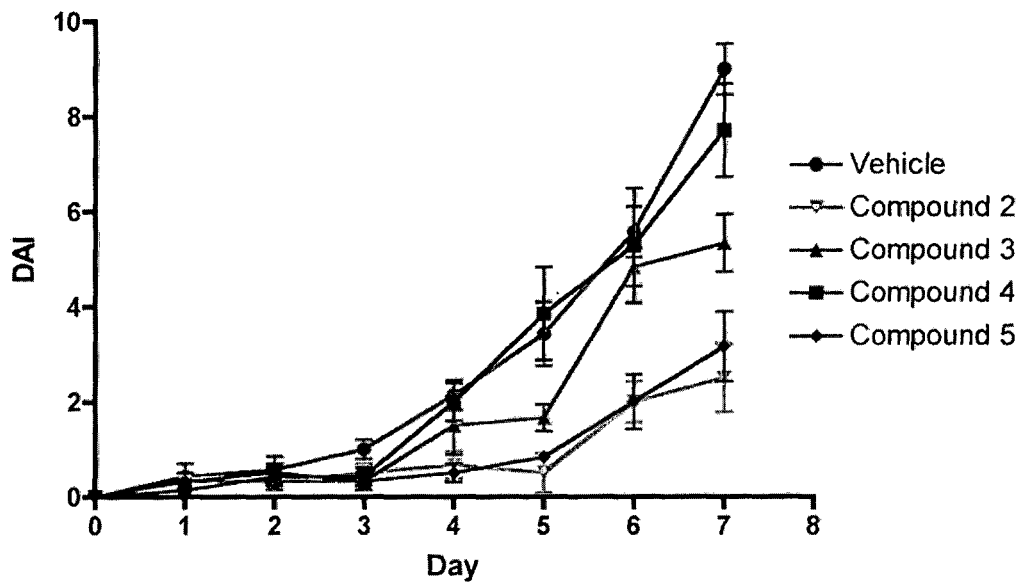
FIG. 3: Is a graph of the effect of compounds 2, 3, 4 and 5 at 30 mg/kg on disease activity index (DAI) over 7 days in 5% DSS colitis.
Figure 4:
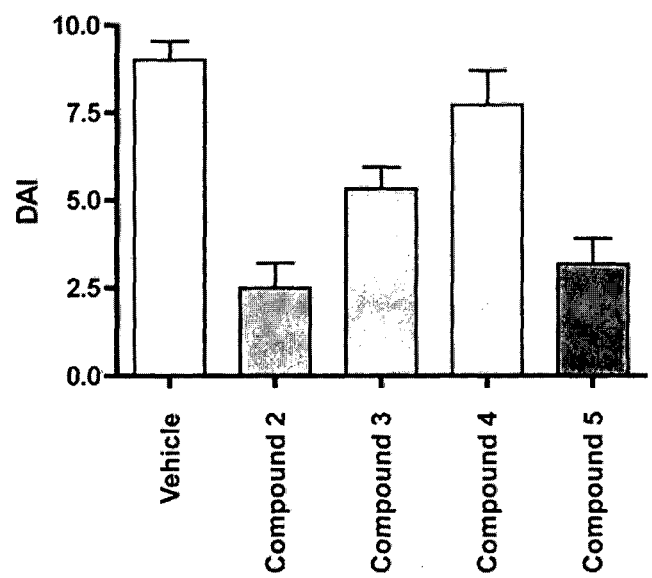
FIG. 4: Is a bar chart of the effect of compounds 2, 3, 4 and 5 at 30 mg/kg on disease activity index (DAI) at day 7 in 5% DSS colitis.

Effect of Individual Enantiomers Compounds 2, 3, 4 and 5 in 5% DSS Murine Colitis BALB/c given 5% DSS in drinking water were administered compounds 2, 3, 4 and 5 at 30 mg/kg p.o. as a suspension in 0.5% carboxymethyl cellulose/2% Tween 80 daily for 7 days. DAI measures the extent of the disease in this model. Compound 4 was without activity on this variable, there not being any significant (P>0.05) difference in DAI at any timepoint (FIG. 3). At day 7, both compound 2 and compound 5 significantly (P<0.5) reduced DAI by a considerable margin, from 9.0±0.53 for vehicle controls to 3.2±0.73 for compound 5 and 2.5±0.71 for compound 2, there being no significant difference between the two (FIG. 4). In comparison, compound 3 reduced DAI to only 5.3±0.6. This was significantly (P>0.05) less potent than either compound 2 or compound 5. Further, while the DAI in compound 3-treated mice was statistically (P<0.05) less than vehicle controls at day 7 (FIG. 4), at day 6 there was no statistical (P>0.05) difference between compound 3 and vehicle (FIG. 3). In conclusion, of the four enantiomers, compounds 2, 3, 4 and 5, both compounds 2 and 5 are highly active in this model at 30 mg/kg. Compound 3 has minimal activity which is significantly (P<0.05) less than compound 2 and compound 5. Compound 4 is almost devoid of activity in this 5% DSS murine colitis model.

Selection of a Salt of Compounds 2 and 5

As a consequence of the limited aqueous solubility of the enantiomers compound 2 and compound 5, we attempted the synthesis of five salts of compound 5. The sodium salt, potassium salt, calcium salt, α-methylbenzylamine salt and N-Methyl-(D)-Glucamine salt were synthesised. The sodium and calcium salt were unsuccessful. The three salts of compound 5, named potassium salt, α-methylbenzylamine salt and N-Methyl-(D)-Glucamine salt were used for solubility and partition coefficient (log P) studies.

The solubility of the four compounds were determined:

| Compound | Milli-RO H$_2$0 µg/mL | pH 4.0 Buffer µg/mL | pH 7.0 Buffer µg/mL | pH 9.0 Buffer µg/mL |
| --- | --- | --- | --- | --- |
| Compound 5 | 1.38 | 0.33 | 320.1 | 369.6 |
| Compound 5 Potassium salt | 217.0 | 0.15 | 54.71 | 340.3 |
| Compound 5 Methyl-benzylamine salt | 413.9 | 0.20 | 227.4 | 311.0 |
| Compound 5 N-Methyl-D-Glucamine salt | >60,000* | 0.14 | >60,000* | >60,000* |

*Estimated value

Compound 5 N-Methyl-(D)-Glucamine salt (compound 7) was determined, surprisingly, to be the most soluble compound from this group of analogous compounds by a considerable margin, with a solubility of >60,000 µg/mL in Milli-RO water, 0.14 µg/mL in pH 4 buffer, >60,000 µg/mL in pH 7.0 and >3,000 µg/mL in pH 9.0 buffer. Almost identical values were obtained with compound 2 N-Methyl-(D)-Glucamine (compound 6) with a solubility of >60,000 µg/mL in Milli-RO water, 0.5 µg/mL in pH4 buffer, >60,000 mg/mL in pH 7.0 and >3,000 µg/mL in pH 9.0 and buffer.

The partition coefficient of compound 5 and related analogous compounds was investigated using the HPLC method (reverse phase C18 HPLC column) at neutral, acidic and alkaline pH.

The partition coefficient of the four compounds were determined:

| Compound | Neutral Log10 POW | Basic Log10 POW | Acid Log10 POW |
| --- | --- | --- | --- |
| Compound 5 | 3.7 | 3.7 | 3.9 |
| Compound 5 Potassium salt | 3.7 | 3.7 | 3.9 |
| Compound 5 Methyl-benzylamine salt | 3.6 | 3.6 | 3.9 |
| Compound 5 N-Methyl-D-Glucamine salt | 3.5 | 3.5 | 3.8 |

The partition coefficient of each salt of compound 5 was found to be similar. It is suggested that this is happening because when the salt is in solution the compound dissociates into the parent compound 5 and the associated salt ion. As a result of this the measured partition coefficient was from the parent ion rather than the salt molecules.

The partition coefficient (Log 10 POW) of compound 2 N-Methyl-D-Glucamine salt (compound 6) was successfully determined in neutral, basic and acidic conditions as 3.5, 4.3 and 2.6 respectively.

N-Methyl-(D)-Glucarnine was chosen as the salt candidate for both compound 2 and compound 5.

Figure 5:
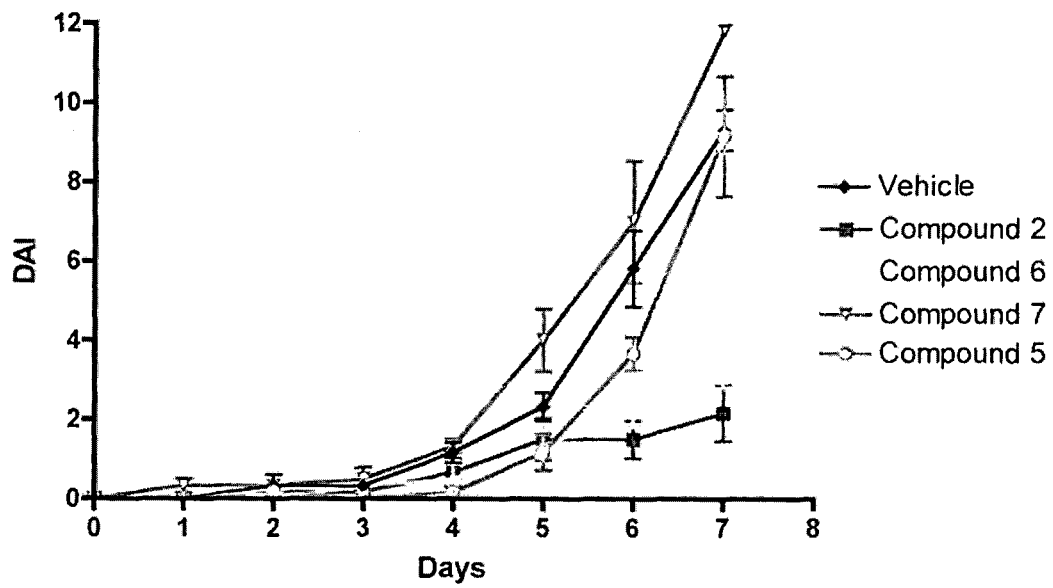
FIG. 5: Is a graph of the effect of compounds 5, 7, 2 and 6 at 10 mg/kg on disease activity index (DAI) over 7 days in 5% DSS colitis.
Figure 6:
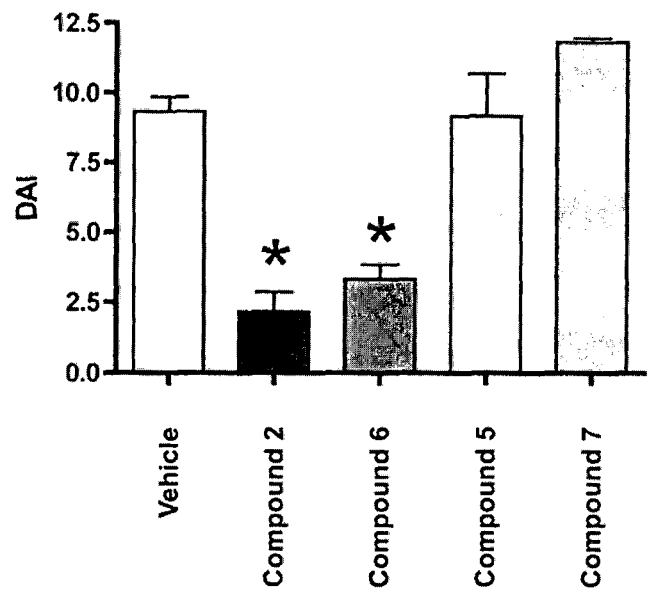
FIG. 6: Is a bar chart of the effect of compounds 5, 7, 2 and 6 at 10 mg/kg on disease activity index (DAI) at day 7 in 5% DSS colitis. Asterisks indicate a significant (P<0.05) difference (1 way ANOVA) from the vehicle control group.

Effect of Enantiomers Compound 2 and Compound 5 and their N-Methyl-(D)-Glucamine Salts (Compounds 6 and 7) at 10 Mg/Kg in 5% DSS Murine Colitis Given that both compounds 2 and 5 show considerable activity in the 5% DSS model at 30 mg/kg, we then re-examined their activity, together with their N-Methyl-(D)-Glucamine salts at the lower dose of 10 mg/kg, given daily for 7 days as a suspension or solution in 0.5% carboxymethyl cellulose/2% Tween 80. No adjustment was made in the dosages of the salts to compensate for their increased molecular weight. Both compounds 5 and 7, at 10 mg/kg, had no significant (P>0.05) effect on DAI in the 5% DSS murine colitis model when compared to vehicle control (see FIG. 5). In contrast, at day 7, both compound 2 and compound. 6, the N-Methyl-(D)-Glucamine salt, at 10 mg/kg significantly (P<0.05) and potently reduced DAI from 9.3±0.51 (vehicle) to 2.1±0.7 and 3.3±0.52 respectively (FIG. 6).

In conclusion, compound 2 (and its N-Methyl-(D)-Glucamine salt, compound 6) is the most potent of the four enantiomers by a considerable margin, and the only enantiomer to retain activity at the lower dose level of 10 mg/kg.

Effect of a Range of Doses of Compound 6 and a Comparison with Prednisolone on 5% DSS Murine Colitis Compound 6 was selected as the most favoured enantiomer. The activity of compound 6 in the 5% DSS murine model of colitis at varying dose levels was tested to a certain if there was a dose/response relationship and to make a comparison with a potent oral steroid, Prednisolone, commonly used to return patients suffering from acute exacerbations of IBD to remission.

Figure 7:
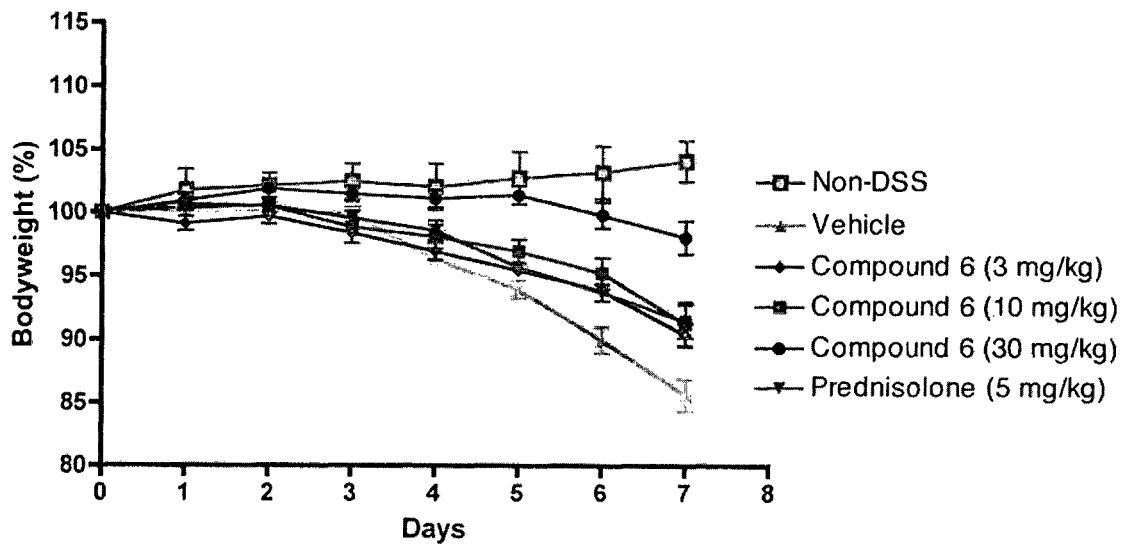
FIG. 7: Is a graph showing the effect of compound 6 on weight loss in 5% DSS-treated mice. Data are Mean±SEM from 6-7 mice per group.
Figure 8:
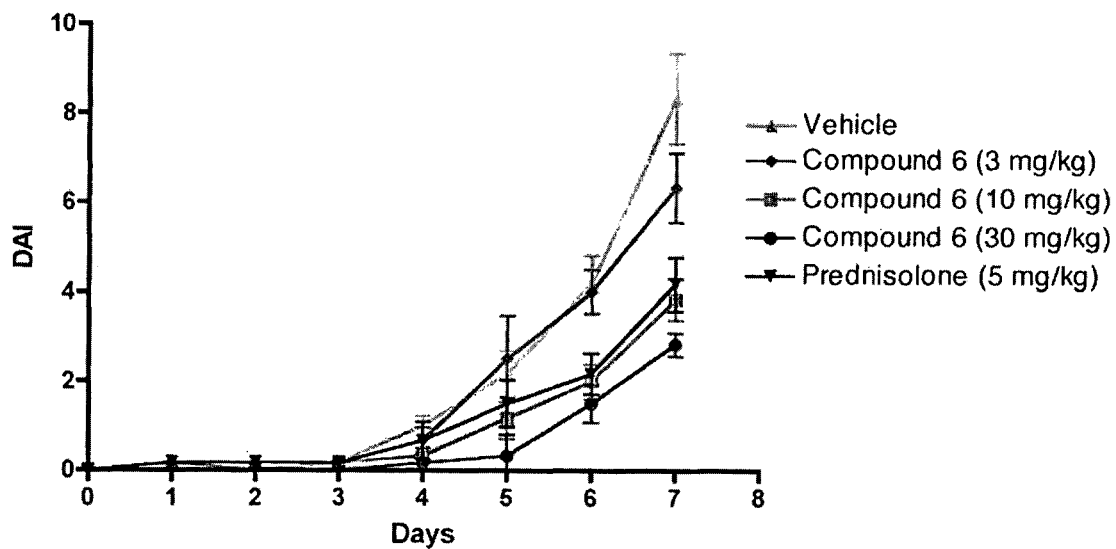
FIG. 8: Is a graph showing the effect of compound 6 on DAI in 5% DSS-treated mice. Data are Mean±SEM from 6-7 mice per group.

Mice were administered compound 6 at dose levels 3, 10 and 30 mg/Kg (equivalent to 6.6-20 mg/Kg of the compound 2). A group of DSS-treated mice was also treated with prednisolone, 5 mg/Kg. Prednisolone is a corticosteroid in clinical use in the treatment of human IBD and the quantity used in this study is the optimal dose of prednisolone for this model. After 3 days of treatment of BALB/c mice with 5% DSS in the drinking water signs of colitis were apparent. This was manifested as weight loss (FIG. 7) and an increase in the disease DAI (FIG. 8). However, following oral administration daily for 7 days, compound 6 at three doses (3, 10 and 30 mg/Kg) caused no overt reactions in mice. Compound 6 ameliorated the severity of colitis following acute DSS treatment in multiple parameters of disease examined. The capacity of compound 6 to ameliorate disease in the DSS model was dose-dependent. Compound 6 at 30 mg/Kg was therapeutic in the DSS model at a comparable, or better, efficacy relative to prednisolone at 5 mg/Kg.

Figure 9:
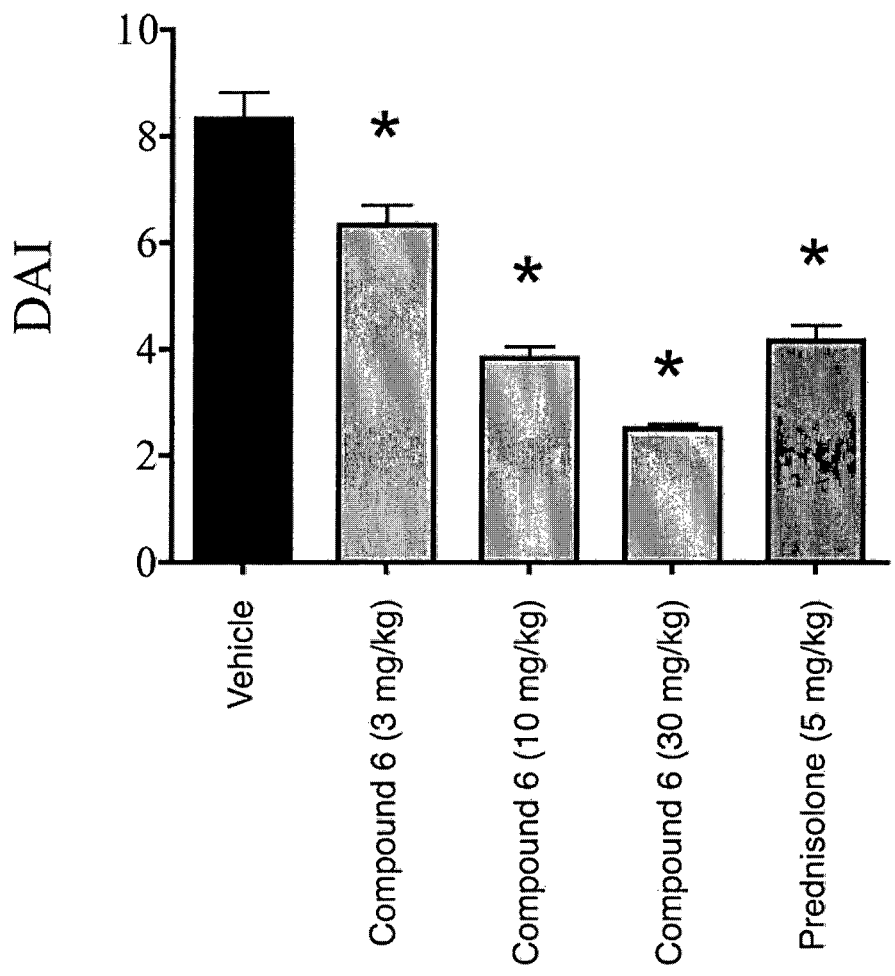
FIG. 9: Is a bar chart showing the effect of compound 6 on. DAI in 5% DSS-treated mice on day 7. Data are Mean±SEM.

The severity of these symptoms are progressive; by day 7 the DSS-treated mice have lost up to 15% of their body weight and all mice have perfuse rectal bleeding. The DAI values on the day of autopsy showed that mice treated with compound 6 3-30 mg/kg had at each dose level, a significantly (P<0.05-P<0.01) lower DAI than vehicle controls. Prednisolone (5 mg/kg) also significantly (P<0.01; ANOVA; Dunnett Multiple Comparison Test) reduced DAI scores (FIG. 9).

At autopsy on day 7, there was significant shortening of colon length (P<0.05-P<0.01; ANOVA; Dunnett Multiple Comparison Test) in all DSS treated groups compared to colons from mice not treated with DSS (FIG. 10). The lowest dose of 3 mg/kg of compound 6 did not have a significant effect in inhibiting colon shortening when compared to vehicle controls whereas the 10 and 30 mg/kg groups and the Prednisolone group did have a significant effect. Compound 6 at 30 mg/kg was significantly better than Prednisolone (P<0.05; ANOVA; Dunnett Multiple Comparison Test) (FIG. 10).

Histology sections of the distal colon showed extensive crypt damage and cell infiltration following DSS treatment (FIG. 11).

The extent of colon damage was quantified using an arbitrary scoring system. Compound 6 at both 10 and 30 mg/Kg, caused a dose-dependent and highly statistically significant reduction (P<0.01; Kruksal-Wallis ANOVA; Dunnett Multiple Comparison Test) in colon pathology relative to the vehicle group. In contrast, there was no significant improvement in histology scores with the prednisolone (5 mg/Kg) treated group relative to vehicle-treated mice (FIG. 12).

Consistent with the histology results showing inflammation in the colons of mice, there was a significant (P<0.001; Kruksal-Wallis ANOVA; Dunnett Multiple Comparison Test) elevation in colon myeloperoxidase (MPO) activity in DSS-treated mice administered vehicle only. Colonic myeloperoxidase activity (MPO), representing the level of inflammatory neutrophil cell infiltration into the gut wall which was increased by almost 8-fold by DSS treatment but was significantly (P<0.05) reduced by both compound 6 at 30 mg/kg and Prednisolone, at 63% and 54% respectively by day 7 (FIG. 13).

Quantification of levels of colon cytokines showed that DSS-treatment induces elevated IL1β (FIG. 14(a)), TNFα (FIG. 14(b)) and IL6 (FIG. 14(c))., to 0.744±0.076 ng/mg, 1.478±0.378 ng/mg and 1.057±0.1784 ng/mg respectively. In each case, compound 6 caused a significant (P<0.05, 30 mg/kg) and dose-dependant reduction in these cytokine levels. Prednisolone (5 mg/kg) also reduced (p<0.05) these increases in cytokine levels; for each cytokine there was no significant difference between the effect of prednisolone 5 mg/kg and compound 6 at the higher dose level of 30 mg/kg at day 7

To summarise, following oral administration daily for 7 days, compound 6 at three doses (3, 10 and 30 mg/Kg) caused no overt reactions in mice. Compound 6 ameliorated the severity of colitis following acute 5% DSS treatment by multiple parameters of disease examined and the capacity to ameliorate the disease is dose-dependent. Further, compound 6 at 30 mg/Kg was therapeutic in the DSS model at a comparable or better efficacy, relative to prednisolone (5 mg/Kg).

Chronic IL10$^{--/--}$ Model

Mice with a deletion in the IL10$^{--/--}$ gene spontaneously develop chronic colitis, with the age of onset and the severity of the disease being dependent on background mouse strain and the conditions in which the animals are housed. The onset of colitis in IL10$^{--/--}$ mice housed under the conditions used in this study was also strain dependent, with an earlier onset and greater severity, in terms of mortality, in BALB/c strain mice relative to C57BL/6 strain animals. In this experiment, animals received oral treatment on a MWF regime over 9 weeks. Initially, both groups of mice progressively gain weight (FIG. 15). Vehicle treated mice stopped gaining weight from week 5 of treatment, whereas compound 6-treated mice maintained weight gain until week 8. By week 9 animals had marked weight loss, with one moribund animal humanely killed on day 60 in each group. As other mice were losing weight and developing clinical symptoms of disease, both groups were culled at week 9 (day 63) and analysed. While there were greater mortalities in the vehicle-treated group (25%) relative to compound 6 treated mice (9.2%) by Kaplan-Meier analysis, there was no statistical difference in survival of IL10$^{--/--}$ mice over the 9 weeks.

Serum was recovered from mice and Serum Amyloid A (SAA) analysed as a marker for severity of colitis. There were significantly (P<0.05; Student's t-test) reduced SAA levels in compound 6 treated mice relative to vehicle treated IL10$^{--/--}$ mice (FIG. 16).

Histology sections of colons from IL10$^{--/--}$ mice treated with vehicle or compound 6 are shown in FIG. 17.

Histology sections of colons from IL10$^{--/--}$ mice treated with vehicle or compound 6 were scored. The extent of colon pathology was significantly reduced (P<0.05; Student's t-test) in IL10$^{--/--}$ mice receiving compound relative to mice treated with vehicle (FIG. 18).

To summarise, oral treatment with compound 6 (300 mg/kg/week) in IL10$^{--/--}$ BALB/c strain mice, using a MWF regime over 9 weeks, delayed weight loss and reduced deaths from colitis relative to vehicle-treated mice. In this model of chronic colitis, compound 6 significantly reduced disease indices with respect to a serum marker of colon inflammation and the degree of inflammation and damage to the colon. This is particularly noteworthy in view of the fact that the plasma half-life ($t_{1/2}$) for compound 6 is 3 hours in the rat. With the standard MWF dosing schedule, mice will have been unexposed to compound 6 for substantial periods during the experiment.

Experiment 2

Relating to Compounds 31 and 47

1. Procedures
2.1 Animals and caging

A total of 90 BDF1 (*H. pylori*-free, murine norovirus-free) male mice (Harlan Laboratories, UK) were used in the study. Animals were 8-10 weeks old on supply and used at 10-12 weeks of age. All mice were held in individually ventilated cages (IVCs) in an SPF (Specific Pathogen Free) barrier unit. The animals were identified by numbered cages and by ear punches.

2.2 Diet and Animal Welfare

The animals were fed Rat and Mouse Expanded diet from B & K. Both feed and water (from drinking bottles) were available ad libitum. There was a constant room temperature of 21±2° C. and a mean relative humidity of 55±10%. The day-night cycle was constant, with light and dark phases of 12 hours each. Animal health was monitored daily and cages were cleaned at regular intervals.

2.3 Groups, Dosages, Administration and Formulations

Mice were randomised into study groups. All the mice in any one cage received the same treatment and were ear punched for identification purposes. Daily body weight measurements were used to calculate the volume of test item or vehicle administered in the applicable groups.

2.4 Preparation and Administration of DSS and Test Items

DSS

DSS (MP Biomedicals 0216011090, lot# M2709) was prepared as a 5% (w/v) solution in the drinking water and made fresh daily on days 0 to 6 inclusive. DSS was administered from day 0 to day 7.

Compounds 31 and 47

Test items were stored at −20° C. until the initiation of the study. Each test item was formulated as a homogenous suspension in 0.5% carboxymethyl cellulose (CMC, Sigma C4888) in sterile water (Sigma W3500, lot# RNBC1419), using an Ultraturax homogeniser, on study day −1. Compound 31 was formulated at 2 mg/ml and 47 was formulated at 4 mg/ml. After formulation the test item and the vehicle stocks anonymised with a letter code. All solutions were stored at 4° C. during the study, with 3.8 ml of each suspension being dispensed daily. Test items were administered by oral gavage, daily at 09.00 hrs, at 10 ml/kg, from study day 0 to study day 6.

5-ASA

5-ASA (5-Aminosalicylic acid, Sigma A3537, lot#051M1878V) was aliquoted into preweighed amounts between 71 and 84 mg. Like test item suspensions, these aliquots were anonymised by a letter code. Individual aliquots were formulated as a 10 mg/ml suspension in 0.5% CMC (Sigma C4888) in sterile water (Sigma W3500, lot# RNBC1419) on each day of dosing. 5-ASA was administered by oral gavage, daily at 09.00 hrs, at 10 ml/kg to give a dose of 100 mg/kg, from study day 0 to study day 6. 2.5 Clinical examinations Any animal demonstrating more than 15% weight loss was considered unwell and treatment may have been withheld. Any animal was culled if the weight loss was greater than 20%. Animal well-being was monitored daily. Once daily from day 0 until the end of the study, all mice were weighed and assessed for stool consistency, and the presence of overt blood in the stool or around the anus according to the criteria in 2.1

TABLE 0.1

Scoring criteria for in-life disease parameters.

| Score | Weight Loss (% day 0 weight) | Stool consistency | Overt blood (in stool/around anus) |
|---|---|---|---|
| 0 | <1% | Normal | None |
| 1 | ≥1% <5% | Slight diarrhoea | Slight |
| 2 | ≥5% <10% | Moderate diarrhoea | Moderate |
| 3 | ≥10% <15% | Heavy diarrhoea | Severe |
| 4 | ≥15% | | |

At necropsy, observation of stool in the large bowel was used to supplement in-life observation. If the large bowel was empty and no in-life observation was made, then a default score of 1 was given for stool consistency. In addition to the standard observations detailed above, mice were housed individually for a period of up to 30 minutes, in order to enhance the probability of make a stool observation; this was only performed for mice in the main study groups. Faecal occult blood tests were also performed on observed stools for the main study group, using Hemoccult cards (Becton Coulter), according to the manufacturer's instructions.

Effect of Single Doses of Compounds 47 and 31 and in Murine DSS (Model 2) at Day 7.

Initial results show, that in comparison with vehicle control, compound 47 does not result in an increase in loss of body weight in the DSS murine colitis model and is comparable with 5ASA (FIG. 19). In addition both compound 47 and compound 31 reduced DAI comparable or equal to 5ASA in comparison with vehicle (FIG. 20). This shows that these compounds have comparable activity to 5ASA on these parameters of the disease model and may have use in treatment of IBD.

FIG. 21 is a bar chart illustrating the effect of compounds on IL2 release from Jurkat cells.

FIG. 22 is a bar chart illustrating the effect of compounds on IL2 release from Jurkat cells.

The invention is not limited to the embodiments hereinbefore described which may be varied in detail.

APPENDIX 1

List of Chemical Abbreviations Used aq aqueous
b.p. boiling point
$CDCl_3$ chloroform-d
$CH(OCH_3)_3$ trimethylsilyl orthoformate
$CO_2$ carbon dioxide
DCM dichloromethane
dIW distilled ionized water
DMSO dimethyl sulphoxide
$Et_2O$ ether
EtOH ethanol
$H_2O$ water
HCl hydrochloric acid
IR infra red
IPA isopropyl alcohol
KCl potassium chloride
M molar
min minutes
μl microliters
mM milli-molar
m.p. melting point
$N_2$ nitrogen
$NaBH_4$ sodium borohydride
NaOH sodium hydroxide
$Na_2SO_4$ sodium sulphate
NMR nuclear magnetic resonance
oxygen
RT room temperature
$^tBuOH$ tert butanol
$^tBuOK$ potassium tert butoxide
S.E.M. standard error of mean
THF tetrahydrofuran
TLC thin layer chromatography
μl microliters
Triflic Acid trifluoromethanesulfonic acid
TMS Triflate trimethyl silyl trifluoromethanesulfonate
v/v volume per volume
w/v weight per volume
$\lambda_{em}$ emission wavelength
$\lambda_{exc}$ excitation wavelength

List of Biological Abbreviations Used

5-ASA 5-aminosalicylic acid
DAI Disease Activity Index
DSS Dextran Sulphate Sodium
IBD Inflammatory Bowel Disease
IVC Individually ventilated cages
MPO Myeloperoxidase
PBS Phosphate buffered saline
PEG Polyethylene glycol
p.o. per-os
p.r. per-rectum
q.d. quaque-die
SD Standard deviation
SPF Specific pathogen free
v/v Volume/volume
w/v Weight/volume

APPENDIX 2

X-Ray Studies

A single crystal X-ray analysis was carried out on compound 2 (S)-(−)-methylbenzylamine salt (compound 8), using a SuperNova, Dual, Cu at zero, Atlas Diffractometer and the parameters outlined in Table 1.

TABLE 1

Data collection and structure refinement for compound 8, the (S)-(−)-methylbenzylamine salt of compound 2.

| | |
|---|---|
| Diffractometer | SuperNova, Dual, Cu at zero, Atlas |
| Radiation source | SuperNova (Cu) X-ray Source, Cu Kα |
| Data collection method | Omega scans |
| Theta range for data collection | 3.74 to 76.22° |
| Index ranges | $-13 \leq h \leq 13, -11 \leq k \leq 12,$ $-14 \leq l \leq 14$ |
| Reflections collected | 12753 |
| Independent reflections | 5263 [R(int) = 0.0196] |
| Coverage of independent reflections | 99.4% |
| Variation in check reflections | N/A |
| Absorption correction | Semi-empirical from equivalents |
| Max. and min. transmission | 1.00000 and 0.90238 |
| Structure solution technique | direct |
| Structure solution program | Bruker SHELXTL |
| Refinement technique | Full-matrix least-squares on $F^2$ |
| Refinement program | Bruker SHELXTL |
| Function minimized | $\Sigma w(F_o^2 - F_c^2)^2$ |
| Data/restraints/parameters | 5263/1/363 |
| Goodness-of-fit on $F^2$ | 1.007 |
| $\Delta/\sigma_{max}$ | 0.001 |
| Final R indices | |
| 5161 data; I > 2σ(I) | R1 = 0.0321, wR2 = 0.0857 |
| all data | R1 = 0.0327, wR2 = 0.0865 |
| Weighting scheme | $w = 1/[\sigma^2 (F_o^2) + (0.0600P)^2 + 0.2200P]$ where $P = (F_o^2 + 2F_c^2)/3$ |
| Absolute structure parameter | 0.04(14) |
| Extinction coefficient | 0.0035(5) |
| Largest diff. peak and hole | 0.214 and −0.154 eÅ$^{-3}$ |

Refinement Summary:

| | |
|---|---|
| Ordered Non-H atoms, XYZ | Freely refining |
| Ordered Non-H atoms, U | Anisotropic |
| H atoms (on carbon), XYZ | Idealized positions riding on attached atoms |
| H atoms (on carbon), U | Appropriate multiple of U(eq) for bonded atom |
| H atoms (on heteroatoms), XYZ | Freely refining |
| H atoms (on heteroatoms), U | Isotropic |
| Disordered atoms, OCC | Refined with a two part model constrained to a total of unity |
| Disordered atoms, XYZ | freely refining |
| Disordered atoms, U | freely refining |

The single crystal X-ray data establishes that the structure of compound 8 is monoclinic, space group $P2_1$, with one molecule of compound 8 in the asymmetric unit (Table 2).

TABLE 2

Sample and crystal data for compound 8

| | |
|---|---|
| Crystallization solvents | Diethyl ether, MeOH, THF |
| Crystallization method | Slow evaporation |
| Empirical formula | $C_{34}H_{33}N_1O_3$ |
| Formula weight | 503.61 |
| Temperature | 100(1) K |
| Wavelength | 1.54178 Å |
| Crystal size | 0.50 × 0.50 × 0.50 mm |
| Crystal habit | Colourless Block |
| Crystal system | Monoclinic |
| Space group | $P2_1$ |
| Unit cell dimensions | a = 11.0344(2) Å    α = 90° |
| | b = 10.1727(2) Å    β = 93.682(2)° |
| | c = 11.8532(2) Å    γ = 90° |
| Volume | 1327.77(4) Å$^3$ |
| Z | 2 |
| Density (calculated) | 1.260 Mg/m$^3$ |
| Absorption coefficient | 0.627 mm$^{-1}$ |
| F(000) | 536 |

The absolute stereochemistry was determined as S, S at C9 and C10 for compound 2 and S at C33 for the methylbenzylamine cation. The assignment was made from consideration of both the Flack parameter which was determined to be 0.04 (14) and from the a priori knowledge of the stereochemistry of the salt former.

The absolute stereochemistry was also determined using Bayesian statistics on the Bijvoet pair differences which resulted in a probability of the stereochemistry at the chiral centres C9, C1.0 and C33 being S, S and S respectively as 1.000 and R, R and R as 0.000. This supports the assignment of S, S and S for C9, C10 and C33 respectively from the Flack parameter measurement.

The calculated X-ray powder diffraction pattern from the single crystal X-ray structure was in agreement with the stereochemistry shown in FIG. 2 (or the following).

TABLE 3

Atomic coordinates and equivalent isotropic, atomic displacement parameters, (Å$^2$), for compound 8. U(eq) is defined as one third of the trace of the orthogonalised $U_{ij}$ tensor.

| | x/a | y/b | z/c | U(eq) |
|---|---|---|---|---|
| O1 | 0.02763(10) | 0.17316(11) | 1.16556(8) | 0.0228(2) |
| O2 | 0.07430(9) | −0.03465(10) | 1.12294(7) | 0.0194(2) |
| O3 | 0.10561(8) | 0.01057(10) | 1.90142(8) | 0.0184(2) |
| C1 | 0.08315(12) | −0.12167(14) | 1.47373(12) | 0.0198(3) |
| C2 | 0.07248(13) | −0.09752(14) | 1.35802(12) | 0.0192(3) |
| C3 | 0.08014(11) | 0.02912(13) | 1.31666(11) | 0.0158(3) |
| C4 | 0.05975(11) | 0.05851(14) | 1.19195(11) | 0.0164(3) |
| C5 | 0.10196(12) | 0.13219(14) | 1.39262(11) | 0.0184(3) |
| C6 | 0.11261(13) | 0.10790(14) | 1.50817(11) | 0.0197(3) |
| C7 | 0.10101(11) | −0.01884(14) | 1.55106(10) | 0.0164(3) |
| C8 | 0.09988(12) | −0.04205(14) | 1.67717(10) | 0.0177(3) |

TABLE 3-continued

Atomic coordinates and equivalent isotropic, atomic displacement parameters, (Å$^2$), for compound 8. U(eq) is defined as one third of the trace of the orthogonalised $U_{ij}$ tensor.

| | x/a | y/b | z/c | U(eq) |
|---|---|---|---|---|
| C9 | 0.22568(11) | −0.05199(14) | 1.74191(10) | 0.0160(3) |
| C10 | 0.20981(12) | −0.06390(14) | 1.87231(10) | 0.0173(3) |
| C11 | 0.32285(12) | −0.00001(14) | 1.92450(11) | 0.0183(3) |
| C12 | 0.36695(13) | −0.00323(15) | 2.03747(11) | 0.0217(3) |
| C13 | 0.46523(13) | 0.07703(16) | 2.07062(12) | 0.0263(3) |
| C14 | 0.51796(13) | 0.15733(16) | 1.99312(13) | 0.0271(3) |
| C15 | 0.47368(13) | 0.16061(15) | 1.87974(13) | 0.0237(3) |
| C16 | 0.37476(12) | 0.08173(14) | 1.84684(11) | 0.0188(3) |
| C17 | 0.30303(12) | 0.07486(14) | 1.73362(11) | 0.0189(3) |
| C18 | 0.29536(12) | −0.17122(14) | 1.70380(10) | 0.0170(3) |
| C19 | 0.24493(13) | −0.29849(15) | 1.68674(11) | 0.0224(3) |
| C20 | 0.34284(13) | −0.38466(15) | 1.64945(10) | 0.0202(3) |
| C21 | 0.34340(15) | −0.51740(16) | 1.62093(12) | 0.0279(3) |
| C22 | 0.45250(18) | −0.57426(17) | 1.59308(13) | 0.0363(8) |
| C23 | 0.55837(16) | −0.50075(18) | 1.59165(13) | 0.0317(4) |
| C24 | 0.55735(14) | −0.36697(17) | 1.61785(12) | 0.0269(3) |
| C25 | 0.44911(13) | −0.31016(15) | 1.64729(11) | 0.0212(3) |
| C26 | 0.42215(14) | −0.17370(16) | 1.68241(12) | 0.0238(3) |
| C18A | 0.29536(12) | −0.17122(14) | 1.70380(10) | 0.0170(3) |
| C19A | 0.24493(13) | −0.29849(15) | 1.68674(11) | 0.0224(3) |
| C20A | 0.34284(13) | −0.38466(15) | 1.64945(10) | 0.0202(3) |
| C21A | 0.34340(15) | −0.51740(16) | 1.62093(12) | 0.0279(3) |
| C22A | 0.45250(18) | −0.57426(17) | 1.59308(13) | 0.0279(3) |
| C23A | 0.55837(16) | −0.50075(18) | 1.59165(13) | 0.0317(4) |
| C24A | 0.55735(14) | −0.36697(17) | 1.61785(12) | 0.0269(3) |
| C25A | 0.44911(13) | −0.31016(15) | 1.64729(11) | 0.0212(3) |
| C26A | 0.42215(14) | −0.17370(16) | 1.68241(12) | 0.0238(3) |
| N1 | −0.09024(11) | −0.21952(13) | 1.02800(10) | 0.0194(2) |
| C27 | −0.18541(12) | 0.06679(15) | 0.92258(12) | 0.0220(3) |
| C28 | −0.19466(13) | 0.15069(16) | 0.82981(13) | 0.0256(3) |
| C29 | −0.23606(14) | 0.10317(17) | 0.72421(13) | 0.0273(3) |
| C30 | −0.26855(15) | −0.02757(18) | 0.71195(13) | 0.0301(3) |
| C31 | −0.26063(14) | −0.11089(16) | 0.80481(13) | 0.0255(3) |
| C32 | −0.21928(12) | −0.06417(15) | 0.91135(11) | 0.0200(3) |
| C33 | −0.21444(12) | −0.15827(15) | 1.01084(12) | 0.0205(3) |
| C34 | −0.24587(14) | −0.09613(16) | 1.12172(13) | 0.0256(3) |

TABLE 4

Selected bond lengths, (Å), for compound 8

| O1-C4 | 1.2528(18) | O2-C4 | 1.2688(17) |
|---|---|---|---|
| O3-C10 | 1.4373(16) | O3-H3A | 0.88(2) |
| C1-C2 | 1.3909(19) | C1-C7 | 1.3964(19) |
| C2-C3 | 1.383(2) | C3-05 | 1.3929(19) |
| C3-C4 | 1.5108(17) | C5-C6 | 1.3893(18) |
| C6-C7 | 1.395(2) | C7-C8 | 1.5141(16) |
| C8-C9 | 1.5457(17) | C9-C18 | 1.5203(19) |
| C9-C17 | 1.5537(19) | C9-C10 | 1.5713(16) |
| C10-C11 | 1.5040(18) | C11-C16 | 1.391(2) |
| C11-C12 | 1.3953(17) | C12-C13 | 1.394(2) |
| C13-C14 | 1.385(2) | C14-C15 | 1.401(2) |
| C15-C16 | 1.390(2) | C16-C17 | 1.5152(18) |
| C18-C19 | 1.418(2) | C18-C26 | 1.4380(19) |
| C19-C20 | 1.481(2) | C20-C21 | 1.392(2) |
| C20-C25 | 1.398(2) | C21-C22 | 1.394(2) |
| C22-C23 | 1.388(3) | C23-C24 | 1.396(2) |
| C24-C25 | 1.391(2) | C25-C26 | 1.485(2) |
| N1-C33 | 1.5073(18) | N1-H1B | 0.91(2) |
| N1-H1C | 0.93(2) | N1-H1D | 0.90(2) |
| C27-C32 | 1.388(2) | C27-C28 | 1.390(2) |
| C28-C29 | 1.391(2) | C29-C30 | 1.383(3) |
| C30-C31 | 1.387(2) | C31-C32 | 1.398(2) |
| C32-C33 | 1.5172(19) | C33-C34 | 1.518(2) |

TABLE 5

Selected bond angles, (°), for compound 8

| C10-O3-H3A | 107.0(15) | C2-C1-C7 | 120.96(13) |
|---|---|---|---|
| C3-C2-C1 | 120.72(13) | C2-C3-C5 | 118.95(12) |
| C2-C3-C4 | 121.50(12) | C5-C3-C4 | 119.48(12) |
| O1-C4-O2 | 125.44(12) | O1-C4-C3 | 116.78(12) |
| O2-C4-C3 | 117.77(12) | C6-C5-C3 | 120.23(13) |
| C5-C6-C7 | 121.32(13) | C6-C7-C1 | 117.75(12) |
| C6-C7-C8 | 120.71(12) | C1-C7-C8 | 121.43(12) |
| C7-C8-C9 | 115.87(10) | C18-C9-C8 | 111.09(11) |
| C18-C9-C17 | 110.70(11) | C8-C9-C17 | 113.19(11) |
| C18-C9-C10 | 108.74(10) | C8-C9-C10 | 109.89(10) |
| C17-C9-C10 | 102.86(10) | O3-C10-C11 | 109.18(11) |
| O3-C10-C9 | 109.69(10) | C11-C10-C9 | 103.26(10) |
| C16-C11-C12 | 121.07(13) | C16-C11-C10 | 110.61(11) |
| C12-C11-C10 | 127.84(13) | C13-C12-C11 | 118.29(14) |
| C14-C13-C12 | 120.72(13) | C13-C14-C15 | 120.99(14) |
| C16-C15-C14 | 118.34(14) | C15-C16-C11 | 120.58(13) |
| C15-C16-C17 | 129.14(13) | C11-C16-C17 | 110.16(12) |
| C16-C17-C9 | 103.90(11) | C19-C18-C26 | 109.64(13) |
| C19-C18-C9 | 124.70(12) | C26-C18-C9 | 125.65(13) |
| C18-C19-C20 | 107.21(12) | C21-C20-C25 | 120.31(14) |
| C21-C20-C19 | 131.41(14) | C25-C20-C19 | 108.27(13) |
| C20-C21-C22 | 118.51(15) | C23-C22-C21 | 121.31(15) |
| C22-C23-C24 | 120.24(15) | C25-C24-C23 | 118.68(15) |
| C24-C25-C20 | 120.94(14) | C24-C25-C26 | 130.48(14) |
| C20-C25-C26 | 108.57(13) | C18-C26-C25 | 106.29(13) |
| C33-N1-H1B | 108.3(13) | C33-N1-H1C | 112.0(13) |
| H1B-N1-H1C | 107.4(18) | C33-N1-H1D | 111.6(13) |
| H1B-N1-H1D | 112.5(18) | H1C-N1-H1D | 105.0(17) |
| C32-C27-C28 | 120.51(14) | C27-C28-C29 | 120.09(15) |
| C30-C29-C28 | 119.78(14) | C29-C30-C31 | 120.10(14) |
| C30-C31-C32 | 120.61(15) | C27-C32-C31 | 118.89(14) |
| C27-C32-C33 | 122.36(13) | C31-C32-C33 | 118.74(13) |
| N1-C33-C32 | 110.61(11) | N1-C33-C34 | 108.16(11) |
| C32-C33-C34 | 114.30(12) | | |

TABLE 6

Selected torsion angles, (°), for compound 8

| C7-C1-C2-C3 | 0.4(2) | C1-C2-C3-C5 | 1.7(2) |
|---|---|---|---|
| C1-C2-C3-C4 | −175.50(12) | C2-C3-C4-O1 | 156.41(13) |
| C5-C3-C4-O1 | −20.75(18) | C2-C3-C4-O2 | −22.38(18) |
| C5-C3-C4-O2 | 160.46(12) | C2-C3-C5-C6 | −1.7(2) |
| C4-C3-C5-C6 | 175.57(12) | C3-C5-C6-C7 | −0.5(2) |
| C5-C6-C7-C1 | 2.5(2) | C5-C6-C7-C8 | −173.65(12) |
| C2-C1-C7-C6 | −2.52(19) | C2-C1-C7-C8 | 173.64(12) |
| C6-C7-C8-C9 | −83.92(16) | C1-C7-C8-C9 | 100.03(15) |
| C7-C8-C9-C18 | −64.43(16) | C7-C8-C9-C17 | 60.83(15) |
| C7-C8-C9-C10 | 175.19(12) | C18-C9-C10-O3 | −155.49(11) |
| C8-C9-C10-O3 | −33.70(15) | C17-C9-C10-O3 | 87.10(12) |
| C18-C9-C10-C11 | 88.22(13) | C8-C9-C10-C11 | −149.99(11) |
| C17-C9-C10-C11 | −29.19(13) | O3-C10-C11-C16 | −96.36(13) |
| C9-C10-C11-C16 | 20.29(15) | O3-C10-C11-C12 | 75.67(18) |
| C9-C10-C11-C12 | −167.68(14) | C16-C11-C12-C13 | −0.5(2) |
| C10-C11-C12-C13 | −171.75(13) | C11-C12-C13-C14 | −0.3(2) |
| C12-C13-C14-C15 | 0.3(2) | C13-C14-C15-C16 | 0.4(2) |
| C14-C15-C16-C11 | −1.2(2) | C14-C15-C16-C17 | 174.32(14) |
| C12-C11-C16-C15 | 1.2(2) | C10-C11-C16-C15 | 173.88(13) |
| C12-C11-C16-C17 | −175.05(12) | C10-C11-C16-C17 | −2.40(16) |
| C15-C16-C17-C9 | 167.34(14) | C11-C16-C17-C9 | −16.79(15) |
| C18-C9-C17-C16 | −88.09(12) | C8-C9-C17-C16 | 146.44(11) |
| C10-C9-C17-C16 | 27.92(13) | C8-C9-C18-C19 | −44.46(16) |
| C17-C9-C18-C19 | −171.10(11) | C10-C9-C18-C19 | 76.60(15) |
| C8-C9-C18-C26 | 137.25(13) | C17-C9-C18-C26 | 10.60(17) |
| C10-C9-C18-C26 | −101.70(15) | C26-C18-C19-C20 | −1.81(14) |
| C9-C18-C19-C20 | 179.67(11) | C18-C19-C20-C21 | −179.77(14) |
| C18-C19-C20-C25 | 1.34(15) | C25-C20-C21-C22 | 1.5(2) |
| C19-C20-C21-C22 | −177.24(14) | C20-C21-C22-C23 | −1.1(2) |
| C21-C22-C23-C24 | −0.3(2) | C22-C23-C24-C25 | 1.2(2) |
| C23-C24-C25-C20 | −0.7(2) | C23-C24-C25-C26 | 177.73(14) |
| C21-C20-C25-C24 | −0.6(2) | C19-C20-C25-C24 | 178.39(12) |
| C21-C20-C25-C26 | −179.41(12) | C19-C20-C25-C26 | −0.38(15) |
| C19-C18-C26-C25 | 1.57(15) | C9-C18-C26-C25 | −179.92(11) |
| C24-C25-C26-C18 | −179.32(14) | C20-C25-C26-C18 | −0.71(15) |
| C32-C27-C28-C29 | −1.2(2) | C27-C28-C29-C30 | 0.3(2) |

TABLE 6-continued

Selected torsion angles, (°), for compound 8

| | | | |
|---|---|---|---|
| C28-C29-C30-C31 | 0.4(2) | C29-C30-C31-C32 | −0.3(2) |
| C28-C27-C32-C31 | 1.2(2) | C28-C27-C32-C33 | −178.07(13) |
| C30-C31-C32-C27 | −0.5(2) | C30-C31-C32-C33 | 178.85(14) |
| C27-C32-C33-N1 | −86.99(16) | C31-C32-C33-N1 | 93.72(15) |
| C27-C32-C33-C34 | 35.36(18) | C31-C32-C33-C34 | −143.93(14) |

TABLE 7

Anisotropic atomic displacement parameters, (Å$^2$), for compound 8 The anisotropic atomic displacement factor exponent takes the form:
$-2\pi^2 [h^2 a^{*2} U_{11} + \ldots + 2hka^* b^* U_{12}]$

| | $U_{11}$ | $U_{22}$ | $U_{33}$ | $U_{23}$ | $U_{13}$ | $U_{12}$ |
|---|---|---|---|---|---|---|
| O1 | 0.0325(5) | 0.0206(5) | 0.0153(4) | 0.0025(4) | 0.0015(4) | 0.0044(4) |
| O2 | 0.0255(5) | 0.0206(5) | 0.0123(4) | −0.0017(4) | 0.0024(3) | −0.0014(4) |
| O3 | 0.0205(4) | 0.0232(5) | 0.0116(4) | −0.0002(4) | 0.0027(3) | 0.0016(4) |
| C1 | 0.0257(7) | 0.0179(7) | 0.0159(6) | 0.0017(5) | 0.0018(5) | −0.0028(5) |
| C2 | 0.0267(7) | 0.0171(7) | 0.0139(6) | −0.0035(5) | 0.0024(5) | −0.0019(5) |
| C3 | 0.0160(6) | 0.0187(7) | 0.0128(6) | −0.0004(5) | 0.0017(4) | 0.0011(5) |
| C4 | 0.0166(5) | 0.0193(7) | 0.0134(6) | 0.0000(5) | 0.0014(4) | −0.0018(5) |
| C5 | 0.0234(6) | 0.0155(7) | 0.0159(6) | −0.0001(5) | −0.0011(5) | 0.0020(5) |
| C6 | 0.0251(6) | 0.0175(7) | 0.0158(6) | −0.0030(5) | −0.0024(5) | 0.0028(5) |
| C7 | 0.0150(5) | 0.0213(7) | 0.0129(6) | 0.0000(5) | 0.0009(4) | 0.0028(5) |
| C8 | 0.0188(6) | 0.0217(7) | 0.0124(6) | −0.0007(5) | 0.0000(4) | 0.0018(5) |
| C9 | 0.0186(6) | 0.0177(7) | 0.0117(5) | 0.0004(5) | 0.0007(4) | −0.0002(5) |
| C10 | 0.0206(6) | 0.0190(7) | 0.0121(6) | 0.0000(5) | 0.0005(4) | 0.0022(5) |
| C11 | 0.0201(6) | 0.0185(7) | 0.0163(6) | −0.0030(5) | 0.0004(5) | 0.0033(5) |
| C12 | 0.0234(6) | 0.0249(8) | 0.0166(6) | −0.0018(5) | −0.0015(5) | 0.0056(5) |
| C13 | 0.0237(7) | 0.0322(9) | 0.0216(7) | −0.0074(6) | −0.0074(5) | 0.0074(6) |
| C14 | 0.0196(7) | 0.0284(8) | 0.0324(8) | −0.0099(6) | −0.0049(6) | 0.0015(6) |
| C15 | 0.0199(6) | 0.0229(7) | 0.0282(7) | −0.0035(6) | 0.0008(5) | 0.0012(6) |
| C16 | 0.0186(6) | 0.0198(7) | 0.0178(6) | −0.0023(5) | 0.0007(5) | 0.0028(5) |
| C17 | 0.0213(6) | 0.0203(7) | 0.0151(6) | 0.0004(5) | 0.0018(5) | −0.0008(5) |
| C18 | 0.0200(6) | 0.0206(7) | 0.0101(5) | 0.0011(5) | −0.0009(4) | 0.0004(5) |
| C19 | 0.0245(7) | 0.0249(8) | 0.0176(6) | −0.0024(5) | 0.0008(5) | 0.0029(5) |
| C20 | 0.0256(7) | 0.0227(7) | 0.0124(6) | 0.0001(5) | 0.0015(5) | 0.0027(5) |
| C21 | 0.0392(8) | 0.0237(8) | 0.0215(6) | −0.0032(6) | 0.0059(6) | −0.0017(7) |
| C22 | 0.063(2) | 0.0236(16) | 0.0226(13) | −0.0024(11) | 0.0090(13) | 0.0165(15) |
| C23 | 0.0359(8) | 0.0356(9) | 0.0240(7) | −0.0034(6) | 0.0049(6) | 0.0140(7) |
| C24 | 0.0253(7) | 0.0331(9) | 0.0225(7) | −0.0050(6) | 0.0034(5) | 0.0047(6) |
| C25 | 0.0253(7) | 0.0253(8) | 0.0129(5) | 0.0003(5) | 0.0016(5) | 0.0035(5) |
| C26 | 0.0277(7) | 0.0248(8) | 0.0197(6) | −0.0005(6) | 0.0069(5) | 0.0012(6) |
| C18A | 0.0200(6) | 0.0206(7) | 0.0101(5) | 0.0011(5) | −0.0009(4) | 0.0004(5) |
| C19A | 0.0245(7) | 0.0249(8) | 0.0176(6) | −0.0024(5) | 0.0008(5) | 0.0029(5) |
| C20A | 0.0256(7) | 0.0227(7) | 0.0124(6) | 0.0001(5) | 0.0015(5) | 0.0027(5) |
| C21A | 0.0392(8) | 0.0237(8) | 0.0215(6) | −0.0032(6) | 0.0059(6) | −0.0017(7) |
| C22A | 0.0392(8) | 0.0237(8) | 0.0215(6) | −0.0032(6) | 0.0059(6) | −0.0017(7) |
| C23A | 0.0359(8) | 0.0356(9) | 0.0240(7) | −0.0034(6) | 0.0049(6) | 0.0140(7) |
| C24A | 0.0253(7) | 0.0331(9) | 0.0225(7) | −0.0050(6) | 0.0034(5) | 0.0047(6) |
| C25A | 0.0253(7) | 0.0253(8) | 0.0129(5) | 0.0003(5) | 0.0016(5) | 0.0035(5) |
| C26A | 0.0277(7) | 0.0248(8) | 0.0197(6) | −0.0005(6) | 0.0069(5) | 0.0012(6) |
| N1 | 0.0248(6) | 0.0191(6) | 0.0143(5) | −0.0013(5) | 0.0005(4) | −0.0007(5) |
| C27 | 0.0216(6) | 0.0233(7) | 0.0213(7) | −0.0001(5) | 0.0017(5) | −0.0030(5) |
| C28 | 0.0250(7) | 0.0228(8) | 0.0293(7) | 0.0035(6) | 0.0038(6) | −0.0021(6) |
| C29 | 0.0265(7) | 0.0298(9) | 0.0254(7) | 0.0087(6) | −0.0001(5) | −0.0017(6) |
| C30 | 0.0326(8) | 0.0357(9) | 0.0214(7) | 0.0019(6) | −0.0041(6) | −0.0050(7) |
| C31 | 0.0286(7) | 0.0238(8) | 0.0234(7) | 0.0001(6) | −0.0034(6) | −0.0053(6) |
| C32 | 0.0169(6) | 0.0233(7) | 0.0198(6) | 0.0024(5) | 0.0007(5) | −0.0024(5) |
| C33 | 0.0196(6) | 0.0205(7) | 0.0212(6) | 0.0023(5) | 0.0001(5) | −0.0031(5) |
| C34 | 0.0280(7) | 0.0264(8) | 0.0232(7) | 0.0029(6) | 0.0065(6) | 0.0024(6) |

APPENDIX 3

| Compound No. | Chemical Name |
|---|---|
| 1 | 4-(((1S,2S)-1-hydroxy-2,3-dihydro-1H,1′H-2,2′-biinden-2-yl) methyl)benzoic acid |
| 2 | 4-(((1S,2S)-1-hydroxy-2,3-dihydro-1H,1′H-2,2′-biinden-2-yl) methyl)benzoic acid |
| 3 | 4-(((1R,2R)-1-hydroxy-2,3-dihydro-1H,1′H-2,2′-biinden-2-yl)methyl)benzoic acid |
| 4 | 4-(((1R,2S)-1-hydroxy-2,3-dihydro-1H,1′H-2,2′-biinden-2-yl)methyl)benzoic acid |
| 5 | 4-(((1S,2R)-1-hydroxy-2,3-dihydro-1H,1′H-2,2′-biinden-2-yl)methyl)benzoic acid |
| 6 | 6-(Methylamino)hexane-1,2,3,4,5-pentanol 4-(((1S,2S)-1-hydroxy-2,3-dihydro-1H,1′H-2,2′-biinden-2-yl)methyl)benzoate |

APPENDIX 3-continued

| Compound No. | Chemical Name |
|---|---|
| 7 | 6-(Methylamino)hexane-1,2,3,4,5-pentanol 4-((((1S,2R)-1-hydroxy-2,3-dihydro-1H,1'H-2,2'-biinden-2-yl)methyl)benzoate |
| 8 | (S)-1-Phenylethylammonium 4-((((1S,2S)-1-hydroxy-2,3-dihydro-1H,1'H-2,2'-biinden-2-yl)methyl)benzoate |
| 9 | (R)-1-Phenylethylammonium 4-((((1R,2S)-1-hydroxy-2,3-dihydro-1H,1'H-2,2'-biinden-2-yl)methyl)benzoate |
| 10 | methyl 4-((((1R,2R)-1-hydroxy-2,3-dihydro-1H,1'H-[2,2'-biinden]-2-yl)methyl)benzoate |
| 11 | ethyl 4-((((1R,2R)-1-hydroxy-2,3-dihydro-1H,1'H-[2,2'-biinden]-2-yl)methyl)benzoate |
| 12 | propyl 4-((((1R,2R)-1-hydroxy-2,3-dihydro-1H,1'H-[2,2'-biinden]-2-yl)methyl)benzoate |
| 13 | 4-{[(1'R,2'R)-1'-hydroxy-1',3'-dihydro-1H,2'H-2,2'-biinden-2'-yl]methyl}Benzamide |
| 14 | 4-{[(1'R,2'R)-1'-hydroxy-1',3'-dihydro-1H,2'H-2,2'-biinden-2'-yl]methyl}-N-(2-hydroxyethyl)benzamide |
| 15 | 4-{[(1'R,2'R)-1'-hydroxy-1',3'-dihydro-1H,2'H-2,2'-biinden-2'-yl]methyl}-N-methylbenzamide |
| 16 | 4-{[(1'R,2'R)-1'-hydroxy-1',3'-dihydro-1H,2'H-2,2'-biinden-2'-yl]methyl}-N,N-dimethylbenzamide |
| 17 | methyl 4-((((1S,2S)-1-hydroxy-2,3-dihydro-1H,1'H-[2,2'-biinden]-2-yl)methyl)benzoate |
| 18 | ethyl 4-((((1S,2S)-1-hydroxy-2,3-dihydro-1H,1'H-[2,2'-biinden]-2-yl)methyl)benzoate |
| 19 | propyl 4-((((1S,2S)-1-hydroxy-2,3-dihydro-1H,1'H-[2,2'-biinden]-2-yl)methyl)benzoate |
| 20 | 4-{[(1'S,2'S)-1'-hydroxy-1',3'-dihydro-1H,2'H-2,2'-biinden-2'-yl]methyl}Benzamide |
| 21 | 4-{[(1'S,2'S)-1'-hydroxy-1',3'-dihydro-1H,2'H-2,2'-biinden-2'-yl]methyl}-N-(2-hydroxyethyl)benzamide |
| 22 | 4-{[(1'S,2'S)-1'-hydroxy-1',3'-dihydro-1H,2'H-2,2'-biinden-2'-yl]methyl}-N-methylbenzamide |
| 23 | 4-{[(1'S,2'S)-1'-hydroxy-1',3'-dihydro-1H,2'H-2,2'-biinden-2'-yl]methyl}-N,N-dimethylbenzamide |
| 24 | 4-{[(1'R,2'R)-1'-(L-leucyloxy)-1',3'-dihydro-1H,2'H-2,2'-biinden-2'-yl]methyl}benzoic acid |
| 25 | 4-{[(1'R,2'R)-1'-(L-valyloxy)-1',3'-dihydro-1H,2'H-2,2'-biinden-2'-yl]methyl}benzoic acid |
| 26 | 4-{[(1'R,2'R)-1'-(L-isoleucyloxy)-1',3'-dihydro-1H,2'H-2,2'-biinden-2'yl]methyl}benzoic acid |
| 27 | 4-{[(1'R,2'R)-1'-(glycyloxy)-1',3'-dihydro-1H,2'H-2,2'-biinden-2'-yl]methyl}benzoic acid |
| 28 | 4-{[(1'S,2'S)-1'-(L-leucyloxy)-1',3'-dihydro-1H,2'H-2,2'-biinden-2'-yl]methyl}benzoic acid |
| 29 | 4-{[(1'S,2'S)-1'-(L-valyloxy)-1',3'-dihydro-1H,2'H-2,2'-biinden-2'-yl]methyl}benzoic acid |
| 30 | 4-{[(1'S,2'S)-1'-(L-isoleucyloxy)-1',3'-dihydro-1H,2'H-2,2'-biinden-2'-yl]methyl}benzoic acid |
| 31 | 4-{[(1'S,2'S)-1'-(glycyloxy)-1',3'-dihydro-1H,2'H-2,2'-biinden-2'-yl]methyl}benzoic acid |
| 32 | methyl 4-((((1R,2R)-1-(((S)-2-amino-4-methylpentanoyl)oxy)-2,3-dihydro-1H,1'H-[2,2'-biinden]-2-yl)methyl)benzoate |
| 33 | ethyl 4-((((1R,2R)-1-(((S)-2-amino-4-methylpentanoyl)oxy)-2,3-dihydro-1H,1'H-[2,2'-biinden]-2-yl)methyl)benzoate |
| 34 | propyl 4-((((1R,2R)-1-(((S)-2-amino-4-methylpentanoyl)oxy)-2,3-dihydro-1H,1'H-[2,2'-biinden]-2-yl)methyl)benzoate |
| 35 | (1R,2R)-2-(4-carbamoylbenzyl)-2,3-dihydro-1H,1'H-2,2'-biinden-1-yl L-leucinate |
| 36 | (1R,2R)-2-{4-[(2-hydroxyethyl)carbamoyl]benzyl}-2,3-dihydro-1H,1'H-2,2'-biinden-1-yl L-leucinate |
| 37 | (1R,2R)-2-[4-(methylcarbamoyl)benzyl]-2,3-dihydro-1H,1'H-2,2'-biinden-1-yl L-leucinate |
| 38 | (1R,2R)-2-[4-(dimethylcarbamoyl)benzyl]-2,3-dihydro-1H,1'H-2,2'-biinden-1-yl L-leucinate (38) |
| 39 | methyl 4-((((1S,2S)-1-(((S)-2-amino-4-methylpentanoyl)oxy)-2,3-dihydro-1H,1'H-[2,2'-biinden]-2-yl)methyl)benzoate |
| 40 | ethyl 4-((((1S,2S)-1-(((S)-2-amino-4-methylpentanoyl)oxy)-2,3-dihydro-1H,1'H-[2,2'-biinden]-2-yl)methyl)benzoate |
| 41 | propyl 4-((((1S,2S)-1-(((S)-2-amino-4-methylpentanoyl)oxy)-2,3-dihydro-1H,1'H-[2,2'-biinden]-2-yl)methyl)benzoate |
| 42 | (1S,2S)-2-(4-carbamoylbenzyl)-2,3-dihydro-1H,1'H-2,2'-biinden-1-yl L-leucinate |
| 43 | (1S,2S)-2-{4-[(2-Hydroxyethyl)carbamoyl]benzyl}-2,3-dihydro-1H,1'H-2,2'-biinden-1-yl leucinate |
| 44 | (1S,2S)-2-[4-(methylcarbamoyl)benzyl]-2,3-dihydro-1H,1'H-2,2'-biinden-1-yl L-leucinate |
| 45 | (1S,2S)-2-[4-(dimethylcarbamoyl)benzyl]-2,3-dihydro-1H,1'H-2,2'-biinden-1-yl L-leucinate |

APPENDIX 3-continued

| Compound No. | Chemical Name |
|---|---|
| 46 | 2-hydroxy-5-(4-(((1R,2R)-1-hydroxy-2,3-dihydro-1H,1'H-[2,2'-biinden]-2-yl)methyl)benzamido)benzoic acid |
| 47 | 2-hydroxy-5-(4-(((1S,2S)-1-hydroxy-2,3-dihydro-1H,1'H-[2,2'-biinden]-2-yl)methyl)benzamido)benzoic acid |

The invention claimed is:

1. A compound of the absolute stereochemistry and formula:

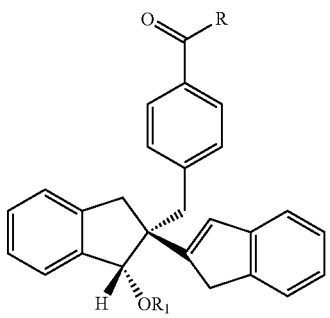

wherein $R^1$ is leucinate and R is selected from: $NH_2$, $NHCH_2CH_2OH$, $NHCH_3$, or $N(CH_3)_2$.

2. A compound of the absolute stereochemistry and formula:

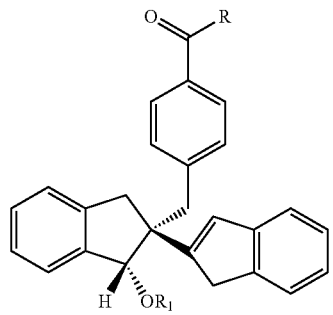

wherein $R^1$ is leucinate and R is selected from: $NH(CH_2)_2OH$, or $N(CH_3)_2$.

3. A pharmaceutical composition comprising an effective amount of a compound as claimed in claim 1 and a pharmaceutically acceptable carrier.

4. A pharmaceutical composition comprising an effective amount of a compound as claimed in claim 2 and a pharmaceutically acceptable carrier.

* * * * *